US012716902B2

(12) United States Patent
Kawabe et al.

(10) Patent No.: US 12,716,902 B2
(45) Date of Patent: Aug. 25, 2026

(54) METHOD FOR MEASURING TITER OF COAGULATION FACTOR INHIBITOR

(71) Applicants: SEKISUI MEDICAL CO., LTD., Chuo-ku (JP); PUBLIC UNIVERSITY CORPORATION NARA MEDICAL UNIVERSITY, Kashihara (JP)

(72) Inventors: Toshiki Kawabe, Chuo-ku (JP); Yukio Oda, Chuo-ku (JP); Mari Emmi, Chuo-ku (JP); Midori Shima, Kashihara (JP); Keiji Nogami, Kashihara (JP); Kenichi Ogiwara, Kashihara (JP); Naruto Shimonishi, Kashihara (JP)

(73) Assignees: SEKISUI MEDICAL CO., LTD., Chuo-ku (JP); PUBLIC UNIVERSITY CORPORATION NARA MEDICAL UNIVERSITY, Kashihara (JP)

( * ) Notice: Subject to any disclaimer, the term of this patent is extended or adjusted under 35 U.S.C. 154(b) by 1309 days.

(21) Appl. No.: 17/606,274

(22) PCT Filed: Apr. 23, 2020

(86) PCT No.: PCT/JP2020/017507
§ 371 (c)(1),
(2) Date: Oct. 25, 2021

(87) PCT Pub. No.: WO2020/218425
PCT Pub. Date: Oct. 29, 2020

(65) Prior Publication Data

US 2022/0326262 A1 Oct. 13, 2022

(30) Foreign Application Priority Data

Apr. 26, 2019 (JP) ................................ 2019-086658

(51) Int. Cl.
*G01N 33/86* (2006.01)
*G01N 33/49* (2006.01)

(52) U.S. Cl.
CPC ......... *G01N 33/86* (2013.01); *G01N 33/4905* (2013.01)

(58) Field of Classification Search
CPC .......................... G01N 33/86; G01N 33/4905
See application file for complete search history.

(56) References Cited

U.S. PATENT DOCUMENTS

2008/0183431 A1* 7/2008 Matsuo ................ G01N 21/272
702/187
2011/0129862 A1 6/2011 Nakamura et al.
(Continued)

FOREIGN PATENT DOCUMENTS

CN 106018282 A 10/2016
CN 107533071 A 1/2018
(Continued)

OTHER PUBLICATIONS

Combined Chinese Office Action and Search Report issued on Jul. 14, 2023 for Chinese Patent Application No. 202080031301.4 (with English machine translation), 14 pages.
(Continued)

*Primary Examiner* — Lyle Alexander
*Assistant Examiner* — Dwan A Gerido
(74) *Attorney, Agent, or Firm* — Oblon, McClelland, Maier & Neustadt, L.L.P.

(57) ABSTRACT

A method for measuring a titer of a coagulation factor inhibitor. The-method includes: preparing a mixed specimen containing a-subject blood specimen and a normal blood specimen; heating the mixed specimen and acquiring a coagulation reaction-curve for the heated mixed specimen; acquiring a-coagulation reaction curve for the mixed speci-
(Continued)

men that has-not been heated; calculating a parameter related to the-coagulation reaction curve of the mixed specimen that has-not been heated as a first parameter; calculating a-parameter related to the coagulation reaction curve of the-heated mixed specimen as a second parameter; and-calculating a titer of a coagulation factor inhibitor in-the subject blood specimen on the basis of the ratio or the difference between the first parameter and the second-parameter.

8 Claims, 32 Drawing Sheets

(56) References Cited

U.S. PATENT DOCUMENTS

| | | | |
|---|---|---|---|
| 2016/0178651 | A1 | 6/2016 | Shima et al. |
| 2016/0291042 | A1 | 10/2016 | Kumano et al. |
| 2018/0031539 | A1 | 2/2018 | Shima et al. |
| 2018/0045709 | A1 | 2/2018 | Shima et al. |
| 2018/0292420 | A1 | 10/2018 | Evans et al. |
| 2018/0356433 | A1 | 12/2018 | Kumano |
| 2021/0333295 | A1 | 10/2021 | Kawabe et al. |

FOREIGN PATENT DOCUMENTS

| | | | |
|---|---|---|---|
| CN | 109030837 | A | 12/2018 |
| EP | 3 882 628 | A1 | 9/2021 |
| JP | 2016-118442 | A | 6/2016 |
| JP | 2016-194426 | A | 11/2016 |
| JP | 2017-106925 | A | 6/2017 |
| JP | 2018-17619 | A | 2/2018 |
| JP | 2018-517150 | A | 6/2018 |

OTHER PUBLICATIONS

Shou Shuang, “Contrast to Detection of Three Coagulation Markers by Two Testing Systems”, Department of Epidemiology and Health Statistics, China Master’s Theses Full-text Database (CMFD), Sep. 15, 2010, (72 pages in total, including an English abstract).

Donna Castellone, “Inhibitor Identification in the Coagulation Laboratory”, Laboratory Medicine, vol. 44, No. 4, Nov. 1, 2013, e118-e120.

Daiki Shimomura, et al., “The First-Derivative Curve of the Coagulation Waveform Reveals the Cause of aPTT Prolongation”, Clinical and Applied Thrombosis/Hemostasis, vol. 26, Dec. 29, 2020, pp. 1-8.

Extended European Search Report issued on Aug. 31, 2023 in European Patent Application No. 20795805.9, 6 pages.

International Search Report issued on Jul. 14, 2020 in PCT/JP2020/017507 filed Apr. 23, 2020, 3 pages.

Downey, C., et al., “Novel and diagnostically applicable information from optical waveform analysis of blood coagulation in disseminated intravascular coagulation”, British Journal of Haematology, vol. 98, 1997, pp. 68-73.

Wada, H., “APTT waveform”, Japanese Journal of Thrombosis and Hemostasis, vol. 29, No. 4. 2018, pp. 413-420.

Matsumoto, T., “Usage and view of clot waveform analysis”, Medical Technology, vol. 46, No. 1, 2018, pp. 66-71, 7 total pages.

* cited by examiner

Pa
× Amax (pH100%)
NP LA HA HB InL InM InH
Pb
Pb/Pa
Pb-Pa

FIG. 18E

A
B
C
D
PARAMETER RATIO (Pa/Pb)
Log (MEASURED TITER, BU/mL)
CALIBRATION CURVE
PARAMETER RATIO (Pa/Pb)
Log (MEASURED TITER, BU/mL)
CALCULATED TITER
MEASURED TITER (BU/mL)
CALCULATED TITER
MEASURED TITER (BU/mL)

A
PARAMETER RATIO (Pa/Pb)
Log (MEASURED TITER, BU/mL)
B
CALIBRATION CURVE
PARAMETER RATIO (Pa/Pb)
Log (MEASURED TITER, BU/mL)
C
CALCULATED TITER
MEASURED TITER (BU/mL)
D
CALCULATED TITER
MEASURED TITER (BU/mL)

A
B
C
D
PARAMETER RATIO (Pa/Pb)
Log (MEASURED TITER, BU/mL)
CALIBRATION CURVE
PARAMETER RATIO (Pa/Pb)
Log (MEASURED TITER, BU/mL)
CALCULATED TITER
MEASURED TITER (BU/mL)
CALCULATED TITER
MEASURED TITER (BU/mL)

A
B
C
D
PARAMETER RATIO (Pa/Pb)
Log (MEASURED TITER, BU/mL)
CALIBRATION CURVE
CALCULATED TITER
MEASURED TITER (BU/mL)

A
PARAMETER DIFFERENCE (Pa/Pb)
Log (MEASURED TITER, BU/mL)
B
CALIBRATION CURVE
PARAMETER DIFFERENCE (Pa/Pb)
Log (MEASURED TITER, BU/mL)
C
CALCULATED TITER
MEASURED TITER (BU/mL)
D
CALCULATED TITER
MEASURED TITER (BU/mL)

METHOD FOR MEASURING TITER OF COAGULATION FACTOR INHIBITOR

This application is a national stage application of PCT/JP2020/017507, filed Apr. 23, 2020, which claims priority to Japanese application JP 2019/086658, files Apr. 26, 2019. The entire contents of both applications are incorporated herein by reference.

FIELD OF THE INVENTION

The present invention relates to a method for measuring a titer of a coagulation factor inhibitor of a blood specimen.

BACKGROUND OF THE INVENTION

The blood coagulation test is a test for diagnosing a blood coagulation ability of a patient with the addition of a predetermined reagent to a blood specimen of the patient and measuring, for example, the blood coagulation time. By the blood coagulation test, the state of a hemostatic ability or fibrinolytic capacity of the patient can be grasped. Typical examples of the blood coagulation time include a prothrombin time (PT), an activated partial thromboplastin time (APTT), and a thrombin time. In recent years, an automatic analyzer that automatically measures a blood coagulation test has been widely used, and the blood coagulation test can be easily performed.

Examples of the cause of prolongation of blood coagulation time include influence of a coagulation inhibitor, reduction of components involved in coagulation, congenital deficiency of blood coagulation factors, and acquired autoantibodies that inhibit coagulation reaction. For example, in a case where prolongation of APTT is observed, a cross-mixing test is generally performed, and it is determined by which of a coagulation factor inhibitor (anticoagulation factor), lupus anticoagulant (LA), or deficiency of a coagulation factor such as hemophilia, the prolongation of APTT is caused. In the cross-mixing test, the APTT (immediate reaction) immediately after mixture, and the APTT (delayed reaction) after incubation at 37° C. for 2 hours, of a normal plasma, a plasma to be tested, and mixed plasmas containing a plasma to be tested and a normal plasma at various volume ratios are measured. The measured values are graphed by putting the measured values (seconds) of APTT on the vertical axis and the volume ratios of the plasma to be tested to the normal plasma on the horizontal axis. Each of the created graphs of the immediate reaction and delayed reaction shows a pattern of "downward convex", "straight line", or "upward convex" depending on the APTT prolongation factor. On the basis of such patterns of the immediate reaction and delayed reaction, the APTT prolongation factor is determined.

In a case where the APTT prolongation is determined to be caused by a coagulation factor inhibitor, the inhibitor titer is generally measured by a Bethesda assay. In the Bethesda assay, a sample obtained by mixing a dilution series of a plasma to be tested with a normal plasma is heated at 37° C. for 2 hours, and then the residual activity of the coagulation factor in the sample is measured, and the titer of an inhibitor of the coagulation factor is measured from the measured value on the basis of the calibration curve. The Bethesda assay is currently a standard assay for the inhibitor titer against a coagulation factor VIII (FVIII) and a coagulation factor IX (FIX).

In the blood coagulation test, a coagulation reaction curve can be obtained by measuring the amount of blood coagulation reaction over time after addition of a reagent to a blood specimen. The coagulation reaction curve has a different shape depending on the type of the abnormality in the blood coagulation system (Non Patent Literature 1). For this reason, a method for determining the abnormality in the blood coagulation system on the basis of a coagulation reaction curve has been disclosed. For example, Patent Literatures 1 to 3 disclose a method for evaluating the presence or absence of abnormalities of coagulation factors in a patient, on the basis of the parameters related to primary and secondary differential curves of a coagulation reaction curve for the blood of the patient, for example, the maximum coagulation rate, the maximum coagulation acceleration, and the maximum coagulation deceleration. Patent Literature 4 discloses a method for determining the severity of hemophilia on the basis of the average rate of the change in the coagulation rate during the time when the coagulation reaction of a patient reaches the maximum coagulation rate or the maximum coagulation acceleration. Patent Literature 5 discloses a method for determining the presence of a FVIII inhibitor on the basis of the ratio of the slope of the straight line representing the coagulation time for the dilution ratio of patient plasma to the slope of the straight line representing the coagulation time for the dilution ratio of control plasma.

Patent Literature 1: JP 2016-194426 A
Patent Literature 2: JP 2016-118442 A
Patent Literature 3: JP 2017-106925 A
Patent Literature 4: JP 2018-017619 A
Patent Literature 5: JP 2018-517150 A

Non Patent Literature

Non Patent Literature 1: British Journal of Haematology, 1997, 98: 68-73

SUMMARY OF THE INVENTION

Technical Problem

The Bethesda assay requires a long time of 2 hours or more for the measurement including the heating time of a sample, and further is not suitable for automatic measurement by an analyzer. When taking further the time for the above-described cross-mixing test into consideration, the current measurement of inhibitor titer by the Bethesda assay requires a lot of labor and time. With respect to the Bethesda assay, in the "Inhibitor (anticoagulation factor) assay" of Glossary (www.jsth.org/glossary/) of The Japanese Society on Thrombosis and Hemostasis, there are descriptions that "the reference value is "not detected", and 0.5 BU/ml or more is determined to be positive", and that "it is difficult to accurately measure the range of 0 to 0.5 BU/ml", and therefore, the lower limit of detection is 0.5 BU/mL.

Accordingly, a method for measuring a titer of a coagulation factor inhibitor simply and in a short time has been demanded. It is more desirable if the measurement of inhibitor titer can be automated.

Solution to Problem

The present inventors found that the titer of a coagulation factor inhibitor can be measured in an extremely shorter time than that of a conventional method, by using various parameters derived from coagulation reaction curves of a mixed specimen of a subject blood specimen and a normal blood specimen, which has been heated for a short time and a mixed specimen of a subject blood specimen and a normal blood specimen, which has not been heated.

The present invention provides the following.

[1] A method for measuring a titer of a coagulation factor inhibitor, including:

preparing a mixed specimen containing a subject blood specimen and a normal blood specimen;

heating the mixed specimen and acquiring a coagulation reaction curve for the heated mixed specimen;

acquiring a coagulation reaction curve for the mixed specimen that has not been heated;

calculating a parameter related to the coagulation reaction curve of the mixed specimen that has not been heated as a first parameter;

calculating a parameter related to the coagulation reaction curve of the heated mixed specimen as a second parameter; and calculating a titer of a coagulation factor inhibitor in the subject blood specimen on the basis of the ratio or the difference between the first parameter and the second parameter.

[2] The method according to [1], in which the parameter related to the coagulation reaction curve is at least one parameter selected from the group consisting of a parameter related to the coagulation reaction curve, a parameter related to a primary differential curve of the coagulation reaction curve, and a parameter related to a secondary differential curve of the coagulation reaction curve.

[3] The method according to [1] or [2], in which the parameter is a parameter related to a weighted average point in a predetermined area of the primary differential curve or the secondary differential curve.

[4] The method according to [3], in which the weighted average point is a weighted average point of the primary differential curve represented by coordinates (vT, vH) defined by a weighted average time vT and a weighted average height vH, wherein when the primary differential curve is defined as F(t) (t represents time) and a time when F(t) is a predetermined value X is defined as t1, t2 (t1<t2), the vT and the vH are represented by the following formulas, respectively:

$$vT = \frac{M}{\sum_{i=t1}^{t2} F(i)} \tag{3}$$

$$vH = \frac{M}{\sum_{i=t1}^{t2} i} \tag{4}$$

wherein $$M = \sum_{i=t1}^{t2} (i \times F(i)), \tag{2}$$

the parameter related to the weighted average point includes one or more parameters selected from the group consisting of the vT, the vH, a peak width vB, a weighted average peak width vW, a B flattening vAB, a B time rate vTB, a W flattening vAW, a W time rate vTW, an average time vTa, an average height vHa, vTm, vABa, and vAWa, wherein the peak width vB is a length of time satisfying F(t)≥X from the t1 to t2, the weighted average peak width vW is a length of time satisfying F(t)≥vH from the t1 to t2, the vAB represents a ratio between the vH and the vB, the vTB represents a ratio between the vT and the vB, the vAW represents a ratio between the vH and the vW, the vTW represents a ratio between the vT and the vW, when F(t), t1 and t2 have the same definitions as described above, and the number of data points from F(t1) to F(t2) is defined as n, the vTa, the vHa, and the vTm are represented by the following formulas, respectively:

$$vTa = \frac{\sum_{i=t1}^{t2} i}{n} \tag{5}$$

$$vHa = \frac{\sum_{i=t1}^{t2} F(i)}{n} \tag{6}$$

$$vTm = \frac{t1 + t2}{2} \tag{7}$$

the vABa represents a ratio between the vHa and the vB, and the vAWa represents a ratio between the vHa and the vW.

[5] The method according to [3], in which the weighted average point is a weighted average point of a plus peak of the secondary differential curve represented by coordinates (pT, pH) defined by a weighted average time pT and a weighted average height pH, wherein, when the secondary differential curve is defined as F' (t) (t represents time) and a time when F' (t) is a predetermined value x is defined as t1, t2 (t1<t2), the pT and the pH are represented by the following formulas, respectively:

$$pT = \frac{M}{\sum_{i=t1}^{t2} F'(i)} \tag{3'}$$

$$pH = \frac{M}{\sum_{i=t1}^{t2} i} \tag{4'}$$

wherein $$M = \sum_{i=t1}^{t2} (i \times F'(i)), \tag{2'}$$

the parameter related to the weighted average point includes one or more parameters selected from the group consisting of the pT, the pH, a peak width pB, a weighted average peak width pW, a B flattening pAB, a B time rate pTB, a W flattening pAW, and a W time rate pTW, wherein the peak width pB is a length of time satisfying F' (t)≥X from the t1 to t2, the weighted average peak width pW is a length of time satisfying F'(t)≥pH from the t1 to t2, the pAB represents a ratio between the pH and the pB, the pTB represents a ratio between the pT and the pB, the pAW represents a ratio between the pH and the pW, and the pTW represents a ratio between the pT and the pW.

[6] The method according to [3], in which the weighted average point is a weighted average point of a minus peak of the secondary differential curve represented by coordinates (mT, mH) defined by a weighted average time mT and a weighted average height mH, wherein, when the secondary differential curve is defined as F' (t) (t represents time) and a time when F' (t) is a predetermined value X is defined as t1, t2 (t1<t2), the mT and the mH are represented by the following formulas, respectively:

$$mT = \frac{M}{\sum_{i=t1}^{t2} F'(i)} \tag{3}''$$

$$mH = \frac{M}{\sum_{i=t1}^{t2} i} \tag{4}''$$

wherein $$M = \sum_{i=t1}^{t2} (i \times F'(i)), \text{ and} \tag{2}'$$

the parameter related to the weighted average point includes one or more parameters selected from the group consisting of the mT, the mH, a peak width mB, a weighted average peak width mW, a B flattening mAB, a B time rate mTB, a W flattening mAW, and a W time rate mTW, wherein the peak width mB is a length of time satisfying F'(t)≤X from the t1 to t2, the weighted average peak width mW is a length of time satisfying F'(t)≤mH from the t1 to t2, the mAB represents a ratio between the mH and the mB, the mTB represents a ratio between the mT and the mB, the mAW represents a ratio between the mH and the mW, and the mTW represents a ratio between the mT and the mW.

[7] The method according to any one of [1] to [6], in which a titer of a coagulation factor inhibitor in the subject blood specimen is calculated on the basis of a calibration curve from the ratio or the difference between the first parameter and the second parameter.

[8] The method according to any one of [1] to [7], in which the coagulation factor is a blood coagulation factor VIII.

[9] The method according to any one of [1] to [8], in which the mixed specimen contains the subject blood specimen and the normal blood specimen at a volume ratio of 1:9 to 9:1.

[10] The method according to [9], further including diluting the subject blood specimen before mixing with the normal blood specimen, or diluting the mixed specimen prepared.

[11] The method according to any one of [1] to [10], in which the heating of the mixed specimen is performed at 30° C. or more and 40° C. or less for 2 to 30 minutes.

[12] The method according to any one of [1] to [11], in which the subject blood specimen is a blood specimen showing prolongation of APTT due to the presence of the coagulation factor inhibitor.

[13] The method according to any one of [1] to [12], in which a titer of the coagulation factor inhibitor is calculated in Bethesda units.

Advantageous Effects of the Invention

According to the present invention, the titer of a coagulation factor inhibitor can be measured in an extremely shorter time than that of a conventional method. Further, by the method according to the present invention, the inhibitor titer can be measured with a higher sensitivity than that of a conventional Bethesda assay. In addition, the method according to the present invention can be applied to an automatic analyzer that is used in a conventional blood coagulation test, and therefore, the labor required for the measurement can be greatly reduced.

BRIEF DESCRIPTION OF THE DRAWINGS

FIG. 12-2 shows A: a conceptual diagram for illustrating, for example, a weighted average point in a case where the calculation target area level is 10%, and B: a conceptual diagram for illustrating, for example, a weighted average point in a case where the calculation target area level is 80%.

FIG. 18E shows distributions of Pa, Pb, Pb/Pa, and Pb−Pa of vT10% for various specimens.

DETAILED DESCRIPTION OF THE INVENTION

One embodiment of the method according to the present invention will be described below with reference to drawings. The present embodiment relates to measurement of a titer of a coagulation factor inhibitor in a blood specimen, preferably a blood specimen showing a prolonged coagulation time, and more preferably a blood specimen showing a prolonged coagulation time due to the presence of a coagulation factor inhibitor.

1. Measurement Method

1.1. Overview of Method

In the method for measuring a titer of a coagulation factor inhibitor according to the present embodiment (hereinafter, also referred to as "the method according to the present invention"), a mixed specimen containing a subject blood specimen and a normal blood specimen is prepared, and then a coagulation reaction curve of each of heated and non-heated mixed specimens is acquired, and parameters related to the curve are calculated. Next, a titer of a coagulation factor inhibitor in the subject blood specimen is calculated on the basis of the ratio or difference between the parameters calculated from the heated and non-heated mixed specimens. Preferably, in the method according to the present invention, the titer of a coagulation factor inhibitor is calculated in Bethesda units (BU/mL).

Figure 1:
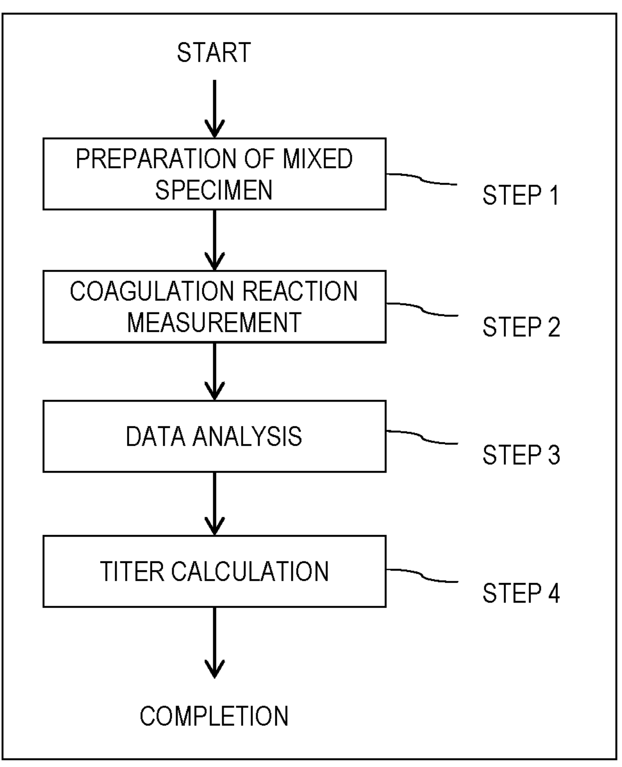
FIG. 1 illustrates one embodiment of a procedure for the method for measuring a titer of a coagulation factor inhibitor according to the present invention.

The overview of one embodiment of the method according to the present invention will be described with reference to the flowchart shown in FIG. 1. In the present method, at first, a mixed specimen containing a subject specimen is prepared (step 1), next, coagulation reaction measurement for each of the heated and non-heated mixed specimens is performed (step 2), and then the obtained measurement data are analyzed, and parameters related to the coagulation reaction curve of each of the heated and non-heated specimens are acquired (step 3). On the basis of the obtained parameters for the heated specimen and the non-heated specimen, the titer of a coagulation factor inhibitor of the subject specimen is calculated (step 4).

1.2. Specimen Preparation and Coagulation Reaction Measurement

Firstly, a blood specimen (hereinafter, also simply referred to as "specimen") is prepared (step 1). As the blood specimen, preferably a blood plasma is used. Into the specimen, a well-known anticoagulant agent that is usually used in a coagulation test can be added. For example, blood is collected with the use of a blood collection tube in which sodium citrate has been put, and then centrifuged, as a result of which blood plasma is obtained. In the method according to the present invention, a mixed specimen in which a blood specimen (subject blood specimen, or also simply referred to as "subject specimen") derived from a subject who is required to measure the titer of a coagulation factor inhibitor is mixed with a normal blood specimen (or also simply referred to as "normal specimen") at a predetermined volume ratio can be prepared.

Examples of the subject specimen include a blood specimen showing a prolonged APTT in a blood coagulation test, and preferably, a blood specimen showing a prolonged coagulation time (for example, APTT) due to the presence of a coagulation factor inhibitor. More preferably, the subject specimen is a specimen, which has been already confirmed by, for example, a cross-mixing test to show a prolonged coagulation time due to the presence of a coagulation factor inhibitor, and further of which the kind of the coagulation factor that is to be inhibited by the inhibitor is identified by a coagulation factor activity test.

Alternatively, the subject specimen may be a specimen, which has been confirmed to show a prolonged coagulation time (for example, APTT), however, of which the cause of the prolongation of the coagulation time is unknown. In the method according to the present invention, by the techniques to be described in 2.1 to 2.2 later, an APTT prolongation factor of the subject specimen (for example, whether or not the APTT prolongation is due to the presence of a coagulation factor inhibitor, or the kind of the coagulation factor that is inhibited by the inhibitor) can be determined. Accordingly, by performing the procedure for determining the APTT prolongation factor of the subject specimen prior to or in parallel with the procedure for measuring the titer, the titer of a coagulation factor inhibitor can be measured only by performing the coagulation reaction measurement (APTT measurement) to obtain a coagulation reaction curve and performing the analysis of the coagulation reaction curve, without performing, for example, the cross-mixing test in advance.

In the preparation of a mixed specimen, a subject specimen is mixed at a predetermined ratio with a normal specimen that has been prepared separately. The mixture ratio of the subject specimen to the normal specimen may be a ratio in a range of the subject specimen:the normal specimen=1:9 to 9:1, and is preferably in a range of 4:6 to 6:4, and more preferably 5:5, in a volume ratio when the total is taken as 10 volumes. In this regard, in a case where the titer of a coagulation factor inhibitor of the subject specimen is high, a mixed specimen may be prepared by diluting the subject specimen 2 to 100 times in advance before mixing with a normal specimen, and mixing the obtained diluted specimen with the normal specimen at the above-described volume ratio. For the dilution of the subject specimen, for example, a normal plasma, a buffer solution, or a FVIII-deficient plasma can be used. Alternatively, a diluted mixed specimen may be prepared by diluting a mixed specimen containing a subject specimen and a normal specimen at the above-described volume ratio with a normal specimen so that the final volume ratio of the subject specimen is around 1/2 to 1/100.

Some of the prepared mixed specimen is heated. The temperature of the heating may be, for example, 30° C. or more and 40° C. or less, and is preferably 35° C. or more and 39° C. or less, and more preferably 37° C. The time of the heating may be, for example, in a range of 2 to 30 minutes, and is preferably 5 to 30 minutes. The heating time may be longer, however, is preferably within 1 hour, and within 2 hours at most. In the present specification, the mixed specimen obtained by the above-described heating treatment, which is used in the method according to the present invention, is also referred to as "heated specimen". In addition, in the method according to the present invention, a mixed specimen that has not been subjected to the above-described heating treatment is also used, and such a mixed specimen is also referred to as "non-heated specimen" in the present specification. In this regard, the "non-heated specimen" may be subjected to a preliminary heating treatment of a specimen in an ordinary coagulation reaction measurement, for example, a heating at 30° C. or more and 40° C. or less for 1 minute or less, in that case, the "heated specimen" may be subjected to the preliminary heating treatment in addition to the above-described heating treatment.

In the method according to the present invention, coagulation reaction measurement for each of the heated specimen and non-heated mixed specimen is performed (step 2). Accordingly, in the method according to the present invention, among the prepared mixed specimens, some of the specimens may be subjected to the coagulation reaction measurement after the above-described heating treatment, and some of the specimens may be subjected to the coagulation reaction measurement without the heating treatment. The coagulation reaction measurement is specifically an APTT measurement. The order of the heated specimen and the non-heated specimen in the coagulation reaction measurement is not particularly limited. For example, some of the mixed specimens are heated, and then the coagulation reaction measurement of the heated specimen and the non-heated specimen may be performed, or the coagulation reaction measurement of the non-heated specimen is performed, and then the coagulation reaction measurement of the heated specimen may be performed.

The mixed specimen to be subjected to the coagulation reaction measurement is mixed with a reagent for measuring a coagulation time, and a specimen solution for coagulation reaction measurement is prepared. The reagent for measuring a coagulation time may be a reagent for APTT measurement, and examples of the reagent include a contact factor-based activator, and a phospholipid. Examples of the activator include ellagic acid, cerite, kaolin, silica, and a polyphenol compound. Examples of the phospholipid include phospholipids derived from an animal, a plant, and synthesis. Examples of the phospholipid derived from an animal include phospholipids derived from a rabbit brain, a chicken, and a pig. Examples of the phospholipid derived from a plant include phospholipids derived from soybeans. Further, a buffer solution such as Tris hydrochloric acid may be added to the specimen solution, as needed. Alternatively, as the reagent for the APTT measurement, a commercially available reagent for measuring APTT may be used. As an example of the commercially available reagent for measuring APTT, Coagpia APTT-N (manufactured by Sekisui Medical Co., Ltd.) is included. The prepared specimen solution is heated, and a contact factor in the solution is activated. The temperature of the heating is, for example, 30° C. or more and 40° C. or less, and preferably 35° C. or more and 39° C. or less.

After that, a calcium chloride solution (calcium ions) is added to the above-described specimen solution to initiate the blood coagulation reaction. The coagulation reaction of the solution after addition of the calcium chloride solution can be measured. In the measurement of the coagulation reaction, a common means, for example, an optical means for measuring an amount of scattered light, transmittance, absorbance, for example, or a mechanical means for measuring a viscosity of blood plasma may be used. The time to be measured can be around several tens of seconds to 5 minutes from the time point of the addition of the calcium chloride solution. During the period of measurement, the measurement can be repeated at predetermined intervals. The measurement may be performed, for example, at 0.1-second intervals. The temperature of the reaction mixture during the measurement is, for example, 30° C. or more and 40° C. or less, and preferably 35° C. or more and 39° C. or less. The reaction start time of the coagulation reaction can be typically defined as the time point when the calcium chloride solution is added to the specimen solution, however, other timings may be defined as the reaction start time. Further, various kinds of conditions for measurement can be appropriately set depending on, for example, the specimen, the reagent, or the measuring means.

A series of operations in the above-described coagulation reaction measurement may be performed by using an automatic analyzer. As one example of the automatic analyzer, a blood coagulation automatic analyzer, CP3000 (manufactured by Sekisui Medical Co., Ltd.) can be included. Alternatively, some of the operations may be performed manually. For example, the preparation of the specimen and the specimen solution for coagulation reaction measurement is performed by a person, and the subsequent operations can be performed by an automatic analyzer.

Figure 2:
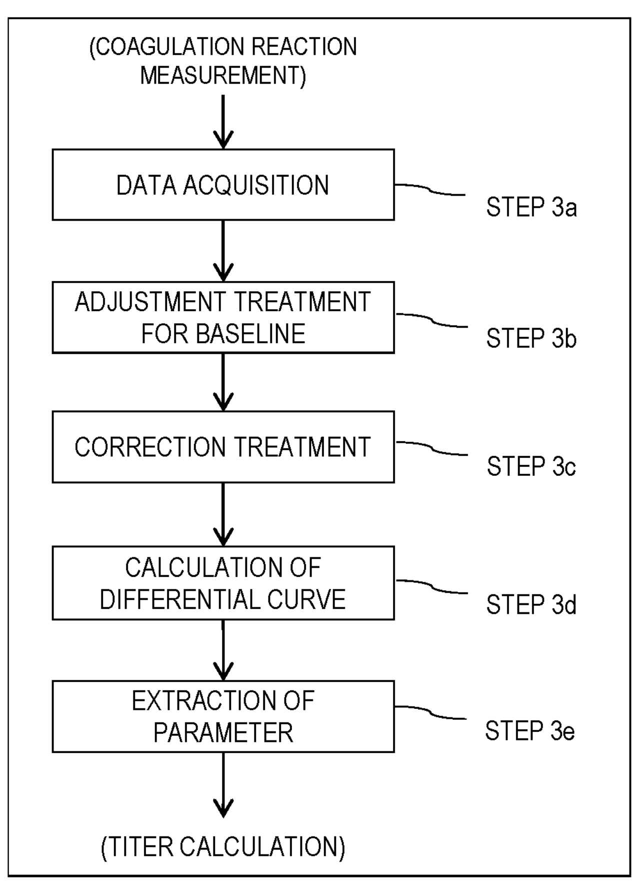
FIG. 2 illustrates one embodiment of a procedure for the step of data analysis shown in FIG. 1.

1.3. Data Analysis 1.3.1. Adjustment for Baseline and Correction Treatment of Data Next, a predetermined analysis is performed on the data obtained in the coagulation reaction measurement (step 3). The data analysis in step 3 will be described. One embodiment of the flow of the data analysis is shown in FIG. 2. The data analysis in step 3 may be performed in parallel with the coagulation reaction measurement in step 2, or may be performed later by using the data of the coagulation reaction measurement performed in advance. The data analysis in step 3 is performed for each of the heated specimen and non-heated specimen. The procedure for the following steps 3a to 3e is basically common in the heated specimen and the non-heated specimen.

In step 3a, the measurement data in the coagulation reaction measurement are acquired. The data are data that reflect, for example, the coagulation reaction process of a specimen, obtained by the APTT measurement in step 2 described above. For example, data indicating the time change of the degree of progress of the coagulation reaction (for example, amount of scattered light) after addition of a calcium chloride solution, of a reaction mixture containing a specimen and a reagent for measuring a coagulation time are acquired. The data obtained in the coagulation reaction measurement are also referred to as coagulation reaction information in the present specification.

Figure 3:
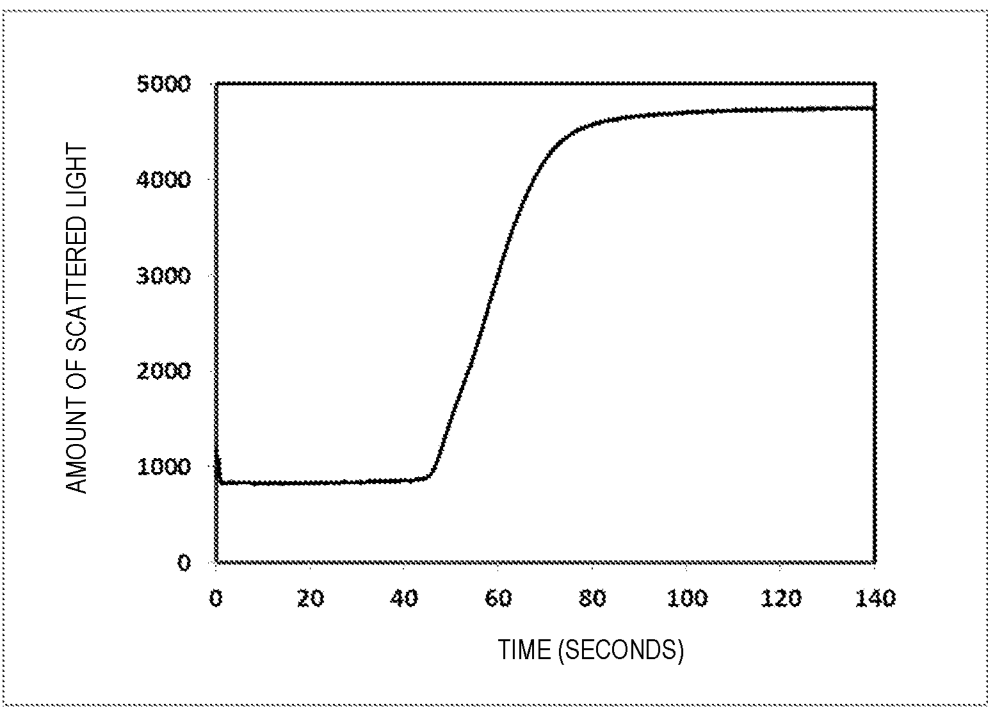
FIG. 3 shows one example of a coagulation reaction curve.

One example of the coagulation reaction information acquired in step 3a is shown in FIG. 3. FIG. 3 is a coagulation reaction curve based on the amount of scattered light, and the horizontal axis represents the elapsed time (coagulation reaction time) after addition of a calcium chloride solution, and the vertical axis represents the amount of scattered light. The coagulation reaction of a specimen proceeds with the lapse of time, so that the amount of scattered light is increased. In the present specification, a curve showing the changes in the coagulation reaction amount with respect to the coagulation reaction time indicated by, for example, such an amount of scattered light is referred to as a coagulation reaction curve.

The coagulation reaction curve based on the amount of scattered light, as shown in FIG. 3, is usually sigmoid. On the other hand, the coagulation reaction curve based on the amount of transmitted light is usually reverse sigmoid. Hereinafter, in the present specification, data analysis using the coagulation reaction curve based on the amount of scattered light will be described as the coagulation reaction information. It is obvious for a person skilled in the art that similar treatment can be performed also in a case of the data analysis using a coagulation reaction curve based on the amount of transmitted light or the absorbance as the coagulation reaction information. Alternatively, as the coagulation reaction information, the coagulation reaction curve obtained by a mechanical means such as a viscosity change of a mixture may be subjected to the analysis.

Figure 4:
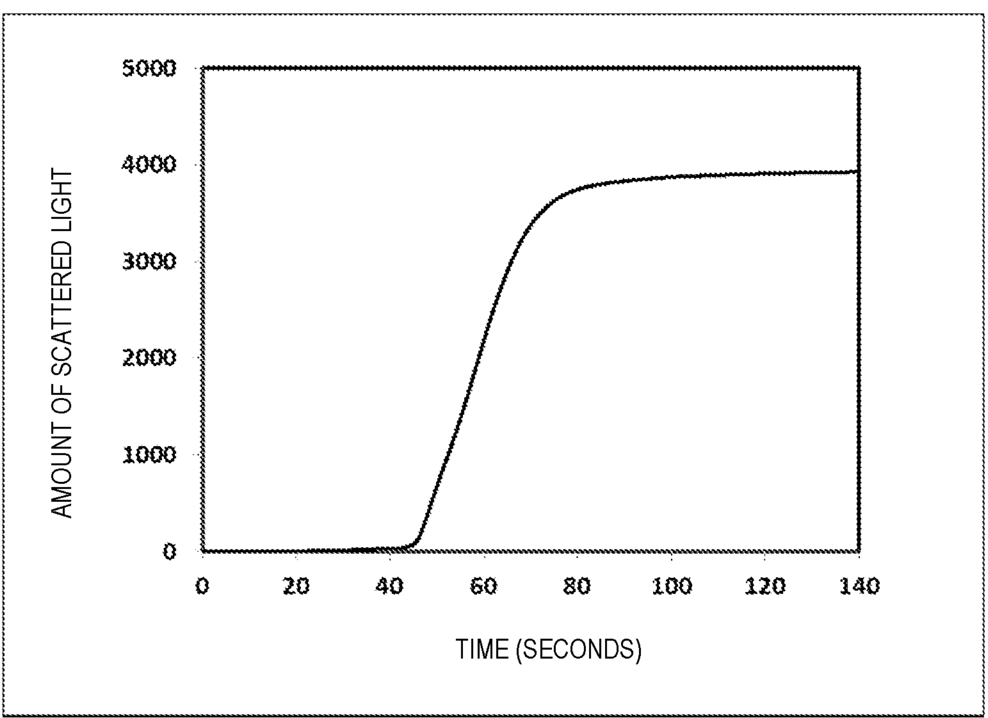
FIG. 4 shows one example of a coagulation reaction curve after adjustment for baseline.
Figure 5:
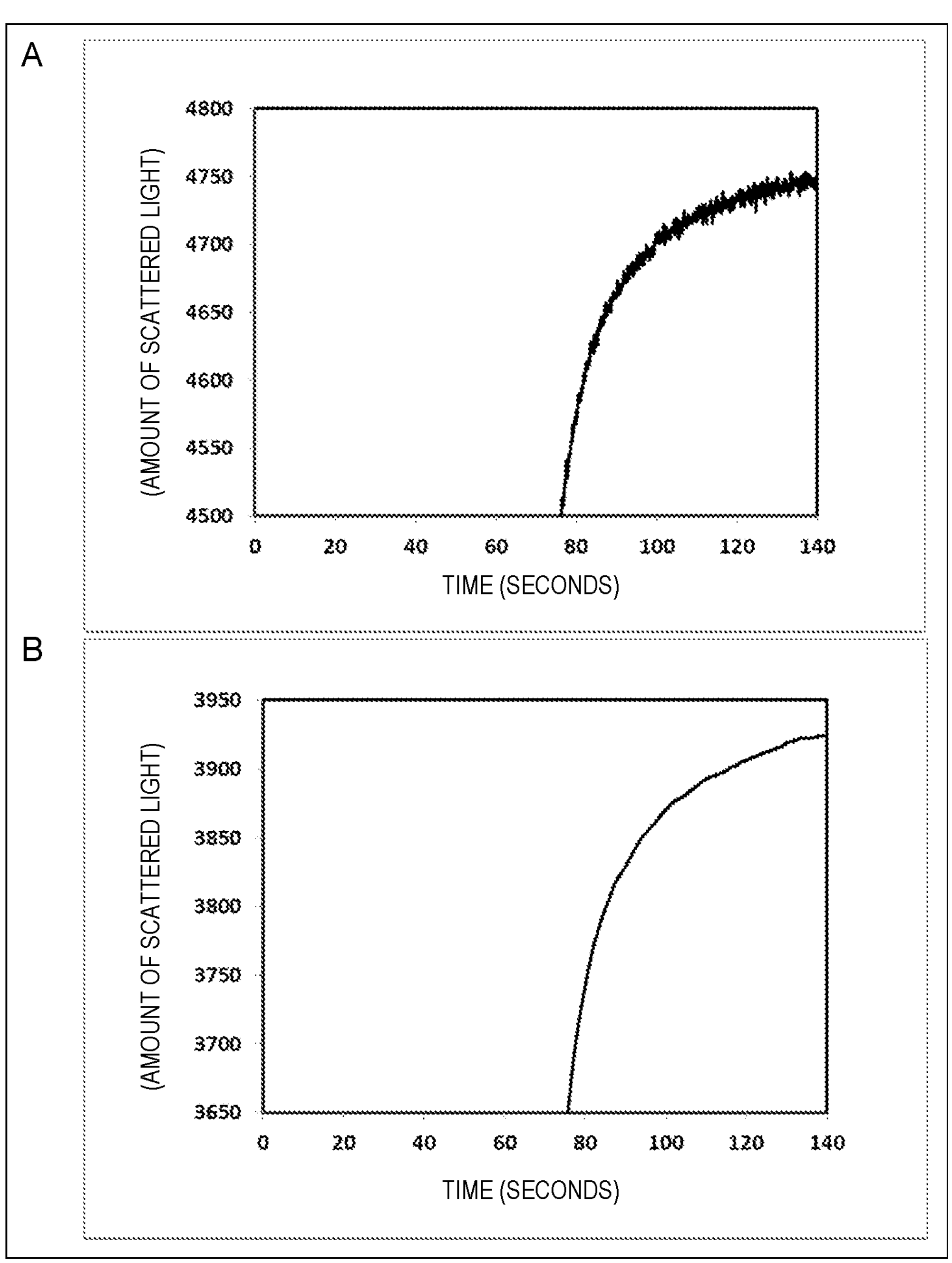
FIG. 5 shows A: a partially enlarged diagram of one example of a coagulation reaction curve, and B: a partially enlarged diagram of one example of a coagulation reaction curve after adjustment for baseline.

In step 3b, adjustment for baseline of the coagulation reaction curve is performed. The adjustment for baseline includes a smoothing treatment for removing noise, and a zero point adjustment. FIG. 4 shows one example of the coagulation reaction curve of FIG. 3, for which the adjustment for baseline (smoothing treatment and zero point adjustment) has been performed. Any known noise removal method can be used for the smoothing treatment. Further, as shown in FIG. 3, since a reaction mixture containing a specimen originally scatters light, the amount of scattered light at the starting point of the measurement (time 0) is larger than 0. With the zero point adjustment after the smoothing treatment, the amount of scattered light at time 0 is adjusted to 0 as shown in FIG. 4. FIGS. 5A and 5B show partially enlarged diagrams of the coagulation reaction curve of FIG. 3 before and after the adjustment for baseline, respectively. In FIG. 5B, the smoothing treatment and the zero point adjustment are performed on the data of FIG. 5A.

The height of the coagulation reaction curve depends on the fibrinogen concentration of a specimen. On the other hand, since the fibrinogen concentration varies among individuals, the height of the coagulation reaction curve differs depending on the specimen. Accordingly, in the present method, a correction treatment for converting the coagulation reaction curve after the adjustment for baseline into relative values is performed in step 3c, as needed. With the correction treatment, a coagulation reaction curve that does not depend on the fibrinogen concentration can be obtained, and as a result of which the difference in the shape of the coagulation reaction curve after adjustment for baseline can be quantitatively compared among specimens.

In one embodiment, the coagulation reaction curve after adjustment for baseline is corrected so that the maximum value is a predetermined value in the correction treatment. Suitably, in the correction treatment, a corrected coagulation reaction curve P(t) is determined from the coagulation reaction curve after the adjustment for baseline in accordance with the following formula (1). In the formula (1), D(t) represents the coagulation reaction curve after adjustment for baseline, Dmax and Dmin represent the maximum value and minimum value of D(t), respectively, Drange represents the range of change (that is, Dmax−Dmin) of D(t), and A represents the maximum value of the corrected coagulation reaction curve.

$$P(t)=[(D(t)-D\min)/D\mathrm{range}]\times A \quad (1)$$

Figure 6:
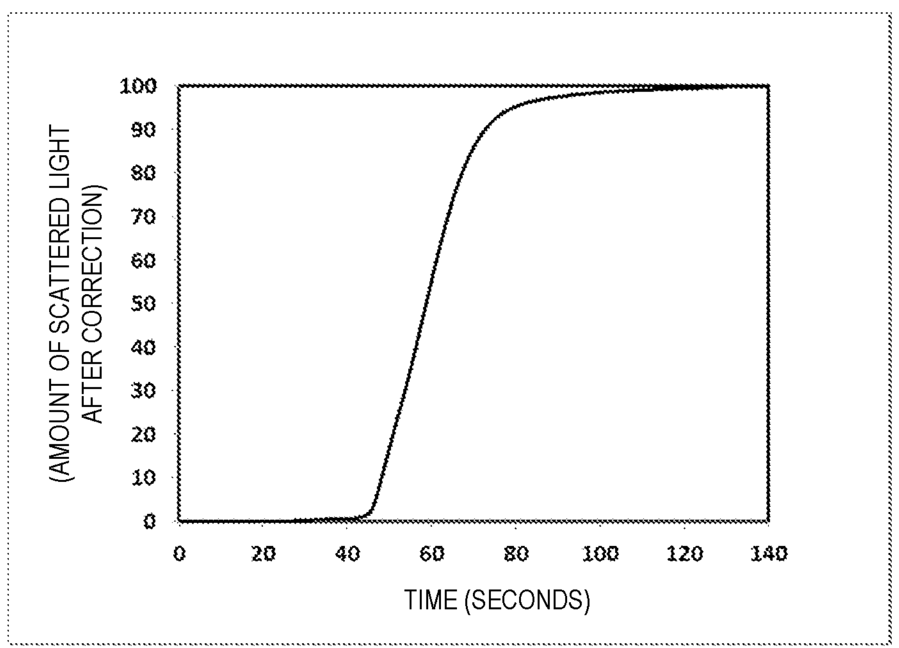
FIG. 6 shows one example of a coagulation reaction curve after correction treatment.

As one example, FIG. 6 shows the data corrected so that the coagulation reaction curve shown in FIG. 4 has a maximum value of 100. In this regard, in FIG. 6, the values have been corrected so as to be from 0 to 100 after the correction, however, may also be other values (for example, from 0 to 10000, that is, A=10000 in the formula (1)). In addition, the correction treatment may not be necessarily performed.

Alternatively, the correction treatment as described above may be performed on a waveform related to the coagulation rate to be described later, or on a parameter group extracted from the waveform. That is, the waveform related to the coagulation rate for the coagulation reaction curve D(t) after adjustment for baseline, to which the correction treatment is not performed, is calculated, and then this can be converted into values corresponding to P(t). Alternatively, a parameter group is extracted from the waveform related to the coagulation rate, and then values of individual parameters included in the parameter group can be converted into the values corresponding to P(t).

1.3.2. Calculation of Waveform Related to Coagulation Rate

In step 3d, a differential curve obtained by differentiating the coagulation reaction curve is calculated. In the present specification, examples of the differential curve include a primary differential curve obtained by differentiating the coagulation reaction curve (with or without the correction treatment described above) once, and a secondary differential curve obtained by differentiating the coagulation reaction curve twice (or differentiating the primary differential curve once). The primary differential curve includes an uncorrected primary differential curve (coagulation rate curve), and a corrected primary differential curve. The coagulation rate curve represents the values obtained by differentiating the coagulation reaction curve (without correction treatment) once, that is, the rate (coagulation rate) of the change in the coagulation reaction amount in an arbitrary coagulation reaction time. The corrected primary differential curve represents the values obtained by differentiating the coagulation reaction curve (with correction treatment) once, that is, the relative rate of the change in the coagulation reaction amount in an arbitrary coagulation reaction time (which may be referred to as coagulation progress rate in the present specification). Accordingly, the primary differential curve can be a waveform representing the coagulation rate or the relative value of the coagulation rate, in the coagulation reaction of a specimen.

The secondary differential curve can be obtained by differentiating the coagulation reaction curve (with or without the correction treatment) twice. The secondary differential curve derived from the coagulation reaction curve (without correction treatment) is also referred to as coagulation acceleration curve, and the value for the time indicates the coagulation acceleration. The secondary differential curve derived from the coagulation reaction curve (with correction treatment) is also referred to as corrected secondary differential curve, and represents the time rate of change in the coagulation progress rate.

In addition, in the present specification, a coagulation reaction curve with the correction treatment and a coagulation reaction curve without the correction treatment are also referred to as a corrected zero-order curve and an uncorrected zero-order curve, respectively, and further these are also collectively referred to as "zero-order curve". Further, in the present specification, primary differential curves of the corrected zero-order curve and the uncorrected zero-order curve are also referred to as a corrected primary curve and an uncorrected primary curve, respectively, and further these are also collectively referred to as "primary curve". Furthermore, in the present specification, twice differential curves of the corrected zero-order curve and the uncorrected zero-order curve, or once differential curves of the corrected primary curve and the uncorrected primary curve are also referred to as a corrected secondary curve and an uncorrected secondary curve, respectively, and further these are also collectively referred to as "secondary curve".

Further, in the present specification, regardless of with or without correction treatment of the coagulation reaction curve from which to be derived, the values representing the progress of coagulation by the primary curve is also collectively referred to as primary differential values. In addition, in the present specification, regardless of with or without correction treatment of the coagulation reaction curve from which to be derived, the values representing the rate of change of the primary differential values by the secondary curve is also collectively referred to as secondary differential values.

Figure 7:
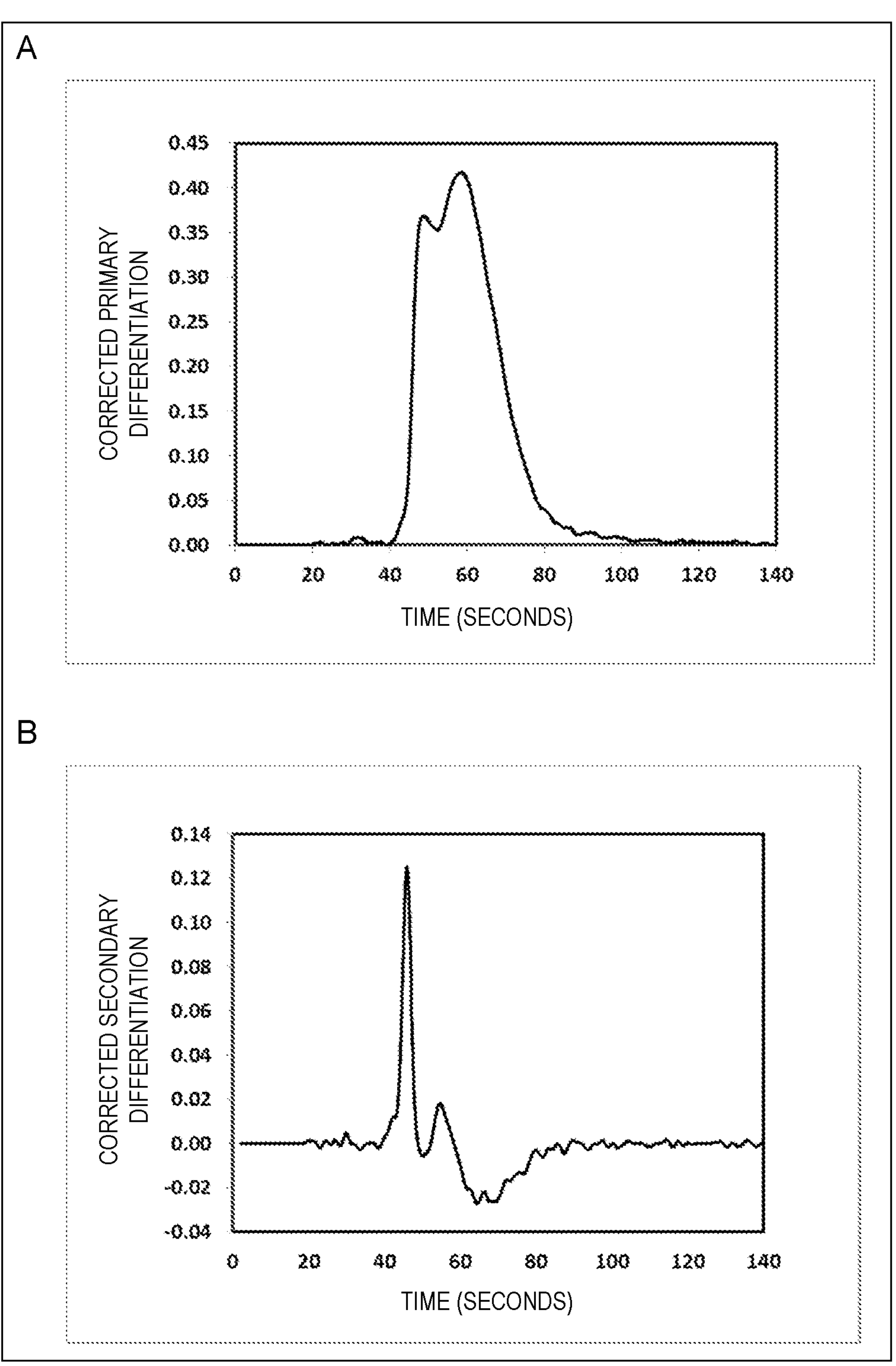
FIG. 7 shows A: one example of a corrected primary curve, and B: one example of a corrected secondary curve.

The zero-order curve and the primary curve can be differentiated by using a known technique. FIG. 7A shows a corrected primary curve obtained by differentiating once the corrected zero-order curve shown in FIG. 6. In FIG. 7A, the horizontal axis represents the coagulation reaction time, and the vertical axis represents the primary differential value. FIG. 7B shows a corrected secondary curve obtained by differentiating once the corrected primary curve shown in FIG. 7A. In FIG. 7B, the horizontal axis represents the coagulation reaction time, and the vertical axis represents the secondary differential value.

1.3.3. Extraction of Parameters

In step 3e, parameters that characterize the above-described zero-order curve, primary curve, or secondary curve are extracted. The parameters are parameters related to the coagulation reaction curve of a specimen. In the method according to the present invention, in the extraction step of parameters from the primary curve or secondary curve, one or more predetermined areas are extracted from the curve, and in addition, for each of the one or more predetermined areas, parameters that characterize the predetermined area are extracted. As a result, for each of the one or more predetermined areas, one or more parameters that characterize the predetermined area can be extracted. More specifically, the parameters from the primary curve or secondary curve are parameters related to a weighted average point in a predetermined area of the primary curve or secondary curve of a specimen. Hereinafter, the parameters will be described by referring to the procedure for extracting the parameters from a primary curve.

1.3.3.1. Extraction of Calculation Target Area

In parameter extraction, at first, one or more predetermined areas are extracted from a primary curve. Hereinafter, the predetermined area used for the parameter extraction is also referred to as a calculation target area. The calculation target area is an area (segment) in which the primary differential value (y value) of a primary curve is a predetermined calculation target area level or more. In other words, the calculation target area is an area (segment) in which the primary differential value (y value) of a primary curve is a predetermined calculation target area level or more and a maximum value or less.

Figure 8:
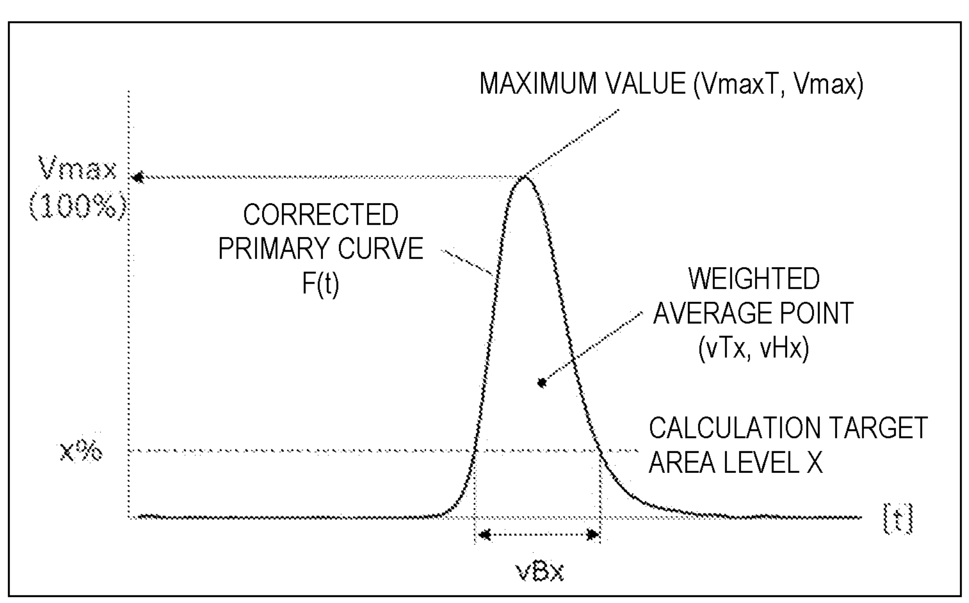
FIG. 8 shows a conceptual diagram of parameters calculated from a primary curve.

The calculation target area will be described with reference to FIG. 8. FIG. 8 shows a corrected primary curve F(t) at a time t. Further, FIG. 8 shows a maximum value Vmax of the primary differential value, coordinates vTx and vHx representing the position of the weighted average point (black circle) in the calculation target area at a calculation target area level X (x % when Vmax is taken as 100%), and vBx representing the peak width, which are parameters described below. In FIG. 8, the corrected primary curve has been taken as an example, however, similar parameters can be calculated also for the uncorrected primary curve.

The calculation target area level is a predetermined value that specifies the lower limit of the primary differential value in the calculation target area, and is also referred to as a calculation target area level X in the present specification. That is, the calculation target area is an area in which the primary differential value in a primary curve (corrected primary differential value in FIG. 8) is the calculation target area level X or more and Vmax or less (that is, F(t)≥X). The calculation target area level X can be set to limit the range that reflects a peak shape of the primary curve. As the calculation target area level X is increased, the influence of the shape of an upper part of the peak of the primary curve relatively more largely reflects on the analysis results.

In the method according to the present invention, one or more calculation target areas may be extracted. The number of the calculation target areas extracted in the method according to the present invention is not necessarily limited. In a case where multiple calculation target areas are extracted, the multiple calculation target areas are different areas.

1.3.3.2. Weighted Average Point

The weighted average point in a calculation target area will be described with reference to FIG. 8. For a primary curve (corrected primary curve in FIG. 8) F(t) (F(t)=primary differential value, and t=time), the position corresponding to the “weighted average value” when the values of the calculation target area level or more of F(t) are set as the data to be calculated is calculated as the weighted average point (vT, vH). In the present specification, in order to identify the weighted average point that is derived from different calculation target areas, the weighted average point may be referred to as (vTx, vHx), in accordance with the calculation target area level X (where X=Vmax×x %) from which they are derived. For example, the weighted average point in the calculation target area when X is 5% of Vmax is (vT5%, vH5%).

The time (t) indicating a weighted average point is defined as the weighted average time vT in a primary curve. That is, the weighted average time vT is a time from the coagulation reaction start time to the weighted average point. The primary differential value indicating a weighted average point is defined as the weighted average height vH in a primary curve. That is, the weighted average time vT and the weighted average height vH are coordinates of the weighted average point in a primary curve as shown in FIG. 8.

More specifically, the weighted average time vT and weighted average height vH can be obtained by the following procedure. First, when the maximum value of F(t) is denoted by Vmax and the calculation target area level is denoted by x % of Vmax, the times t [t1, . . . , t2] (t1<t2) that satisfy F(t)≥Vmax×x×0.01 are determined, and the product sum value M is determined by the following formula (2).

$$M = \sum_{i=t1}^{t2} (i \times F(i)) \tag{2}$$

The weighted average time vT and the weighted average height vH are calculated by the following formulas (3) and (4), respectively. The weighted average point is led from the obtained vT and vH.

$$vT = \frac{M}{\sum_{i=t1}^{t2} F(i)} \tag{3}$$

$$vH = \frac{M}{\sum_{i=t1}^{t2} i} \tag{4}$$

In the above description, the weighted average point in the calculation target area of a corrected primary curve is calculated with reference to FIG. 8, and also in a case of a uncorrected primary curve, similarly, the weighted average point in the calculation target area, the weighted average time vT and the weighted average height vH can be defined. These weighted average time VT and weighted average height vH can be used as parameters that characterize the calculation target area. In the present specification, in order to identify vT and vH that are derived from different calculation target areas, the VT and vH may be referred to as vTx and vHx, respectively, in accordance with the calculation target area level X (where X=Vmax×x %) from which they are derived. For example, the VT and vH in the calculation target area of which X is 5% of Vmax are vT5% and vH5%, respectively.

Figure 9:
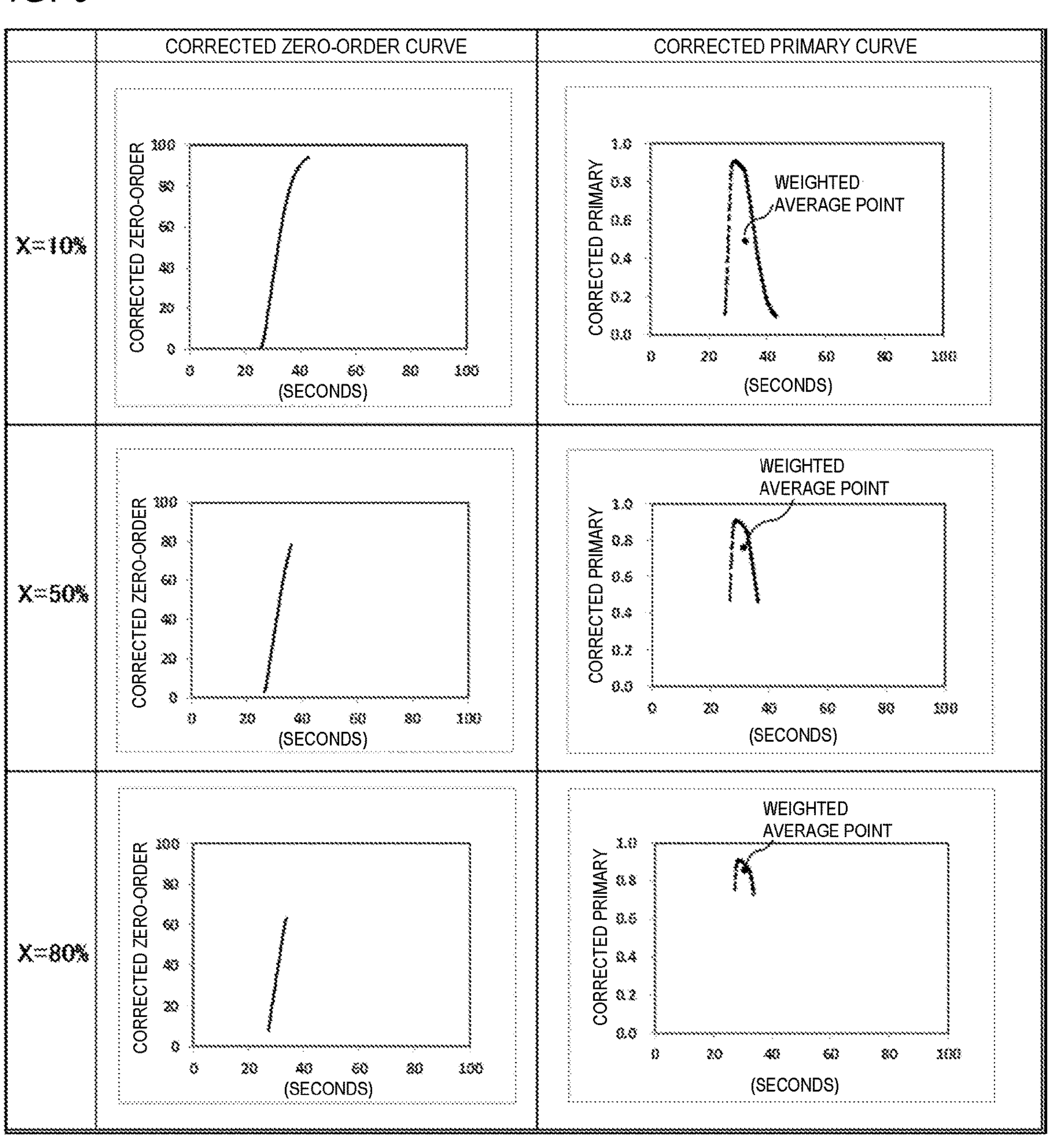
FIG. 9 shows a conceptual diagram for illustrating a calculation target area level, ranges of the corrected zero-order and corrected primary curves to be analyzed, and a weighted average point.

FIG. 9 shows the relationship among the calculation target area level X, the areas (calculation target areas) of the corrected zero-order curve (left) and corrected primary curve (right) to be analyzed at that time, and the weighted average point. In FIG. 9, the upper part, the middle part, and the lower part show the cases where the calculation target area levels X are 10%, 50%, and 80% of Vmax (=100%), respectively. The solid lines indicate the corrected zero-order curves, the dotted lines indicate the calculation target areas of the corrected primary curves, and the black circles indicate the weighted average points. As the calculation target area level X changes, the calculation target area and the position of the weighted average point change as shown in FIG. 9.

Figure 10:
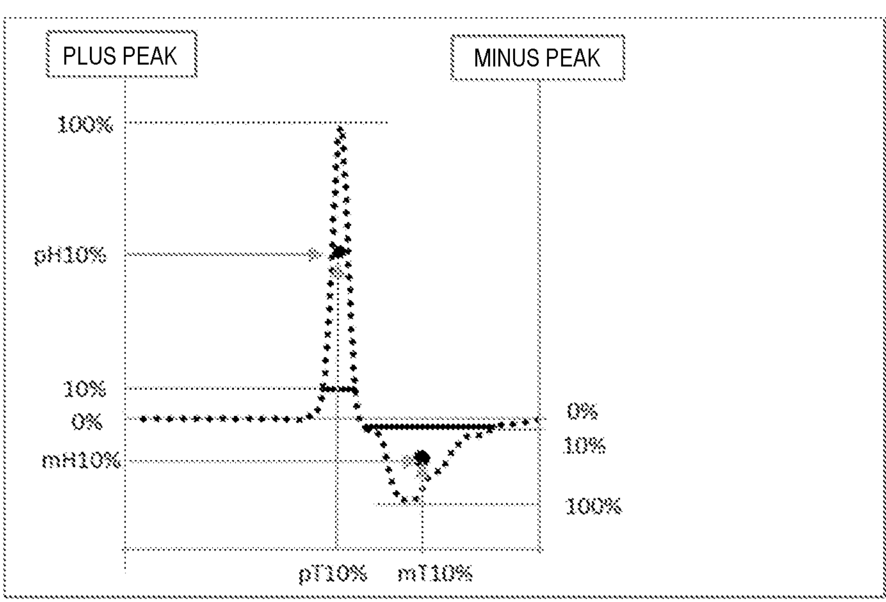
FIG. 10 shows a conceptual diagram of parameters calculated from a secondary curve.

Similarly, also for the secondary curve, the weighted average point, the weighted average time, and the weighted average height can be defined. The secondary curve has peaks in both of the plus and minus directions of the secondary differential value as shown in FIG. 10. For this reason, the weighted average point of the secondary curve can be calculated for both of the plus and minus peaks. For example, for the plus peak, when the maximum value of the secondary curve A=F' (t) is denoted by Amax and the calculation target area level is denoted by x % of Amax, the times t [t1, . . . , t2] (t1<t2) that satisfy F' (t)≥Amax×x×0.01 are determined, and the weighted average time pT and weighted average height pH of the plus peak are calculated in accordance with the following formulas (2)' to (4)'. For the minus peak, when the minimum value of the secondary curve A=F' (t) is denoted by Amin and the calculation target area level is denoted by x % of Amin, the times t [t1, . . . , t2] (t1<t2) that satisfy F' (t)≤Amin×x×0.01 are determined, and the weighted average time mT and weighted average height mH of the minus peak are calculated in accordance with the above formulas (2)', (3)", and (4)". As the calculation target area level X changes, the position of the weighted average point changes.

$$M = \sum_{i=t1}^{t2} (i \times F'(i)) \tag{2'}$$

$$pT = \frac{M}{\sum_{i=t1}^{t2} F'(i)} \tag{3'}$$

$$pH = \frac{M}{\sum_{i=t1}^{t2} i} \tag{4'}$$

$$mT = \frac{M}{\sum_{i=t1}^{t2} F'(i)} \tag{3''}$$

$$mH = \frac{M}{\sum_{i=t1}^{t2} i} \tag{4''}$$

1.3.3.3. Peak Width, Flattening, and Time Rate

The minimum value (t1) and maximum value (t2) of the times t [t1, . . . , t2] that satisfy F(t)≥X described above represent the minimum value and maximum value of the coagulation reaction time in the calculation target area of a primary curve, and the minimum value (t1) and the maximum value (t2) may be referred to as an area start point time vTs and an area end point time vTe (vTs<vTe), respectively. During the time from vTs to vTe, the length of time at which F(t)≥X (value obtained by multiplying the value obtained by subtracting 1 from the number of data points to be F(t)≥X by the photometric time interval) is defined as the peak width vB of the primary curve. More specifically, in a case where the vTs and vTe when the calculation target area level is x % of Vmax are represented by vTsx and vTex, respectively, the peak width vBx is from vTsx to vTex (including the vTsx and the vTex).

Figure 11:
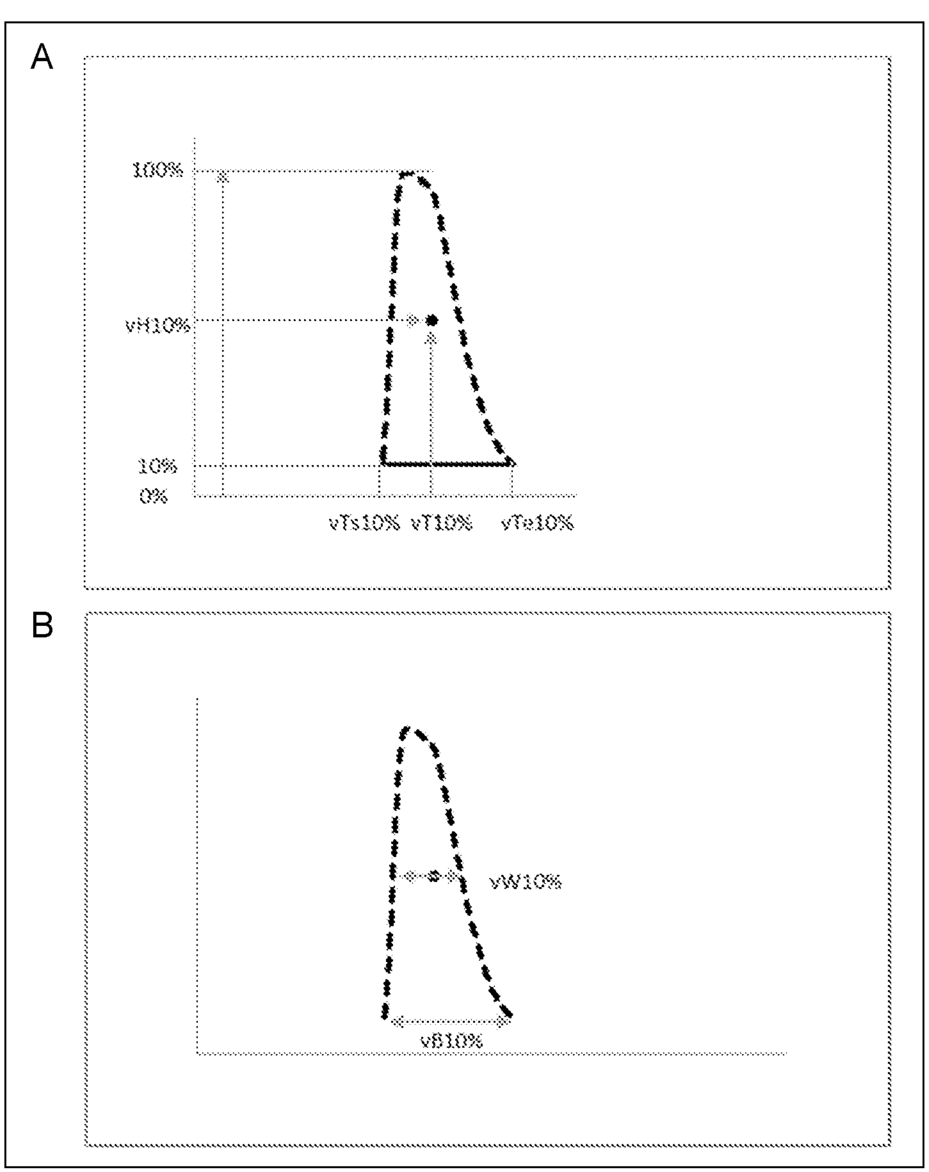
FIG. 11 shows conceptual diagrams for indicating a weighted average point, vTs, vTe, vB, and vW. The dotted line indicates a 10% calculation target area of a primary curve.

As another example of the parameters used in the present invention, a weighted average peak width vW can be included. The vW is a peak width (length of time to be F(t)≥vH during the time from the minimum time to the maximum time at which F(t)≥vH is satisfied) at which the primary curve F(t)≥vH is satisfied. As shown in FIG. 11, the vW is a peak width at the weighted average point, at which the primary curve F(t)≥vH is satisfied. As another example of the parameters used in the present invention, vTr can be included. The vTr is a width from vTs to vTe. The vTr is usually the same value as vB, however, in a case where the shape of the curve has bimodal peaks and further the calculation target area level X is higher than the valley bottom of the bimodal peaks, vB<vTr is obtained. FIG. 11 shows diagrams of a calculation target area (dotted line) of the primary curve when the calculation target area level X is 10% of Vmax. A weighted average point (vT, vH) (black circle), vTs, and vTe are shown in FIG. 11A, and vB and vW are shown in FIG. 11B.

Similarly, for the plus peak of a secondary curve, the minimum and maximum values of the times that satisfy F'(t)≥X are pTs and pTe, respectively, and during the time from pTs to pTe, the length of time at which F'(t)≥X is satisfied (value obtained by multiplying the value obtained by subtracting 1 from the number of data points to be F' (t)≥X by the photometric time interval) is defined as the peak width pB, and the length of time at which F' (t)≥pH is satisfied is defined as the weighted average peak width pW. For the minus peak of a secondary curve, the minimum and maximum values of the times that satisfy F'(t)<X is satisfied are mTs and mTe, respectively, and during the time from mTs to mTe, the length of time at which F'(t)≤X is satisfied (value obtained by multiplying the value obtained by subtracting 1 from the number of data points to be F' (t)≤X by the photometric time interval) is defined as the peak width mB, and the length of time at which F' (t)≤mH is satisfied is defined as the weighted average peak width mW.

Figure 12:
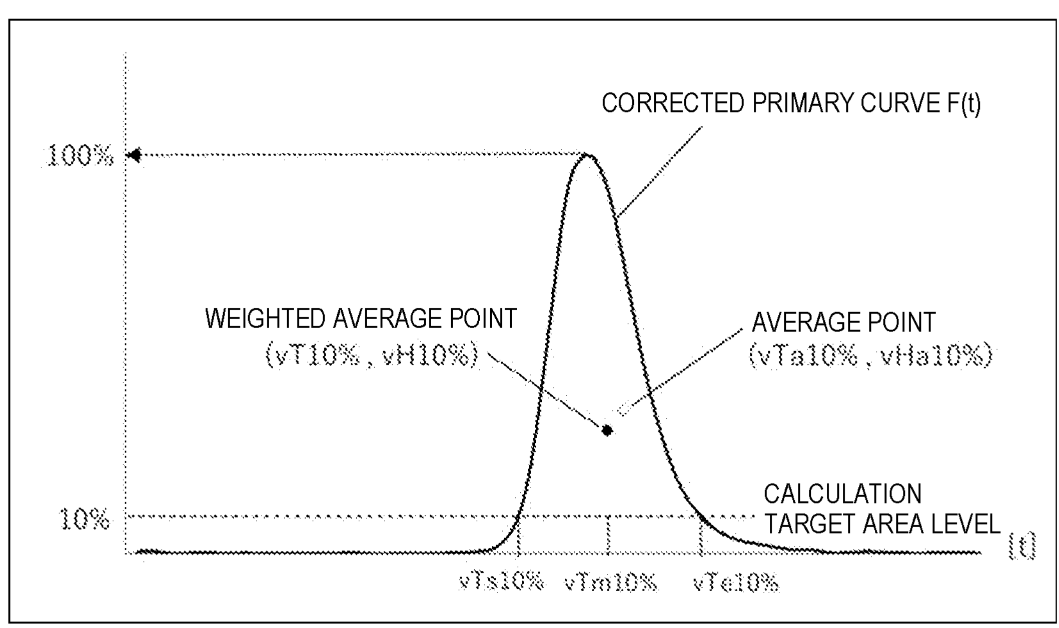
FIG. 12 shows a conceptual diagram for indicating vTa, vHa, and vTm.
Figures 2, 12:
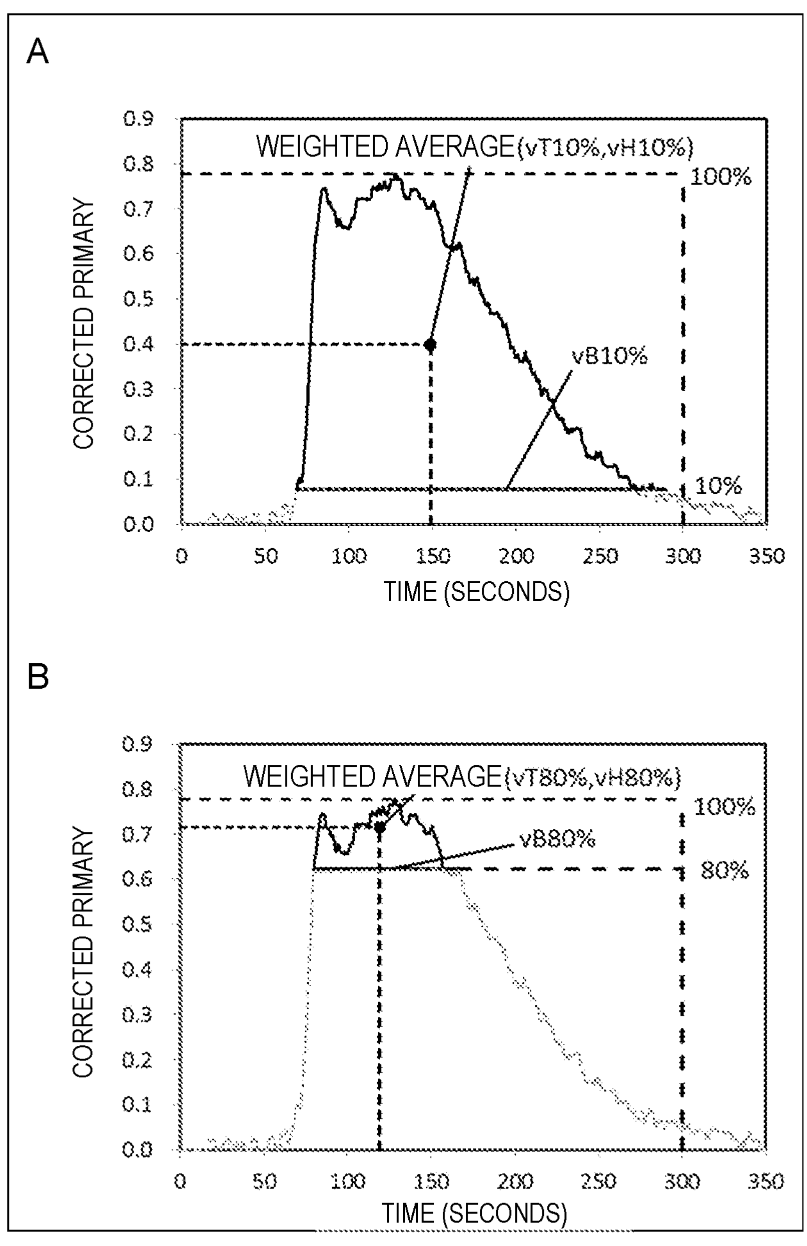

Other examples of the parameters used in the present invention include an average time vTa, an average height vHa, and an area median time vTm. FIG. 12 shows an average point (vTa, vHa) (white rhombus), a weighted average point (vT, vH) (black circle), vTs, vTe, and vTm of the primary curve when the calculation target area level X is 10% of Vmax. The vTa, vHa, and vTm are represented by the following formulas, respectively when the number of data points from F(vTs) to F(vTe) is denoted by n.

$$vTa = \frac{\sum_{i=vTs}^{vTe} i}{n} \tag{5}$$

$$vHa = \frac{\sum_{i=vTs}^{vTe} F(i)}{n} \tag{6}$$

$$vTm = \frac{vTs + vTe}{2} \tag{7}$$

Further examples of the parameters used in the present invention include flattenings (B flattenings) vAB and vABa based on the peak width of a primary curve, and flattenings (W flattenings) vAW and vAWa based on the weighted average peak width. In one embodiment, as shown in the following formulas, the vAB is defined as the ratio of the weighted average height vH to the peak width vB, and the vAW is defined as the ratio of the weighted average height vH to the weighted average peak width vW. The vABa is defined as the ratio of the average height vHa to the peak width vB, and the vAWa is defined as the ratio of the average height vHa to the weighted average peak width vW.

$$vAB = vH/vB \tag{8a}$$

$$vAW = vH/vW \tag{8b}$$

$$vABa = vHa/vB \tag{8c}$$

$$vAWa = vHa/vW \tag{8d}$$

Further examples of the parameters used in the present invention include a time rate (B time rate) vTB based on the peak width of a primary curve, and a time rate (W time rate) vTW based on the weighted average peak width. In one embodiment, as shown in the following formulas, the vTB is defined as the ratio of the weighted average time vT to the peak width vB, and the vTW is defined as the ratio of the weighted average time VT to the weighted average peak width vW.

$$vTB=VT/vB \tag{9a}$$

$$vTW=vT/vW \tag{9b}$$

In this regard, the flattenings may be vAB=vB/vH or vAW=vW/VH, or may also be vABa=vB/vHa or vAWa=vW/vHa. Similarly, the time rates may be vTB=vB/vT, or vTW=vW/vT. Further, these ratios may be multiplied by a constant K. That is, for example, the flattening may be vAB=(vH/vB) K, vAB=(vB/vH) K, vAW=(vH/vW) K, or vAW=(vW/vH)K (K is a constant), or may also be vABa=(vHa/vB)K, vABa=(vB/vHa)K, vAWa=(vHa/vW)K, or vAWa=(vW/vHa)K, and the time rate may be vTB=(vT/vB) K, vTB=(vB/vT)K, vTW=(vT/vW)K, or vTW=(vW/vT)K (K is a constant).

The peak widths vB, pB, and mB, the weighted average peak widths vW, pW, and mW, the average time vTa, the average height vHa, the area start point time vTs, the area end point time vTe, the area median time vTm, the flattenings vAB, vAW, vABa, and vAWa, and the time rates vTB, and vTW, which are as described above, can be parameters that characterize the calculation target area. In the present specification, in order to identify parameters that are derived from different calculation target areas, the parameters may be referred to as, for example, vBx, vABx, vTBx, respectively, in accordance with the calculation target area level X (where X=Vmax×x %) from which they are derived. At this time, for example, the vABx and vTBx are calculated from the vBx and the vHx or vTx. For example, vB, vW, vTa, vHa, vTs, vTe, vTm, vAB, vAW, vABa, vAWa, vTB, and vTW in the calculation target area in which X is 5% of Vmax is vB5%, vW5%, vTa5%, vHa5%, vTs5%, vTe5%, vTm5%, vAB5%, vAW5%, vABa5%, vAWa5%, vTB5%, and vTW5%, respectively. Further, pB, mB, pW, and mW in the calculation target area in which X is 5% of Amax or Amin is pB5%, mB5%, pW5%, and mW5%, respectively.

FIGS. 12-2A and 12-2B show vH, vT, and vB for different calculation target area levels X based on the same primary curve. FIG. 12-2A shows the case where the calculation target area level X is 10% of Vmax, and FIG. 12-2B shows the case where the calculation target area level X is 80% of Vmax. In both cases, the Vmax is 100%.

Similarly, also for the secondary curve, the flattening and the time rate can be determined on the basis of the peak width or the weighted average peak width, and these can be used as the parameters in the present invention.

1.3.3.4. Area Under the Curve (AUC)

As another example of the parameters used in the present invention, the area under the curve (AUC) in the calculation target area of the primary or secondary curve can be included. Since the secondary curve has a plus-side peak and a minus-side peak, as the area under the curve (AUC) in the calculation target area in which the maximum peak height of the secondary curve is 100%, there may be an AUC (pAUC) in the calculation target area for the plus-side peak, and an AUC (mAUC) in the calculation target area of the minus-side peak (in this regard, in a case of mAUC, the area is accurately an area above the curve). In the present specification, in order to identify the AUCs that are derived from different calculation target areas, the AUC may be referred to as AUCx, in accordance with the calculation target area level X (where X=Vmax×x %) from which it is derived. For example, the vAUC, pAUC, and mAUC in the calculation target area when X is 5% of Vmax, Amax, and Amin are vAUC5%, pAUC5%, and mAUC5%, respectively.

1.3.3.5. Others

Parameters other than the parameters related to the above-described weighted average point may be included in the parameters related to the coagulation reaction curve used in the present invention. Further examples of the parameters include a maximum primary differential value Vmax, a maximum secondary differential value Amax, a minimum secondary differential value Amin, and VmaxT, AmaxT, and AminT that represent the times to reach the Vmax, the Amax, and the Amin, respectively. Further, when the amount of scattered light at the time point when the amount of change in the amount of scattered light in a zero-order curve satisfies predetermined conditions is taken as 100%, the reaction elapsed time at which the amount of scattered light reaches an amount corresponding to c % can be included as the coagulation time Tc in the parameters used in the present invention. The c may be any value, and for example, Tc is T50.

As in the above, the parameters related to a coagulation reaction curve have been described on the basis of the coagulation reaction curve based on the amount of scattered light. In addition, it is obvious for a person skilled in the art that equivalent parameters can be acquired from the coagulation reaction curve based on other coagulation measuring means (for example, amount of transmitted light, or absorbance). For example, in the primary curve F(t) obtained from a coagulation reaction curve that is reverse sigmoid as based on the amount of transmitted light, the positive and negative are reversed for the curve based on the above-described amount of scattered light. In such a case, it is obvious for a person skilled in the art that the signs of F(t) are reversed in the parameter calculation, for example, the maximum value Vmax is replaced with the minimum value Vmin, the calculation target area is an area that satisfies F(t)≤X, vB and vW are lengths of time to be F(t)≤X and F(t)≤vH, respectively from t1 to t2.

2. Measurement of Titer of Coagulation Factor Inhibitor Using Parameters Related to Coagulation Reaction Curve By the procedure described above, parameters related to a coagulation reaction curve of a mixed specimen are acquired. The values of the parameters can change depending on the shape of the coagulation reaction curve. In a mixed specimen containing normal plasma and a subject specimen having abnormal coagulation, the shape of the coagulation reaction curve may be different in some cases depending on the cause of the abnormal coagulation or the influence of heating. Accordingly, the parameters obtained from the heated specimen and the parameters obtained from the non-heated specimen may have different values depending on the cause of the abnormal coagulation in some cases. In this regard, in the present specification, in a case of describing the value of parameter, for example, the ratio or difference, the "parameter" and the "parameter value" are used synonymously with each other. In addition, in a case of describing the kind of parameter, the "parameter" and the "parameter kind" are used synonymously with each other.

In the method according to the present invention, at least one kind selected from the group consisting of the parameters related to the coagulation reaction curve (preferably parameters shown in Table 1 to be shown later) is acquired for each of the heated specimen and the non-heated specimen. The parameter obtained from the non-heated specimen is referred to as a first parameter, and the parameter obtained from the heated specimen is referred to as a second parameter. In the method according to the present invention, a titer of a coagulation factor inhibitor in the subject specimen contained in a mixed specimen is calculated on the basis of the ratio or the difference between the first parameter and the second parameter (step 4).

In one embodiment of the method according to the present invention, it is already determined that the subject specimen contained in a mixed specimen is a blood specimen showing a prolonged APTT due to the presence of a specific coagulation factor inhibitor, by a cross-mixing test, for example. In this case, in accordance with the procedure of 2.3 to be described later, a titer of a coagulation factor inhibitor can be calculated on the basis of the first and second parameters. In another embodiment of the method according to the present invention, it is unknown whether or not the subject specimen contained in a mixed specimen shows a prolonged APTT due to the presence of a specific coagulation factor inhibitor. In this case, in the method according to the present invention, in accordance with the procedures of 2.1 to 2.2 to be described later, determination of the APTT prolongation factor, and differentiation of the coagulation factor inhibitor can be performed. After that, in accordance with the procedure of 2.3 to be described later, a titer of a coagulation factor inhibitor can be calculated on the basis of the first and second parameters. In the latter embodiment, since there is no need to perform the time-consuming cross-mixing test, the measurement of a titer of a coagulation factor inhibitor can be realized more easily.

2.1 Determination of APTT Prolongation Factor

Figure 13:
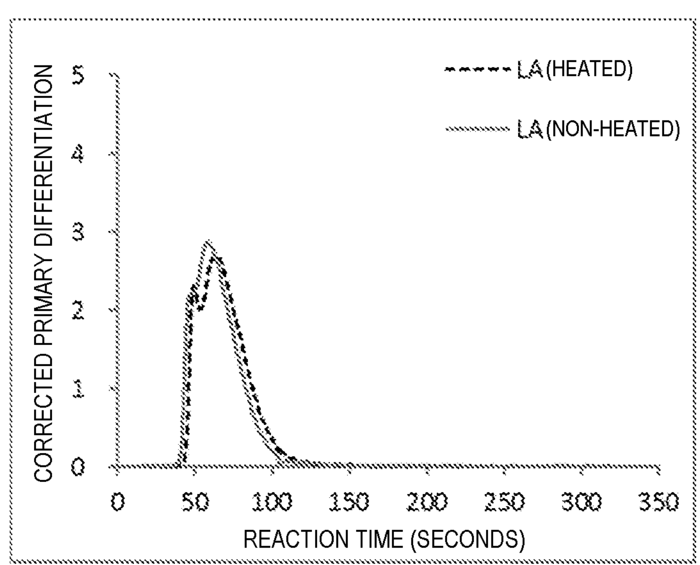
FIG. 13 shows corrected primary curves of heated and non-heated LA specimens.
Figure 14:
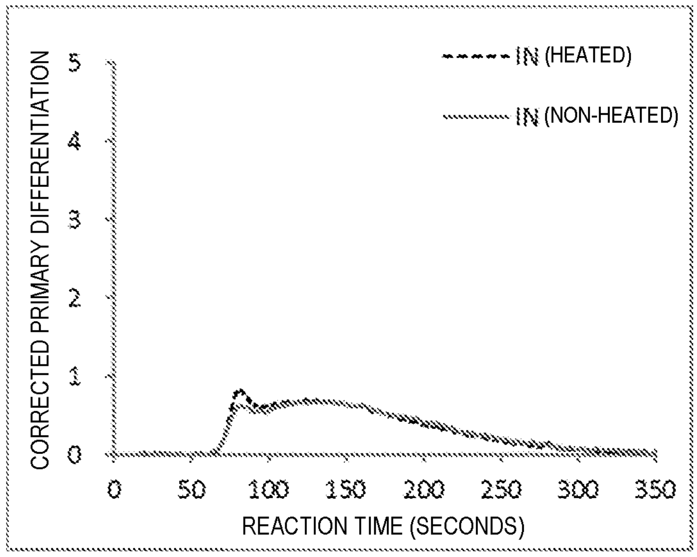
FIG. 14 shows corrected primary curves of heated and non-heated FVIII inhibitor-positive specimens.
Figure 15:
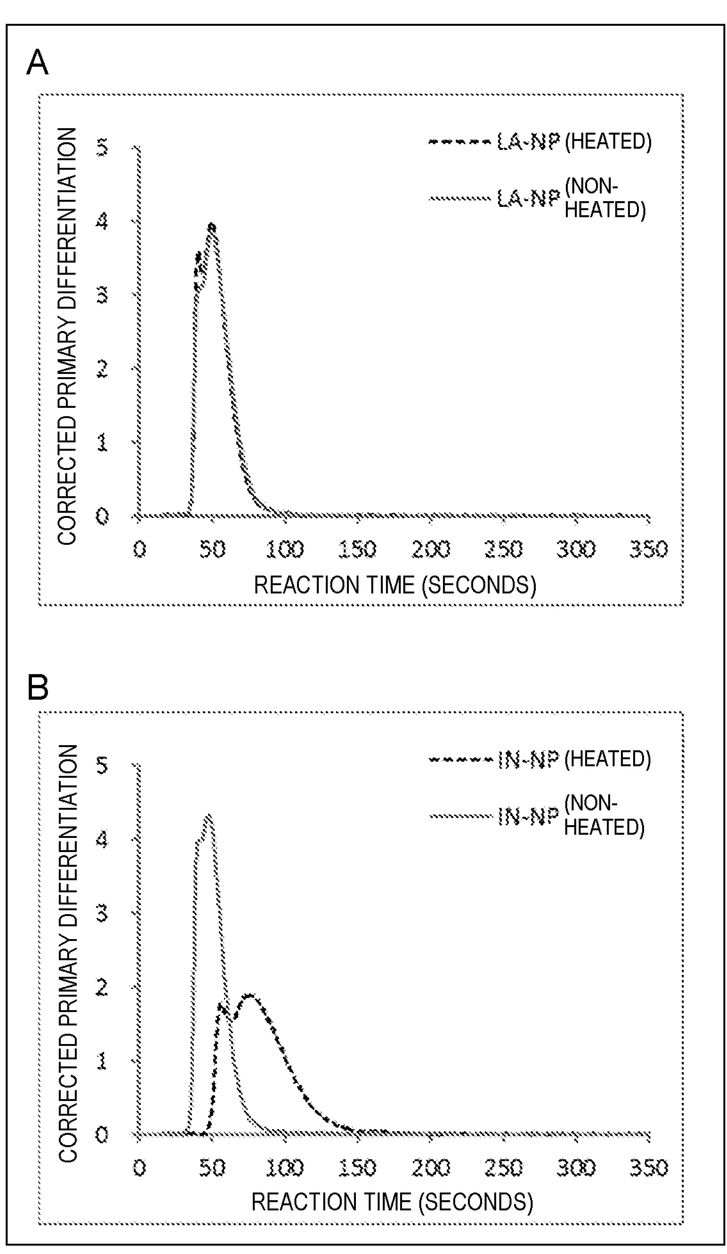
FIG. 15 shows corrected primary curves of heated specimen and non-heated specimen. A: a mixed specimen (LA-NP) of a LA-positive specimen and a normal specimen, and B: a mixed specimen (IN-NP) of a FVIII inhibitor-positive specimen and a normal specimen.

As described above, a component causing abnormal coagulation, contained in a specimen, or heating of the specimen may affect the shape of a coagulation reaction curve. Examples of the cause of abnormal coagulation or the change of a coagulation reaction curve due to heating are shown with reference to FIGS. 13 to 15. FIG. 13 shows corrected primary curves of heated and non-heated LA plasmas (LA). FIG. 14 shows corrected primary curves of heated and non-heated FVIII inhibitor positive plasmas (IN). FIG. 15A shows corrected primary curves of heated and non-heated mixed plasmas (LA-NP) of a LA plasma (LA) and a normal plasma at 1:1. FIG. 15B shows corrected primary curves of heated and non-heated mixed plasmas (IN-NP) of a FVIII inhibitor positive plasma (IN) and a normal plasma at 1:1.

As shown in FIG. 13, in the LA plasma (LA), there was almost no change in the shape of the curve due to the heating. Further, as shown in FIG. 14, in the FVIII inhibitor positive plasma (IN), there was almost no change in the shape of the curve due to the heating similarly as in the LA.

As shown in FIG. 15A, in the mixed plasma (LA-NP) of a LA plasma (LA) and a normal plasma at 1:1, the peak appears earlier (coagulation time is shortened) and the shape is sharper than those in FIG. 13 by the mixture of LA with a normal plasma. In the LA-NP, there was almost no change in the shape of the curve due to the heating similarly as in the LA.

As shown in FIG. 15B, in the mixed plasma (IN-NP) of a FVIII inhibitor-positive plasma (IN) and a normal plasma at 1:1, the peak appears earlier and the shape is sharper than those in FIG. 14 in the non-heated specimen by the mixture of IN with a normal plasma, similarly as in the LA-NP. On the other hand, the peak appears late, the peak height is lower, and further the peak width is wider in the heated specimen. It is determined that this shape change is due to the inhibited coagulation reaction of the mixed plasma because of the progress of the antigen-antibody reaction of the inhibitor (anti-FVIII antibody) contained in the IN with the FVIII contained in the normal plasma during the heating treatment. A possibility that the IN is differentiated from the LA by indexing the shape change between the non-heated and the heated as the change in the parameter has been confirmed.

As shown in FIG. 15, the fact that the coagulation reaction curve of the mixed specimen can be changed due to the component causing abnormal coagulation or the heating means that a subject specimen showing a prolonged APTT due to the presence of a coagulation factor inhibitor can be detected by analyzing the parameters related to the coagulation reaction curves of the non-heated specimen and heated specimen. The evaluation of the APTT prolongation factor based on the parameters is shown in Table 2 to be shown later. In Table 2, for a normal specimen (NP), a LA-positive specimen (LA), a mixed specimen of a LA-positive specimen and a normal specimen at 1:1 (LA-NP (mix)), a FVIII inhibitor-positive specimen (IN), and a mixed specimen of a FVIII-inhibitor positive specimen and a normal specimen at 1:1 (IN-NP (mix)), first parameters (Pa) acquired from a coagulation reaction curve of a non-heated specimen, second parameters (Pb) acquired from a coagulation reaction curve of a heated specimen heated for 10 minutes, and ratios (Pb/Pa) of such parameters are shown.

Among the parameters shown in Table 2, APTT represents a reaction elapsed time (T50 (seconds)) at which the amount of scattered light of a baseline-adjusted coagulation reaction curve reaches 50%, Vmax represents a maximum value of a corrected primary curve, and VmaxT represents a time to reach the Vmax from the start of photometry. Further, in Table 2, parameters related to the weighted average point at a calculation target area level of 10%, vH10%, vT10%, vB10%, vAB10%, and vTB10% are shown.

As shown in Table 2, in the normal specimen (NP) that is not affected by heating, the ratios (Pb/Pa) are values close to 1 in all of the parameters. As shown in FIG. 15A, in the mixed specimen (LA-NP(mix)) of a LA-positive specimen (LA) and a normal specimen, since the coagulation reaction is not so affected by heating, the ratio (Pb/Pa) is a value close to 1.

On the other hand, as shown in FIG. 15B, the coagulation reaction of the mixed specimen (IN-NP(mix)) containing a FVIII inhibitor-positive specimen is greatly affected by heating, and which is reflected in the parameter ratios (Pb/Pa). As shown in Table 2, in the IN-NP(mix), the ratios (Pb/Pa) are remarkably large in APTT, VmaxT, vT, and vB, and are small in Vmax, and vH. These parameters can be indexes for detecting a FVIII inhibitor-positive specimen. Further, as shown in Table 2, the ratio (Pb/Pa) of vAB shows a remarkable decrease from 1 in the IN-NP(mix), and the behavior clearly different from that in the LA or NP is shown. In addition, in FIG. 18 to be shown later, it has been shown that for APTT, Vmax, Amax, vB10%, vT10%, vAB10%, and vTB10%, the ratios (Pb/Pa) thereof show values increased or decreased from 1 in the mixed specimen containing a FVIII inhibitor-positive specimen, however, show values close to 1 in the mixed specimen containing LA, NP, or coagulation factor deficiency (such as hemophilia A or hemophilia B), and the differences (Pb−Pa) thereof show values deviated significantly from 0 in the mixed specimen containing a FVIII inhibitor-positive specimen, however, show values close to 0 in the mixed specimen containing LA, NP, or coagulation factor deficiency.

As described above, in the FVIII inhibitor-positive specimen, the first parameter from a non-heated specimen is different from the second parameter from a heated specimen, and further an influence of heating on such parameter values is not observed in the normal specimen or the LA-positive specimen. Accordingly, it can be determined whether or not the subject specimen contained in a mixed specimen is FVIII inhibitor-positive, on the basis of the above-described parameters acquired from the heated specimen and the non-heated specimen. Preferably, a FVIII inhibitor-positive specimen can be detected on the basis of the indexes that can reflect the rate of change and the range of change in the values of the first parameters and second parameters, for example, the ratio between the first parameter and the second parameter as shown in Table 2, or the difference between the first parameter and the second parameter.

As described above, by using the first parameter and the second parameter, the procedure for determining a blood specimen showing a prolonged APTT due to the presence of a FVIII inhibitor has been described. By the similar procedure, another coagulation factor (for example, FIX) inhibitor-positive specimen can be distinguished from a LA-positive specimen.

2.2 Differentiation of Coagulation Factor Inhibitor

In a case where a blood specimen showing a prolonged APTT due to the presence of a coagulation factor inhibitor is detected by the procedure in 2.1 above, and in a case where the kind of the coagulation factor inhibitor is unknown, it is necessary to determine the kind. As such coagulation factor inhibitors, a FVIII inhibitor, a FIX inhibitor, and inhibitors of other factors are known in descending order of the number of occurrences.

Figure 16:
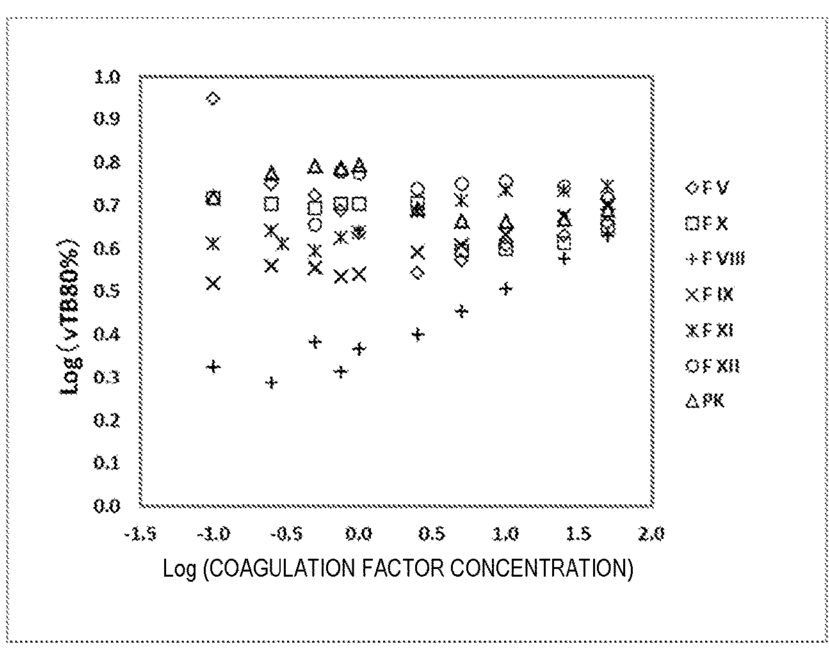
FIG. 16 shows one example of changes in parameter values due to the concentration of various coagulation factors.

FIG. 16 shows the relationship between the concentrations of various coagulation factors and vTB80%. In this regard, the concentration of coagulation factor is a logarithmic value, and the concentration of 0.1% or less is logarithmically transformed to 0.1%. In vTB80% of a factor concentration of 10% or less, among the various coagulation factors at the same concentration, the value of FVIII is clearly lower than the values of other coagulation factors, so that the FVIII deficiency can be distinguished from other coagulation factor deficiencies. As a result, it can be determined that the kind of inhibitor is a FVIII inhibitor from the value of vTB80%.

Figure 17:
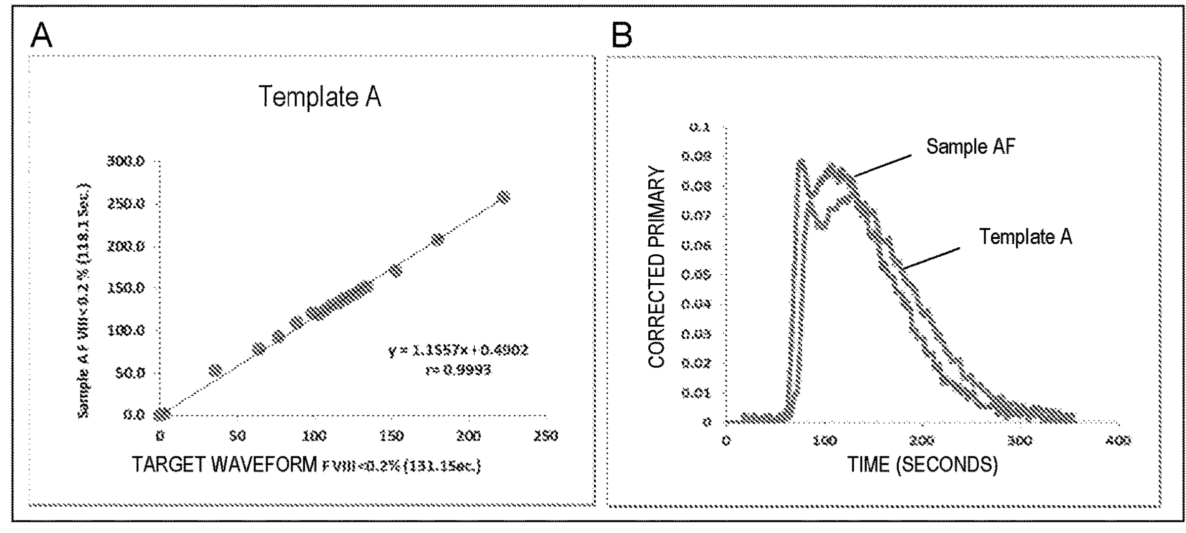
FIG. 17 shows A: a regression line for a parameter group, and B: corrected primary curves of the subject specimen and the reference. Sample AF: subject specimen, and Template A: reference.

In another one embodiment, by template matching using the above-described parameters of the present invention, the kind and concentration of the deficient coagulation factor are evaluated. More specifically, when the above-described parameters are acquired, multiple calculation target areas are set, the weighted average point of each of the calculation target areas are determined, and the parameters that characterize the calculation target area, such as VT, vH, vB, vAB, and vTB are acquired. As to these parameters, any one kind may be acquired for each of the calculation target areas, and preferably two or more kinds are acquired. The number of the calculation target areas is not particularly limited, and is preferably 3 to 100 areas, and more preferably 5 to 20 areas. Further, values such as Vmax, VmaxT, Amax, and AmaxT may be acquired. In addition, specimens (reference) each having a known coagulation factor concentration and a variously different concentration are prepared, and the parameters for each of the specimens are acquired similarly. At this time, the calculation target areas to be set and kinds of the parameters to be acquired for the reference specimen are arranged so as to correspond to those of the subject specimen. Next, a linear regression equation between the parameter group obtained for the subject specimen and the parameter group of each of the reference specimens is determined, and the correlation (for example, tilt, intercept, correlation coefficient, or determination coefficient) of the regression line is determined. The concentration of the coagulation factor in the reference having the highest correlation with the subject specimen is estimated as the concentration of the coagulation factor in the subject specimen. An example of a linear regression equation between the subject specimen and the reference is shown in FIG. 17. FIG. 17A shows the regression line between the parameter groups of a subject specimen (Sample AF) and a reference (Template A), both of which have a FVIII activity of less than 0.2%. As the parameter group, a parameter group consisting of 50 parameters of (vB [vB5%, vB10%, . . . , and vB90%], vT [vT5%, vT10%, . . . , and vT90%], vH [vH5%, vH10%, . . . , and vH90%], vAB [vAB5%, vAB10%, . . . , and vAB90%], and vTB [vTB5%, vTB10%, . . . , and vTB90%]) for 10 calculation target areas (X=5%, 10%, 20%, 30%, 40%, 50%, 60%, 70%, 80%, and 90%, to the Vmax) is used. FIG. 17B shows corrected primary curves of the subject specimen (Sample AF) and the reference (Template A) of FIG. 17A. The two primary curves have shapes extremely similar to each other, and which indicates that the degree of approximation of the blood coagulation characteristics reflects on the correlation between the parameter groups of both specimens.

Alternatively, in accordance with a conventional technique, it can be determined whether or not the prolongation of APTT of the subject specimen is due to the presence of a coagulation factor inhibitor, and the kind of the coagulation factor inhibitor can be determined, by a cross-mixing test, or a coagulation factor activity test.

2.3 Calculation of Titer of Coagulation Factor Inhibitor

As described in 2.1 above, the shape of the coagulation reaction curve for a mixed specimen containing a subject specimen showing a prolonged APTT due to the coagulation factor inhibitor changes by heating. Further, the degree of the change in the shape of the coagulation reaction curve depends on the activity (titer) of the coagulation factor inhibitor. Accordingly, a titer of the coagulation factor inhibitor in the subject blood specimen can be calculated on the basis of the ratio or the difference between the first parameter and the second parameter, from the non-heated specimen and the heated specimen.

More specifically, the ratio or the difference between the first parameter and the second parameter is determined, and then from the determined values, a titer of the coagulation factor inhibitor is calculated on the basis of the calibration curve. The calibration curve can be created in advance. For example, for a series of standard specimens each having a known titer of a specific coagulation factor inhibitor and a variously different titer, the first parameter and the second parameter are calculated by a similar procedure as in the case of the subject specimen described above, and then a calibration curve may be created by using the inhibitor titers, and the ratio or the difference between the first parameter to the second parameter, of the standard specimens.

Examples of the preferred parameters used for measurement of titer by the method according to the present invention include Vmax, vT, vH, vB, vAB, vTB, vAW, vTW, pAUC, and mAUC. The calculation target area level X for using these parameters is preferably 5 to 90%, and more preferably 30 to 70% when the Vmax is 100%.

The kind of the coagulation factor inhibitor to be subjected to the titer measurement in the method according to the present invention is not particularly limited, and examples of the kind include a FVIII inhibitor, and a FIX inhibitor, and preferably a FVIII inhibitor. By creating a calibration curve in advance for a target coagulation factor inhibitor to be subjected to titer measurement, the titer of the target coagulation factor inhibitor can be calculated on the basis of the ratio or the difference between the first parameter and the second parameter, of a mixed specimen.

EXAMPLES

Hereinafter, the present invention will be described in more detail by way of Examples, however, the present invention is not limited to the following Examples.

Unless otherwise specified, the parameters used in the following Examples represent parameters derived from corrected zero-order to secondary curves. In addition, the parameters derived from uncorrected zero-order to secondary curves are represented by adding R to the beginning of the name of each parameter. For example, when the weighted average height of a corrected primary curve is vH, the weighted average height of the uncorrected primary curve is represented by RvH, and when the weighted average time of a corrected primary curve is vT, the weighted average time of the uncorrected primary curve is represented by RvT. A list of parameters is shown in the following Table 1. In the following description, there may be a case where the B flattening, W flattening, B time rate, and W time rate of combination waveform parameters are expressed so that the calculation content of the parameters with a coefficient k omitted can be understood.

TABLE 1

| Waveform parameter of coagulation reaction curve (zero-order curve) | | | | |
|---|---|---|---|---|
| | | Time to reach c % height when the maximum height of the zero-order curve is 100% | | |
| Reaction time | Tc | Primary curve | Secondary curve (plus peak) | Secondary curve (minus peak) |
| **Waveform parameters of primary curve and secondary curve** | | | | |
| Peak width (time) | Bx | vBx | pBx | mBx |
| Weighted average height | Hx | vHx | pHx | mHx |
| Weighted average time | Tx | vTx | pTx | mTx |
| Weighted average peak width | Wx | vWx | pWx | mWx |
| Average height | Hax | vHax | — | — |
| Average time | Tax | vTax | — | — |
| Area under the curve | AUCx | vAUCx | pAUCx | mAUCx |
| Area start-point time | Tsx | vTsx | — | — |
| Area end-point time | Tex | vTex | — | — |
| Area median time | Tmx | vTmx | — | — |
| Peak width (time) | Trx | vTrx | — | — |
| Maximum primary differential value | | Vmax (vH100%) | — | — |
| Maximum primary differential value time | | VmaxT (vT100%) | — | — |
| Maximum/minimum secondary differential value | | — | Amax (pH100%) | Amin (mH100%) |
| Maximum/minimum secondary differential value time | | — | AmaxT (pT100%) | AminT (mT100%) |
| **Combination waveform parameters** | | | | |
| B flattening | (Hx/Bx)*k | VABX | pABx | mABx |
| W flattening | (Hx/Wx)*k | vAWx | pAWx | mAWx |
| B flattening | (Hax/Bx)*k | vABax | — | — |
| W flattening | (Hax/Wx)*k | vAWax | — | — |
| B time rate | (Tx/Bx)*k | vTBx | pTBx | mTBx |
| W time rate | (Tx/Wx)*k | vTWx | pTWx | mTWx |

x: Calculation target area level (% to Vmax), k: Constant

Parameter derived from the coagulation reaction curve without correction treatment has "R" in the beginning of the name.

Reference Example 1

1) Subject Specimen

The subject specimens used in Examples are shown below. As the normal plasma (NP), a citric acid-added plasma obtained from a healthy subject was used. As the LA plasma (LA), a positive lupus anticoagulant plasma available from George King Biomedical, Inc. was used. As the factor VIII-deficient plasma (HA) and the factor IX-deficient plasma (HB), a factor VIII deficient and a factor IX deficient both available from George King Biomedical, Inc. were used. As the factor VIII (FVIII) inhibitor-positive plasma (InL, InM, or InH), a factor VIII deficient with inhibitor available from George King Biomedical, Inc. was used.

| Group No . | Kind of specimen | The number of specimens |
|---|---|---|
| 1 | Normal plasma (NP) | 23 |
| 2 | LA plasma (LA) | 6 |
| 3 | Hemophilia A (HA) | 14 |
| 4 | Hemophilia B (HB) | 12 |
| 5 | Low-titer FVIII inhibitor plasma (InL) | 12 |

-continued

| Group No. | Kind of specimen | The number of specimens |
|---|---|---|
| 6 | Median-titer FVIII inhibitor plasma (InM) | 35 |
| 7 | High-titer FVIII inhibitor plasma (InH) | 8 |
| | Specimen for calibration curve (Cal) | 7 |

In this regard, the "low", "median", and "high" of the inhibitor titer were classified by the value of Bethesda unit (BU/mL) as follows:

Low: 0.3 to 1.6 (BU/mL)

Median: 2.0 to 40.5 (BU/mL)

High: 66 to 302 (BU/mL)

2) Preparation of Mixed Specimen

Each of the subject specimens of 1) and a normal plasma were mixed at a volume ratio of 1:1 to prepare a mixed specimen. As the normal plasma, a mixture of all of the normal plasmas of 1) was used.

3) Measurement of Inhibitor Titer (Bethesda Unit)

The inhibitor titer of a specimen was measured by a method for determining a Bethesda unit, which is well-known to a person skilled in the art. After the specimen was diluted with a buffer solution, the diluted specimen was mixed with a normal plasma at a volume ratio of 1:1, the obtained mixture was incubated at 37° C. for 2 hours, and then the FVIII activity was measured, and the Bethesda unit (BU/mL) was determined from the remaining FVIII activity.

4) APTT Measurement

As the APTT reagent, Coagpia APTT-N (manufactured by Sekisui Medical Co., Ltd.) was used, and as the calcium chloride solution, a calcium chloride solution, Coagpia APTT-N (manufactured by Sekisui Medical Co., Ltd.) was used. The APTT measurement was performed by using a blood coagulation automatic analyzer, CP3000 (manufactured by Sekisui Medical Co., Ltd.). The treatment was performed in normal (non-heated) mode or heating mode by the following procedures:

discharging 50 μL of a specimen into a cuvette (reaction vessel); and then heating at 37° C. for 45 seconds (normal mode), or heating at 37° C. for 600 to 720 seconds (heating mode).

After that, 50 μL of an APTT reagent heated to around 37° C. was added into the cuvette, and into the mixture after the lapse of 171 seconds, 50 μL of a 25 mM calcium chloride solution was added to initiate the coagulation reaction. The coagulation reaction was conducted while maintaining the cuvette at around 37° C. In the detection of the coagulation reaction, the cuvette was irradiated with light having a wavelength of 660 nm using a light-emitting diode (LED) as a light source, and the amount of scattered light of 90-degree side scattered light was measured at 0.1-second intervals. The photometric time was set to 360 seconds. For each of the same specimens, the APTT was measured under the non-heating (normal mode) or heating (heating mode) condition, and photometric data were obtained as the coagulation reaction data by APTT measurement.

5) Analysis of Photometric Data

A smoothing treatment including noise removal, and a zero point adjustment for adjusting the amount of scattered light at the starting point of the photometry to be 0 were performed on the obtained photometric data, and a coagulation reaction curve was obtained. Subsequently, the maximum height of the coagulation reaction curve was corrected so as to be 100, and a corrected zero-order curve was obtained. The corrected zero-order curve was primarily differentiated to obtain a corrected primary curve, and the corrected primary curve was further differentiated to obtain a corrected secondary curve.

6) Parameter Extraction

A coagulation time (APTT) was calculated from the obtained corrected zero-order curve. The APTT was a time (T50) to reach 50% height when the maximum height of the corrected zero-order curve was taken as 100%. A maximum primary differential value (Vmax) was acquired from a corrected primary curve, and maximum and minimum secondary differential values (Amax and Amin) were acquired from a corrected secondary curve. Further, parameters related to a weighted average point were calculated from the corrected primary curve and the corrected secondary curve. The calculation target area levels X for calculation of a weighted average point were set to any of 0.5% to 90% with respect to the maximum height Vmax (100%) of the corrected primary curve. For each X, the section where the value of the corrected primary curve satisfies X or more was calculated as the peak width vB. For each of the calculation target areas, by using the above-described formulas (2), (3), and (4), the weighted average time vT and the weighted average height vH were calculated. From the determined vT and vH, the flattening vAB and the time rate vTB were calculated by the following formulas.

$$vAB=(vH/vB)K_1\ (K_1=100)$$

$$vTB=(vT/vB)K_2\ (K_2=1)$$

For each of the acquired parameters, a parameter ratio Pb/Pa, or a parameter difference (Pb−Pa) was determined. In this regard, the Pa is a parameter of a non-heated specimen, and the Pb is a parameter of a heated specimen. In addition, also from an uncorrected zero-order curve, an uncorrected primary curve and an uncorrected secondary curve were calculated similarly, the parameters were calculated similarly from these curves, and the ratio Pb/Pa, or the difference (Pb−Pa) were calculated.

Example 1: Effect of Heating of Subject Specimen on Primary Curve

Corrected primary curves of heated and non-heated LA plasmas (LA) are shown in FIG. 13. In the LA, there was almost no change in the shape of the curve due to the heating. Further, corrected primary curves of heated and non-heated FVIII inhibitor-positive plasmas (IN) are shown in FIG. 14. In the IN, there was almost no change in the shape of the curve due to the heating similarly as in the LA.

Example 2: Effect of Heating of Mixed Specimen on Primary Curve

Corrected primary curves of heated and non-heated mixed plasmas (LA-NP) of a LA plasma (LA) and a normal plasma at 1:1 are shown in FIG. 15A. The peak appeared earlier (coagulation time was shortened) and the shape was sharper than those in FIG. 13 by the mixture of LA with a normal plasma. In the LA-NP, there was almost no change in the shape of the curve due to the heating similarly as in the LA. In addition, corrected primary curves of heated and non-heated mixed plasmas (IN-NP) of a FVIII inhibitor-positive plasma and a normal plasma at 1:1 are shown in FIG. 15B. In the non-heated specimen, the peak appeared earlier and the shape was sharper than those in FIG. 14 similarly as in the LA-NP by the mixture of IN with a normal plasma. On the other hand, the peak appeared late, the peak height was lower, and further the peak width was wider in the heated specimen. It is determined that this shape change is due to the inhibited coagulation reaction of the mixed plasma because of the progress of the antigen-antibody reaction of the inhibitor (anti-FVIII antibody) contained in the IN with the FVIII contained in the normal plasma during the heating treatment. A possibility that the IN is differentiated from the LA by indexing the shape change between the non-heated and the heated as the change in the parameter has been confirmed.

For the mixed specimen with a normal specimen prepared from each of the subject specimens, the parameters related to the coagulation reaction curves of the heated and non-heated specimens were calculated. For the obtained parameters, a parameter Pa of the non-heated specimen, and a parameter Pb of the heated specimen, a parameter ratio Pb/Pa, and a parameter difference Pb−Pa were determined.

Various parameter values obtained from the non-heated specimen and the heated specimen (heating for 10 minutes), and ratios (Pb/Pa) thereof are shown in Table 2. The Pb/Pa of the mixed plasma (IN-NP (mix)) of a FVIII inhibitor plasma was deviated significantly from 1, and was obviously different from a normal plasma (NP), a LA plasma (LA), and a LA-mixed plasma (LA-NP (mix)). Therefore, it was indicated that a FVIII inhibitor-positive plasma was able to be discriminated on the basis of the Pb/Pa of various parameters.

Figure 18A:
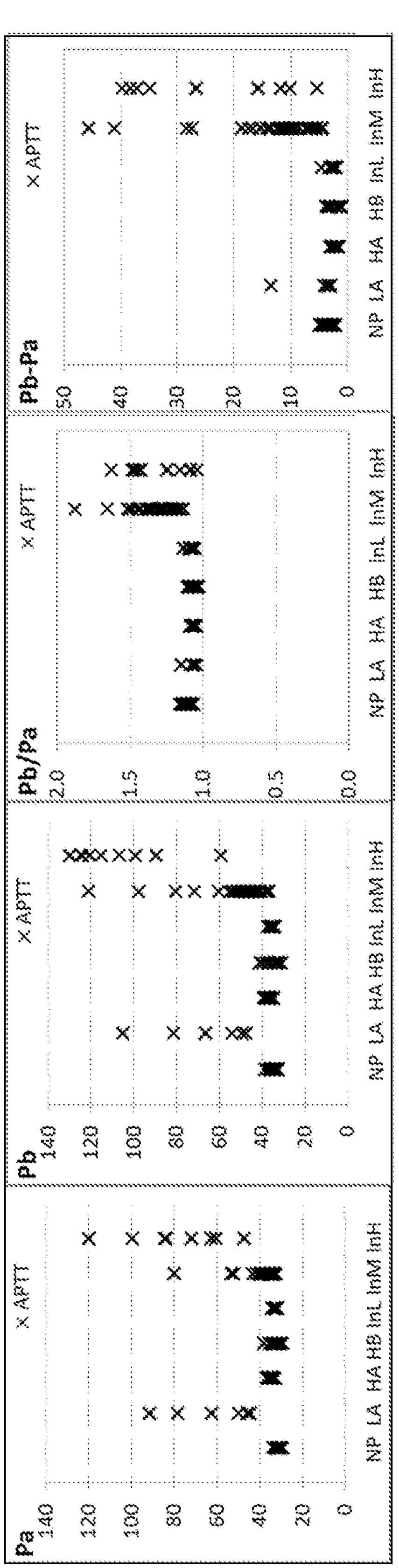
FIG. 18A shows distributions of Pa, Pb, Pb/Pa, and Pb−Pa of APTT for various specimens.

In FIG. 18A, the following results were shown for APTT. In this regard, the term "prolonged" of APTT means that the APTT is longer than that in a normal plasma, and the term "shortened" of APTT means that the APTT is the same value as or a value closer to that in a normal plasma.

In the mixed specimens containing LA, both of the Pa and the Pb are prolonged, and the Pb/Pa is around 1.

In the mixed specimens containing HA and HB, both of the Pa and the Pb are shortened, and the Pb/Pa is around 1.

In the mixed specimens containing InL, both of the Pa and the Pb are shortened, and the Pb/Pa is around 1.

In the mixed specimens containing InM, the Pa is slightly prolonged, the Pb is more prolonged than the Pa, and the Pb/Pa is larger than 1.

In the mixed specimens containing InH, the Pa is prolonged, the Pb is almost the same as or more prolonged than the Pa, and the Pb/Pa is around 1 or larger than 1.

The above results are summarized in Table 3. It has been indicated that on the basis of the APTT of heated and non-heated specimens, the subject specimen contained in a mixed specimen can be discriminated as follows.

(1) If both of the Pa and the Pb are prolonged and further the Pb/Pa is around 1, the subject specimen is LA or InH.

TABLE 2

| | Non-heated (Pa) | | | | | Heated (Pb) | | | | |
|---|---|---|---|---|---|---|---|---|---|---|
| Parameter | NP | LA | LA-NP (mix) | InM | IN-NP (mix) | NP | LA | LA-NP (mix) | InM | IN-NP (mix) |
| APTT (T50) | 26.1 | 62.9 | 51.8 | 151.9 | 49.3 | 26.2 | 67.0 | 51.1 | 145.9 | 80.1 |
| Vmax | 11.4 | 2.9 | 3.8 | 0.7 | 4.3 | 11.1 | 2.7 | 4.0 | 0.8 | 1.9 |
| VmaxT | 23.6 | 58.1 | 49.8 | 120.6 | 47.4 | 23.7 | 63.5 | 49.6 | 81.2 | 75.3 |
| vH10% | 5.9 | 1.6 | 2.2 | 0.3 | 2.4 | 5.9 | 1.5 | 2.2 | 0.4 | 1.1 |
| vT10% | 26.3 | 63.5 | 52.2 | 158.2 | 49.7 | 26.4 | 67.6 | 51.5 | 150.8 | 80.7 |
| vB10% | 14.6 | 55.2 | 40.8 | 241.1 | 35.6 | 14.7 | 57.9 | 39.1 | 217.6 | 80.8 |
| vH10%/vB10% | 40.6 | 2.9 | 5.3 | 0.1 | 6.9 | 40.1 | 2.6 | 5.7 | 0.2 | 1.3 |
| vT10%/vB10% | 1.8 | 1.2 | 1.3 | 0.7 | 1.4 | 1.8 | 1.2 | 1.3 | 0.7 | 1.0 |

| | (Pb/Pa) | | | | |
|---|---|---|---|---|---|
| Parameter | NP | LA | LA-NP (mix) | InM | IN-NP (mix) |
| APTT (T50) | 1.00 | 1.07 | 0.99 | 0.96 | 1.62 |
| Vmax | 0.98 | 0.93 | 1.04 | 1.22 | 0.44 |
| VmaxT | 1.00 | 1.09 | 1.00 | 0.67 | 1.59 |
| vH10% | 0.99 | 0.96 | 1.04 | 1.11 | 0.43 |
| vT10% | 1.00 | 1.06 | 0.99 | 0.95 | 1.63 |
| vB10% | 1.01 | 1.05 | 0.96 | 0.90 | 2.27 |
| vH10%/vB10% | 0.99 | 0.91 | 1.09 | 1.23 | 0.19 |
| vT10%/vB10% | 1.00 | 1.01 | 1.03 | 1.06 | 0.72 |

For various parameters, FIGS. 18A to 18G show parameters Pa in non-heated plasmas, parameters Pb in heated plasmas, ratios Pb/Pa, and differences Pb−Pa, of various plasmas. In median-titer FVIII inhibitor plasmas (InM), the Pb/Pa tended to be larger or smaller than 1, or the Pb−Pa tended to deviate from 0. In addition, in high-titer FVIII inhibitor plasmas (InH), as a whole, the Pb/Pa tended to be larger or smaller than 1, or the Pb−Pa tended to deviate from 0, however, for some of the parameters (APTT, and vT), the Pb/Pa was closer to 1 in some cases. However, for the APTT or vT of InH, even in a case where the Pb/Pa was around 1, the Pb−Pa was not 0, and was prolonged for at least 5 seconds. Therefore, by using the ratio and the difference between Pa and Pb in combination, InH was able to be discriminated by using APTT or vT.

(2) If both of the Pa and the Pb are shortened and further the Pb/Pa is around 1, the subject specimen is HAB (HA or HB) or InL.

(3) If both of the Pa and the Pb are prolonged and further the Pb/Pa is larger than 1, the subject specimen is InM or InH.

TABLE 3

| Symbol | Specimen kind | Non-heated (Pa) | Heated (Pb) | Rate of change (Pb/Pa) |
|---|---|---|---|---|
| LA | LA | Prolonged | Prolonged | Around 1 |
| HAB | Hemophilia A, Hemophilia B | Shortened | Shortened | Around 1 |

TABLE 3-continued

| Symbol | Specimen kind | Non-heated (Pa) | Heated (Pb) | Rate of change (Pb/Pa) |
|---|---|---|---|---|
| InL | Inhibitor titer: low | Shortened | Shortened | Around 1 |
| InM | Inhibitor titer: median | Slightly prolonged | More prolonged than the non-heated | Larger than 1 |
| InH | Inhibitor titer: high | Prolonged | Prolonged | Around 1 or larger than 1 |

Figure 18B:
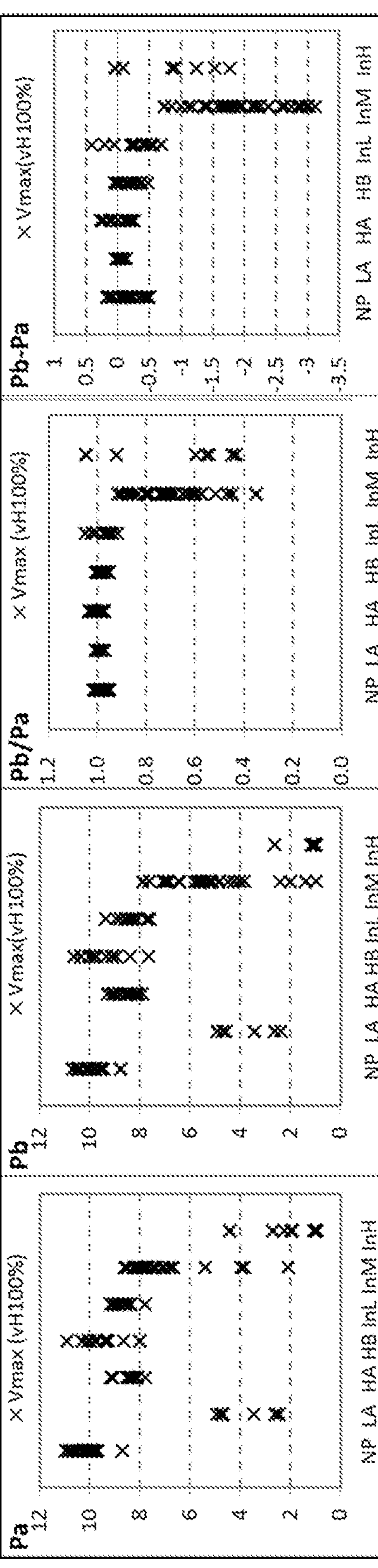
FIG. 18B shows distributions of Pa, Pb, Pb/Pa, and Pb−Pa of Vmax for various specimens.
Figure 18C:
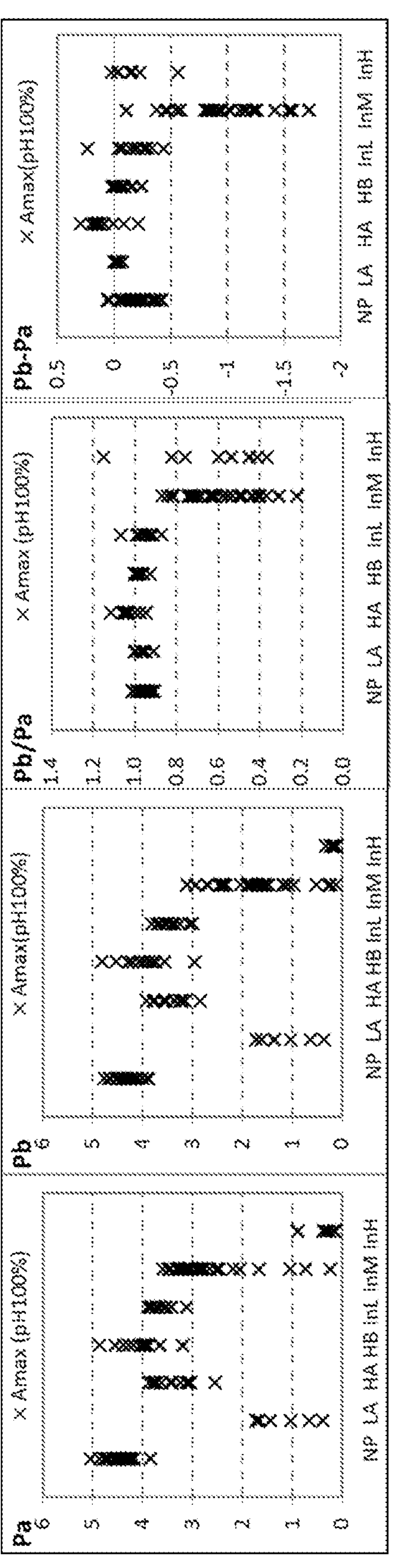
FIG. 18C shows distributions of Pa, Pb, Pb/Pa, and Pb−Pa of Amax for various specimens.
Figure 18D:
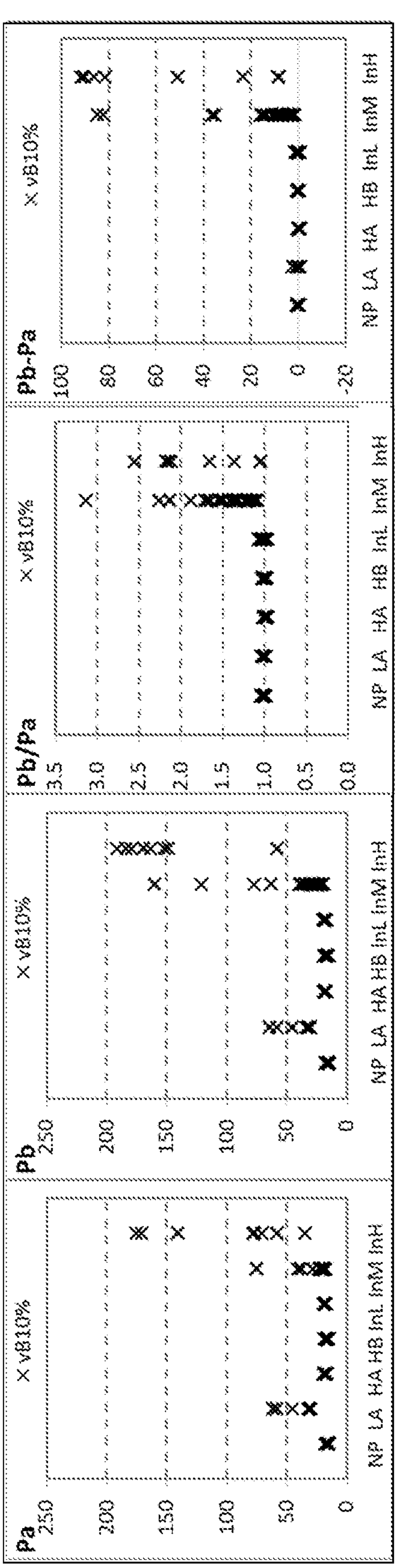
FIG. 18D shows distributions of Pa, Pb, Pb/Pa, and Pb−Pa of vB10% for various specimens.
Figure 18E:
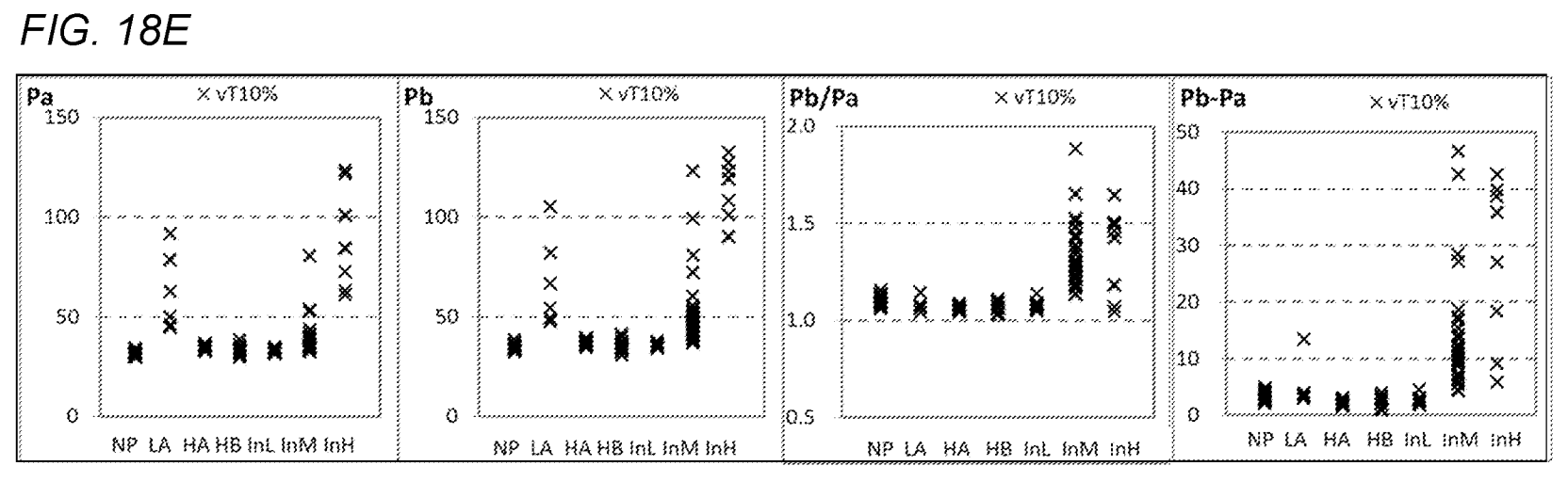
Figure 18F:
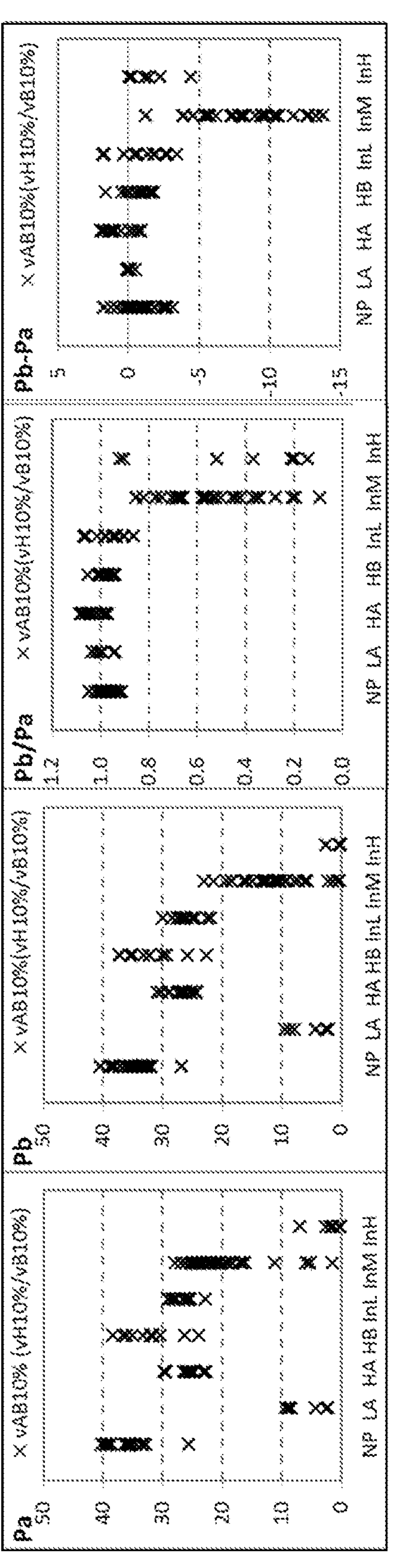
FIG. 18F shows distributions of Pa, Pb, Pb/Pa, and Pb−Pa of vAB10% for various specimens.
Figure 18G:
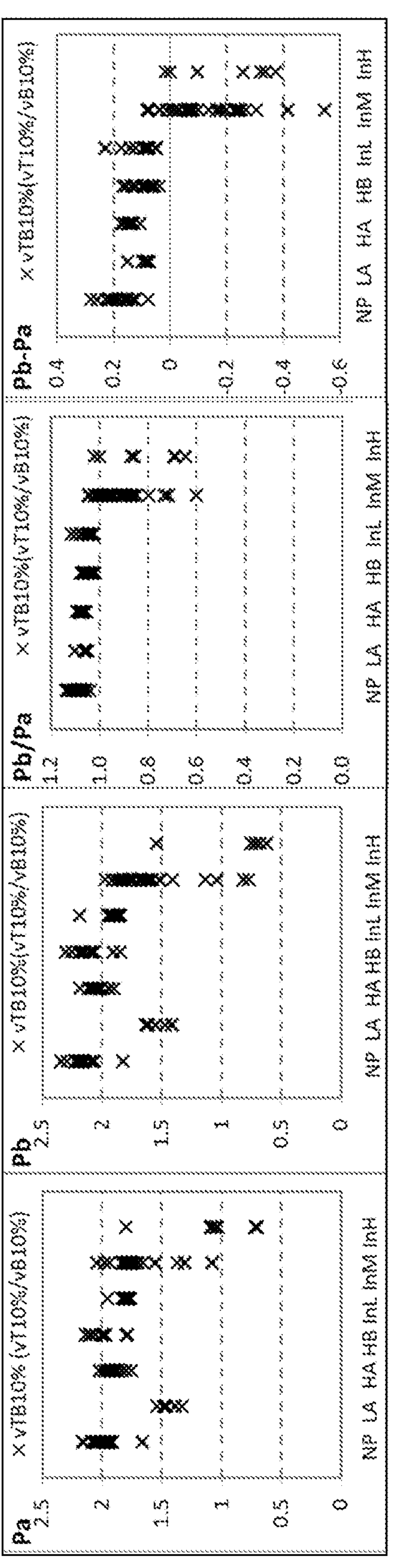
FIG. 18G shows distributions of Pa, Pb, Pb/Pa, and Pb−Pa of vTB10% for various specimens.
Figure 19:
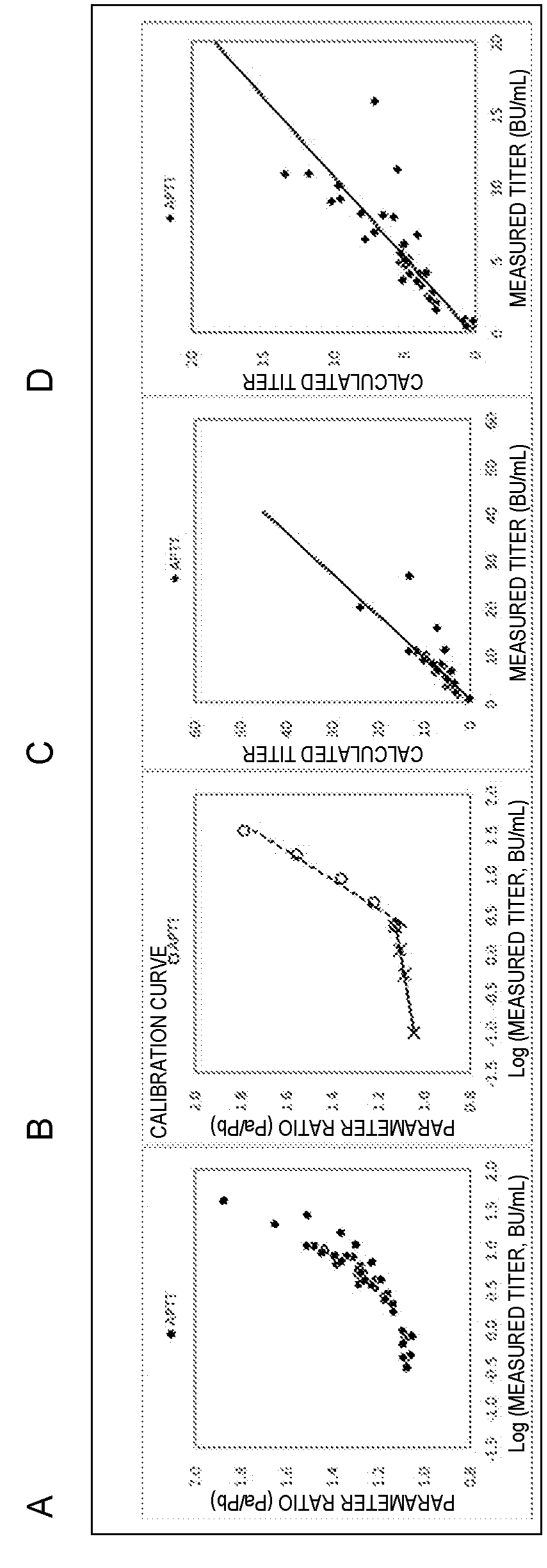
FIG. 19 shows A: plots of Pb/Pa of APTT of an inhibitor-containing mixed specimen to the measured values of the inhibitor titer of the subject specimen, B: a calibration curve, C: plots of calculated values based on the calibration curve shown in B to the measured values of the inhibitor titer of the subject specimen, and D: plots of calculated values to the measured values for the low titer area. In the drawing, the titer is expressed as a logarithmic value.
Figure 20:
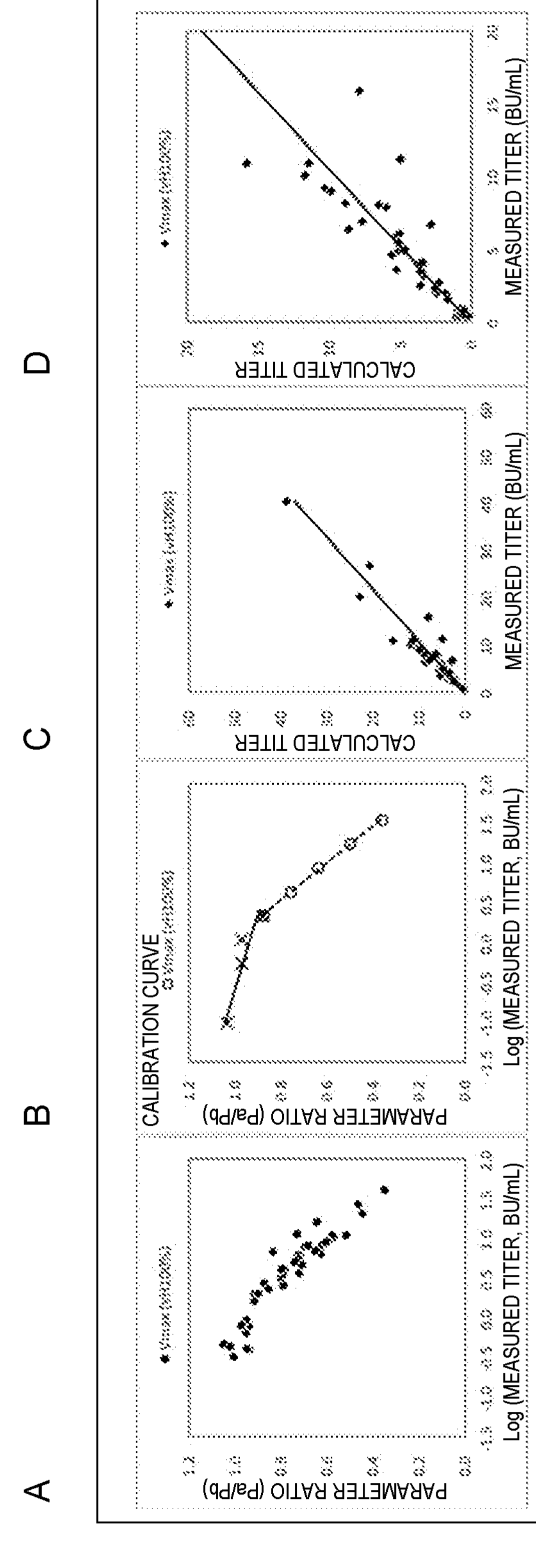
FIG. 20 shows A: plots of Pb/Pa of Vmax of an inhibitor-containing mixed specimen to the measured values of the inhibitor titer of the subject specimen, B: a calibration curve, C: plots of calculated values based on the calibration curve shown in B to the measured values of the inhibitor titer of the subject specimen, and D: plots of calculated values to the measured values for the low titer area. In the drawing, the titer is expressed as a logarithmic value.
Figure 21:
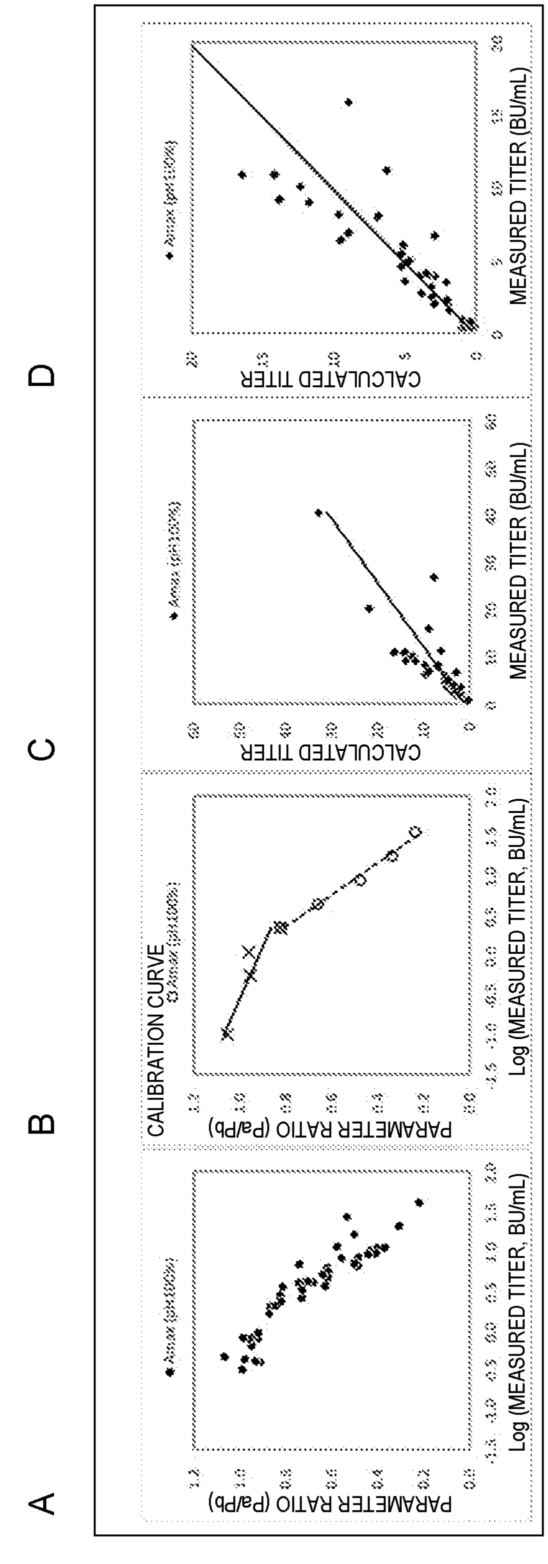
FIG. 21 shows A: plots of Pb/Pa of Amax of an inhibitor-containing mixed specimen to the measured values of the inhibitor titer of the subject specimen, B: a calibration curve, C: plots of calculated values based on the calibration curve shown in B to the measured values of the inhibitor titer of the subject specimen, and D: plots of calculated values to the measured values for the low titer area. In the drawing, the titer is expressed as a logarithmic value.
Figure 22:
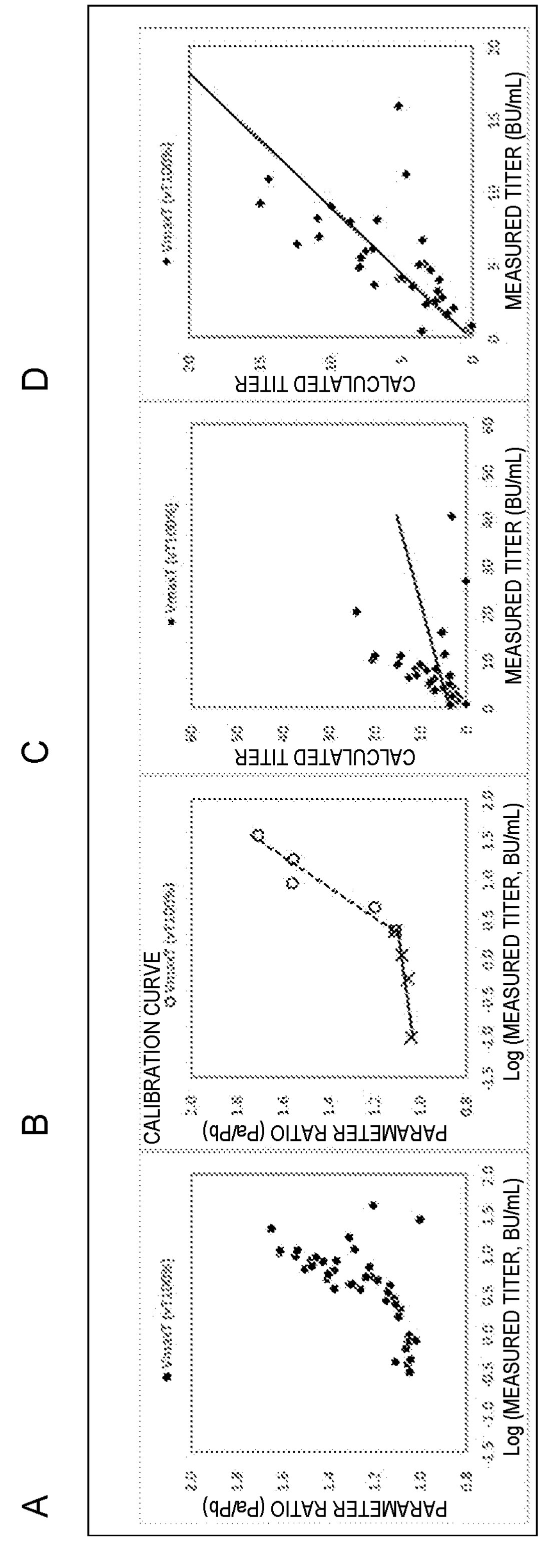
FIG. 22 shows A: plots of Pb/Pa of VmaxT of an inhibitor-containing mixed specimen to the measured values of the inhibitor titer of the subject specimen, B: a calibration curve, C: plots of calculated values based on the calibration curve shown in B to the measured values of the inhibitor titer of the subject specimen, and D: plots of calculated values to the measured values for the low titer area. In the drawing, the titer is expressed as a logarithmic value.
Figure 23:
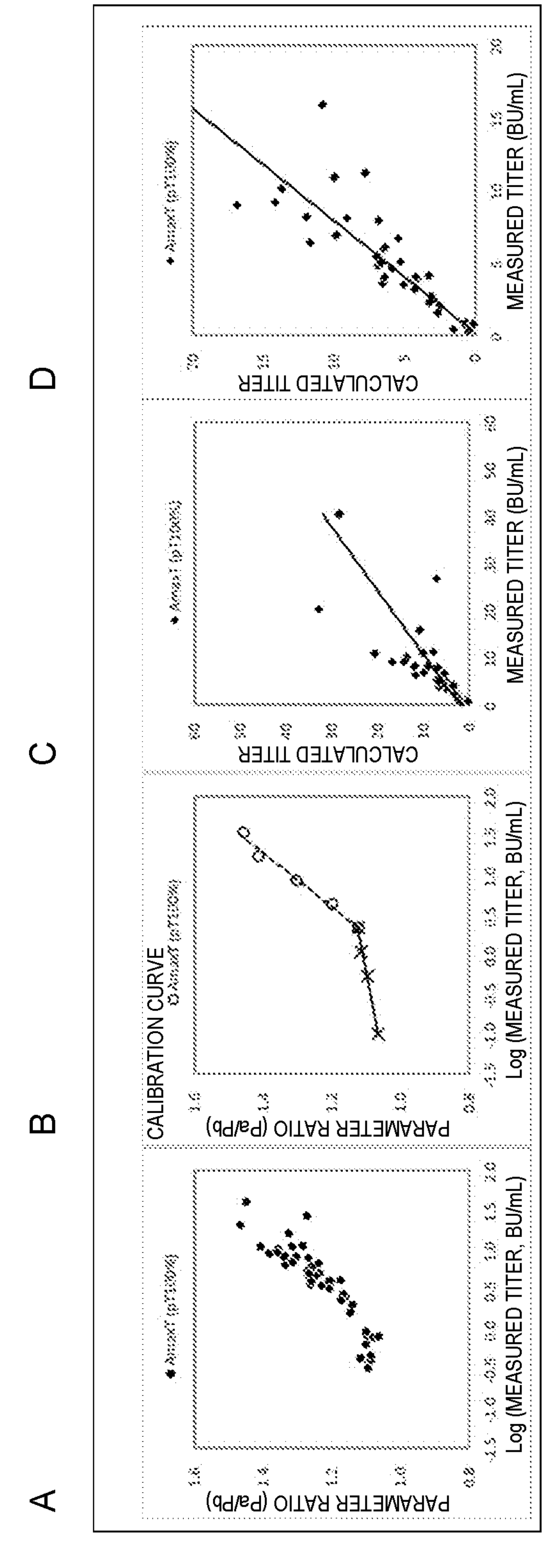
FIG. 23 shows A: plots of Pb/Pa of AmaxT of an inhibitor-containing mixed specimen to the measured values of the inhibitor titer of the subject specimen, B: a calibration curve, C: plots of calculated values based on the calibration curve shown in B to the measured values of the inhibitor titer of the subject specimen, and D: plots of calculated values to the measured values for the low titer area. In the drawing, the titer is expressed as a logarithmic value.
Figure 24:
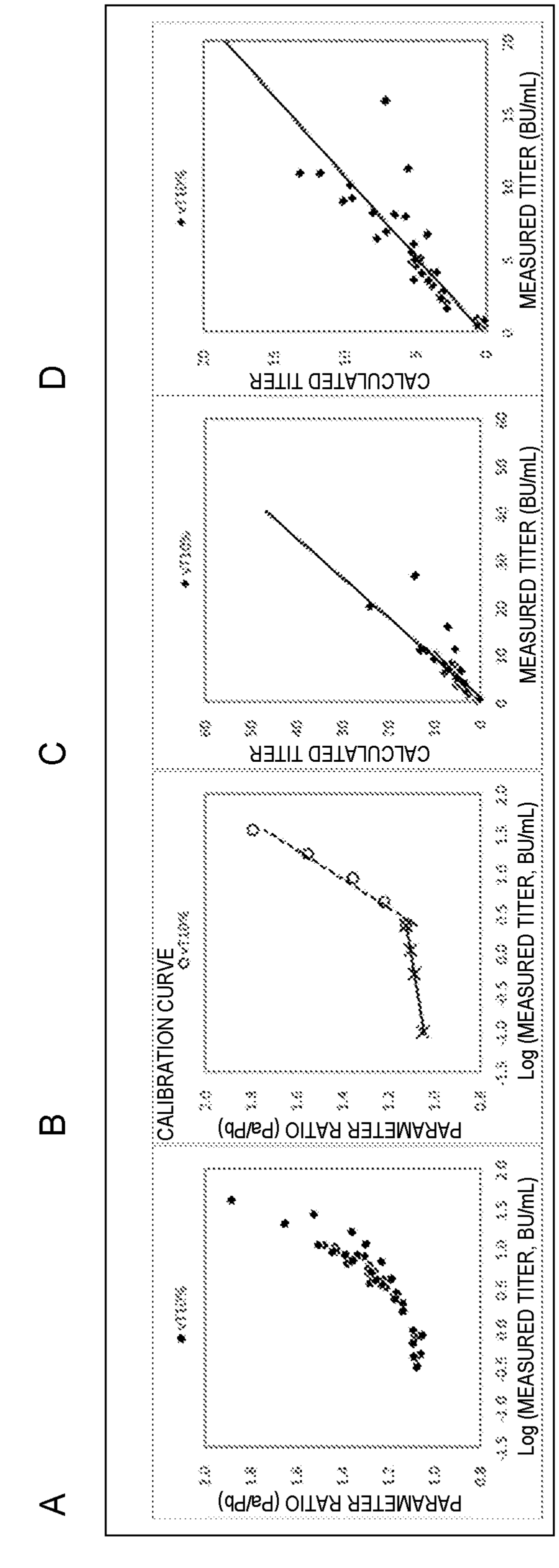
FIG. 24 shows A: plots of Pb/Pa of vT10% of an inhibitor-containing mixed specimen to the measured values of the inhibitor titer of the subject specimen, B: a calibration curve, C: plots of calculated values based on the calibration curve shown in B to the measured values of the inhibitor titer of the subject specimen, and D: plots of calculated values to the measured values for the low titer area. In the drawing, the titer is expressed as a logarithmic value.
Figure 25:
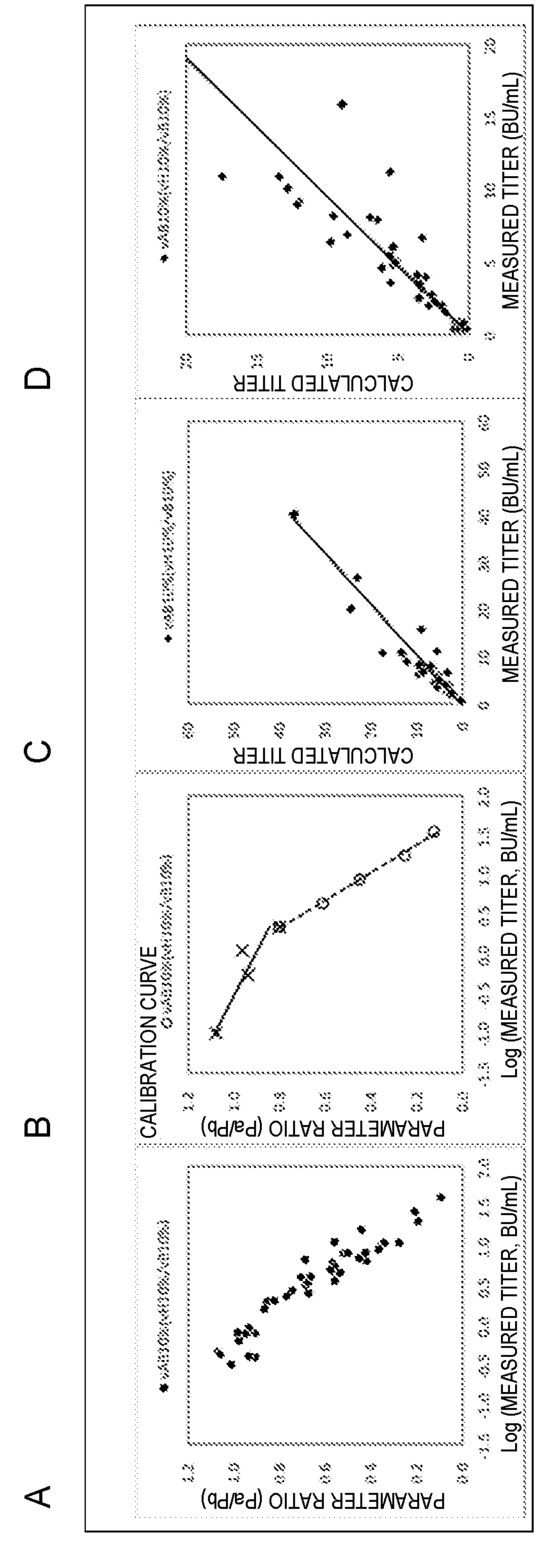
FIG. 25 shows A: plots of Pb/Pa of vAB10% of an inhibitor-containing mixed specimen to the measured values of the inhibitor titer of the subject specimen, B: a calibration curve, C: plots of calculated values based on the calibration curve shown in B to the measured values of the inhibitor titer of the subject specimen, and D: plots of calculated values to the measured values for the low titer area. In the drawing, the titer is expressed as a logarithmic value.
Figure 26:
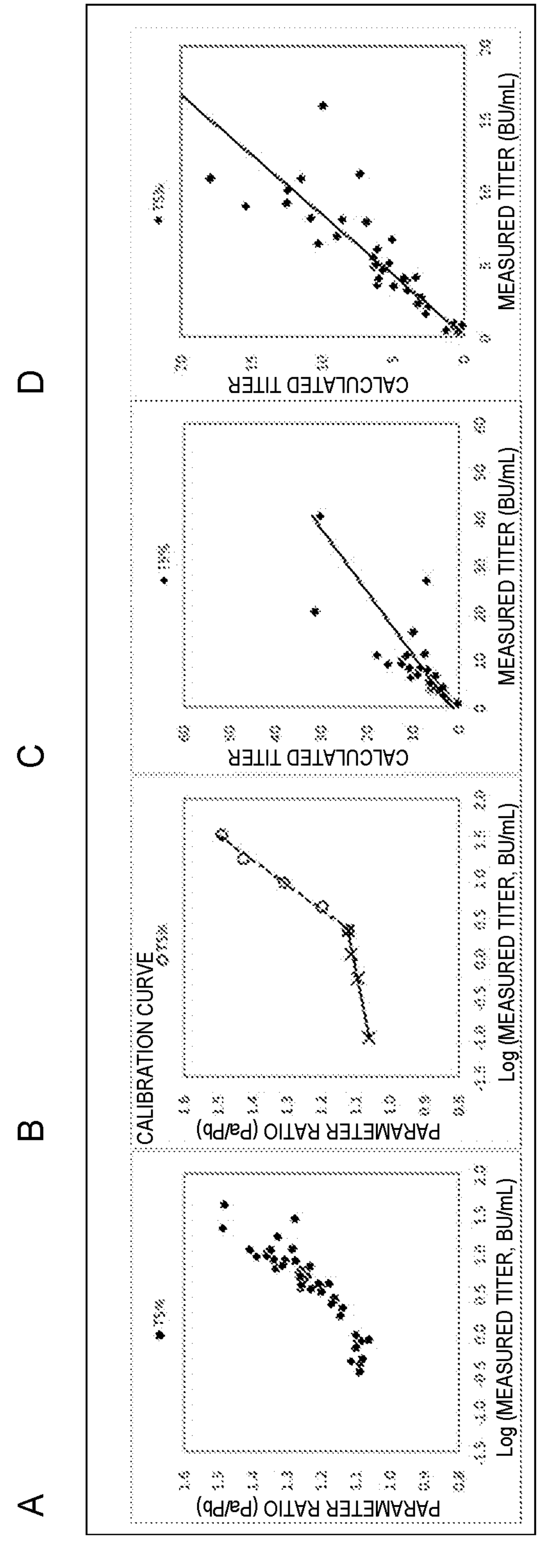
FIG. 26 shows A: plots of Pb/Pa of T5 of an inhibitor-containing mixed specimen to the measured values of the inhibitor titer of the subject specimen, B: a calibration curve, C: plots of calculated values based on the calibration curve shown in B to the measured values of the inhibitor titer of the subject specimen, and D: plots of calculated values to the measured values for the low titer area. In the drawing, the titer is expressed as a logarithmic value.

Further, as shown in FIG. 18B, the Pb/Pa of Vmax was around 1 similarly as in the APTT for LA, HA, HB, InL, and some of InH, and was smaller than 1 for InM and InH except for the some of InH. In a case where the coagulation reaction is inhibited by an inhibitor, the APTT is prolonged and further the coagulation rate is reduced depending on the inhibitor titer, and as a result, the parameter ratio Pb/Pa is deviated from 1. Accordingly, for InM and InH except for the some of InH, the Pb/Pa of APTT was larger than 1, and the Pb/Pa of Vmax was smaller than 1. Some of InH are specimens having a high titer (ultra-high-titer specimens) in a high-titer group, Vmax was decreased to the vicinity of 1 in the non-heated (Pa), and was almost no change in the heated (Pb), and the parameter ratio Pb/Pa was in the vicinity of 1. In order to discriminate the ultra-high-titer specimen in InH, as an example, the specimen may be defined as a specimen having a Vmax of 2 or less in the non-heated (Pa).

Further, as shown in FIGS. 18C to 18G, Amax had a tendency similar to that of Vmax, vB and vT had a tendency similar to that of APTT, and vAB and vTB had a tendency similar to those of Vmax and Amax.

From the results described above, it has been indicated that the specimen of which the APTT prolongation factor is a coagulation factor inhibitor can be discriminated on the basis of the ratio and the difference between Pa and Pb, or the combination of the ratio and the difference, of various parameters.

Example 3: Calculation of Titer of Coagulation Factor Inhibitor Using Ratio or Difference of Parameters 1) Relationship Between Inhibitor Titer and Parameter Value By using subject specimens having different FVIII inhibitor titers, mixed specimens were prepared by the procedure described in Reference Example 1, and Pa, Pb, and Pb/Pa of each of the mixed specimens were calculated. The relationship between the FVIII inhibitor titer and the Pb/Pa was investigated. As the subject specimens, 47 specimens of InL and InM (each having a FVIII inhibitor titer of from 0.3 to 40.5 (BU/mL)) were used. Examples of plots of the Pb/Pa of various parameters obtained from each of the mixed specimens to the logarithmic value of the inhibitor titer of the subject specimen contained in each of the mixed specimens are shown in FIGS. 19A to 26A. The parameters used for the calculation of the Pb/Pa were APTT in FIG. 19A, Vmax in FIG. 20A, Amax in FIG. 21A, VmaxT in FIG. 22A, AmaxT in FIG. 23A, vT10% in FIG. 24A, vAB10% in FIG. 25A, and coagulation time T5 in FIG. 26A. As shown in FIGS. 19A to 26A, the ratio Pb/Pa of each of the parameters is increased or decreased together with the inhibitor titer, and it has been indicated that the Pb/Pa has a correlation with the inhibitor titer. In addition, the distribution of Pb/Pa tended to be different between the low-inhibitor titer area and the high-inhibitor titer area. From these results, when the low-inhibitor titer area and the high-inhibitor titer area are allowed to regress with different lines, it has been suggested that the correlation between the titer and the Pb/Pa is improved.

Figure 27:
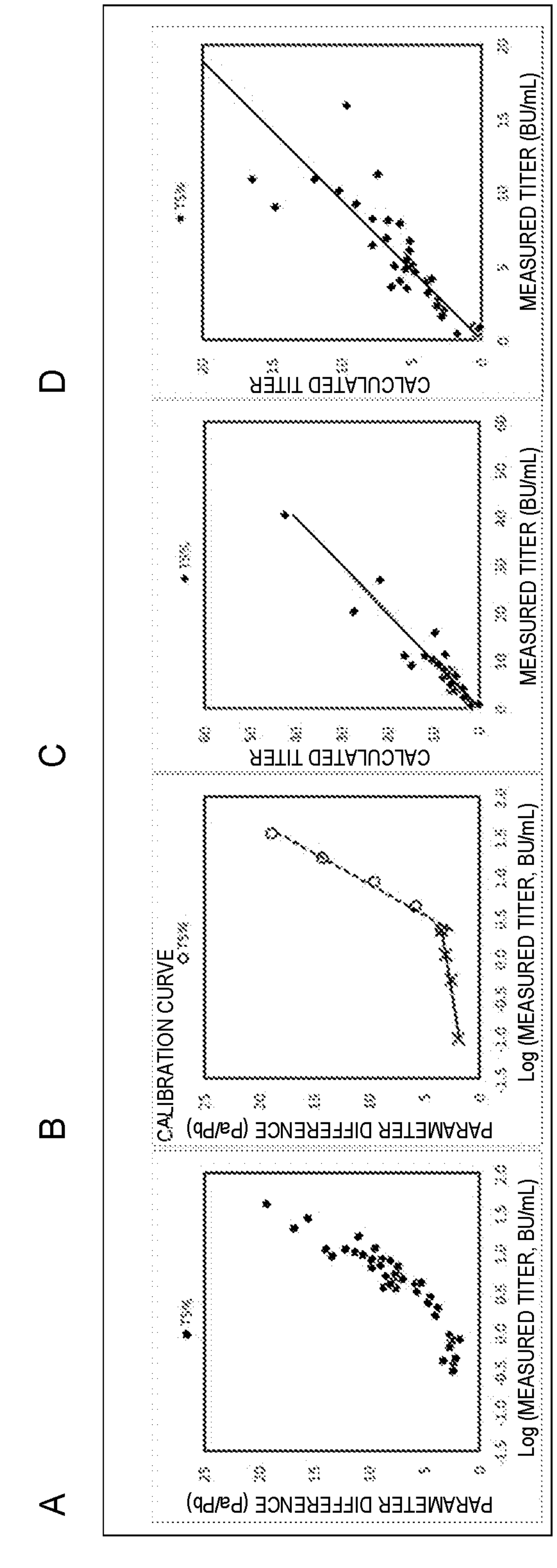
FIG. 27 shows A: plots of Pb−Pa of T5 of an inhibitor-containing mixed specimen to the measured values of the inhibitor titer of the subject specimen, B: a calibration curve, C: plots of calculated values based on the calibration curve shown in B to the measured values of the inhibitor titer of the subject specimen, and D: plots of calculated values to the measured values for the low titer area. In the drawing, the titer is expressed as a logarithmic value.

Plots of the parameter difference Pb−Pa of the coagulation time T5 to the logarithmic value of the inhibitor titer of a subject specimen contained in the mixed specimen are shown in FIG. 27A. It has been indicated that the Pb−Pa has a correlation with the inhibitor titer similarly as in the Pb/Pa.

2) Calculation of Inhibitor Titer Based on Calibration Curve

As described above, by utilizing the fact that the parameter ratio Pb/Pa or the difference Pb−Pa correlates with the logarithmically transformed inhibitor titer, a calibration curve was created by using a specimen of which the FVIII inhibitor titer had been known. As the specimens for creating calibration curves, the total of 8 specimens, which were one FVIII-deficient (HA) specimen, and seven specimens for calibration curve (Cal) having FVIII inhibitor titers of 0.5, 1.1, 2.2, 4.4, 8.7, 17.4, and 34.9 (BU/mL), respectively, were used.

The inhibitor titer of the FVIII-deficient specimen was regarded as 0.1, and a regression line between the logarithmically transformed value of inhibitor titer and the Pb/Pa or Pb−Pa of each specimen was calculated. At that time, the specimens were divided into a group of low-inhibitor titer and a group of high-inhibitor titer, and a regression line was calculated for each group. The titer at the boundary between the low-inhibitor titer and the high-inhibitor titer was set to 2.2 (BU/mL). Examples of the created calibration curve are shown in FIGS. 19B to 27B. The parameters used were the same as in Fig. A. All of the calibration curves were created by a polygonal line consisting of two straight lines.

On the basis of the created calibration curves, the FVIII inhibitor titer (estimated value) of the subject specimen was calculated from the parameter ratio Pb/Pa or the difference Pb−Pa. FIGS. 19C to 27C show plots of calculated values based on the calibration curve to the measured values of the inhibitor titer of each of the subject specimens. FIGS. 19D to 27D show re-plots by using only the data of measured values of 20 BU/mL or less in Fig. C.

Tables 4 to 5 show the tilt, intercept, and correlation coefficient of a regression equation of the calculated titer (y) to the measured titer (x) based on the calibration curve created by using the ratios Pb/Pa of various parameters. Table 4 shows the parameters from the corrected curves (corrected zero-order to secondary curves), and Table 5 shows the parameters from the uncorrected curves (uncorrected zero-order to secondary curves). Further, among them, the parameters showing high correlation are shown in Table 6. In addition, Table 7 shows the tilt, intercept, and correlation coefficient of a regression equation of the calculated titer (y) to the measured titer (x) based on the calibration curve created by using differences Pb−Pa of various parameters. Table 7 shows the parameters from the corrected curves (corrected zero-order to secondary curves), and the parameters from the uncorrected curves (uncorrected zero-order to secondary curves) Further, among them, the parameters showing high correlation are shown in Table 8.

TABLE 4

Regression equation of calculated value based on parameter ratio Pb/Pa from corrected curve to the measured value

| No. | Parameter | Tilt | Intercept | Correlation coefficient |
|---|---|---|---|---|
| 1 | APTT | 1.14 | −0.9 | 0.91 |
| 2 | Vmax (vH100%) | 0.91 | 0.3 | 0.96 |
| 3 | pAUC0.5% | 0.99 | −0.4 | 0.95 |
| 4 | mAUC0.5% | 0.91 | 0.3 | 0.95 |
| 5 | pT1% | 1.08 | −0.3 | 0.83 |
| 6 | pAUC1% | 0.91 | 0.2 | 0.95 |
| 7 | mAUC1% | 0.92 | 0.2 | 0.95 |
| 8 | vH5% | 1.00 | −0.3 | 0.96 |
| 9 | vT5% | 1.18 | −1.1 | 0.91 |
| 10 | vAB5% | 0.90 | 0.5 | 0.95 |
| 11 | vAW5% | 0.89 | 0.6 | 0.94 |
| 12 | vTB5% | 1.13 | −1.4 | 0.93 |
| 13 | vTW5% | 1.10 | −1.3 | 0.93 |
| 14 | pT5% | 1.09 | 0.1 | 0.96 |
| 15 | pAUC5% | 0.94 | 0.2 | 0.92 |
| 16 | mT5% | 1.11 | −0.4 | 0.87 |
| 17 | mAUC5% | 0.98 | −0.2 | 0.95 |
| 18 | vH10% | 1.06 | −0.5 | 0.96 |
| 19 | vT10% | 1.19 | −1.1 | 0.91 |
| 20 | vAB10% | 0.92 | 0.5 | 0.95 |
| 21 | vAW10% | 0.90 | 0.7 | 0.94 |
| 22 | vTW10% | 1.18 | −1.5 | 0.93 |
| 23 | pAUC10% | 0.99 | 0.0 | 0.96 |
| 24 | mT10% | 0.88 | 0.3 | 0.87 |
| 25 | mAUC10% | 1.20 | −1.1 | 0.91 |
| 26 | vH20% | 1.00 | −0.2 | 0.96 |
| 27 | vT20% | 1.13 | −0.8 | 0.91 |
| 28 | vAB20% | 0.89 | 0.7 | 0.94 |
| 29 | vAW20% | 0.88 | 0.7 | 0.94 |
| 30 | vTB20% | 1.14 | −1.4 | 0.93 |
| 31 | vTW20% | 1.06 | −1.2 | 0.94 |
| 32 | pB20% | 0.95 | −0.4 | 0.81 |
| 33 | mH20% | 0.80 | 0.9 | 0.91 |
| 34 | vH30% | 0.97 | −0.1 | 0.96 |
| 35 | vT30% | 1.06 | −0.5 | 0.92 |
| 36 | vAB30% | 0.87 | 0.8 | 0.94 |
| 37 | vAW30% | 0.86 | 0.9 | 0.93 |
| 38 | vTB30% | 1.03 | −1.0 | 0.93 |
| 39 | vTW30% | 0.98 | −0.3 | 0.93 |
| 40 | vH40% | 0.98 | −0.1 | 0.95 |
| 41 | vT40% | 1.05 | −0.4 | 0.92 |
| 42 | vAB40% | 0.87 | 0.8 | 0.94 |
| 43 | vAW40% | 0.87 | 0.9 | 0.94 |
| 44 | vTB40% | 1.10 | −1.3 | 0.93 |
| 45 | vTW40% | 1.08 | −0.6 | 0.95 |
| 46 | pAUC40% | 0.80 | 0.7 | 0.90 |
| 47 | vH50% | 0.96 | 0.0 | 0.95 |
| 48 | vT50% | 0.98 | −0.1 | 0.92 |
| 49 | vTe50% | 1.14 | −1.0 | 0.92 |
| 50 | vTr50% | 1.20 | −1.7 | 0.89 |
| 51 | vB50% | 1.20 | −1.7 | 0.89 |
| 52 | vB50%-vW50% | 0.89 | 0.1 | 0.80 |
| 53 | vAB50% | 0.86 | 0.9 | 0.93 |
| 54 | vAW50% | 0.88 | 0.8 | 0.95 |
| 55 | vTB50% | 1.02 | −0.7 | 0.93 |
| 56 | pB50% | 0.98 | −1.4 | 0.80 |
| 57 | vH60% | 0.96 | −0.1 | 0.95 |
| 58 | vT60% | 0.94 | 0.2 | 0.92 |
| 59 | vTe60% | 1.07 | −0.7 | 0.92 |
| 60 | vTr60% | 1.13 | −1.4 | 0.90 |
| 61 | vB60% | 1.13 | −1.4 | 0.90 |
| 62 | vB60%-vW60% | 0.86 | 0.0 | 0.81 |
| 63 | vAB60% | 0.85 | 0.9 | 0.93 |
| 64 | vAW60% | 0.94 | 0.7 | 0.94 |
| 65 | vTB40% | 0.99 | −0.8 | 0.94 |
| 66 | vH70% | 0.96 | 0.0 | 0.95 |
| 67 | vT70% | 0.87 | 0.6 | 0.91 |
| 68 | vTe70% | 0.98 | −0.2 | 0.93 |
| 69 | vTr70% | 1.08 | −1.0 | 0.92 |
| 70 | vB70% | 1.08 | −1.0 | 0.92 |
| 71 | vAB70% | 0.85 | 1.0 | 0.93 |

TABLE 4-continued

Regression equation of calculated value based on parameter ratio Pb/Pa from corrected curve to the measured value

| No. | Parameter | Tilt | Intercept | Correlation coefficient |
|---|---|---|---|---|
| 72 | vAW70% | 1.01 | 0.3 | 0.96 |
| 73 | vTB70% | 1.04 | −0.7 | 0.95 |
| 74 | pAW70% | 0.82 | 1.1 | 0.81 |
| 75 | vH80% | 0.93 | 0.1 | 0.95 |
| 76 | vT80% | 0.87 | 0.7 | 0.88 |
| 77 | vTe80% | 0.83 | 0.6 | 0.93 |
| 78 | vTr80% | 0.86 | −0.1 | 0.96 |
| 79 | vAW80% | 0.84 | 1.9 | 0.93 |
| 80 | vH90% | 0.89 | 0.3 | 0.96 |

TABLE 5

Regression equation of calculated value based on parameter ratio Pb/Pa from uncorrected curve to measured value

| No. | Parameter | Tilt | Intercept | Correlation coefficient |
|---|---|---|---|---|
| 1 | RVmax (RvH100%) | 1.01 | −0.1 | 0.96 |
| 2 | RvTW0.5% | 0.93 | 0.1 | 0.84 |
| 3 | RpAUC0.5% | 1.18 | −1.1 | 0.95 |
| 4 | RmAUC0.5% | 1.03 | −0.2 | 0.96 |
| 5 | RvAW1% | 0.93 | 1.9 | 0.93 |
| 6 | RpT1% | 1.10 | −0.4 | 0.83 |
| 7 | RpAUC1% | 1.09 | −0.5 | 0.96 |
| 8 | RmAUC1% | 1.05 | −0.3 | 0.96 |
| 9 | RvH5% | 1.11 | −0.7 | 0.95 |
| 10 | RvT5% | 1.18 | −1.1 | 0.91 |
| 11 | RvAB5% | 0.93 | 0.4 | 0.95 |
| 12 | RvAW5% | 0.92 | 0.4 | 0.94 |
| 13 | RvTB5% | 1.11 | −1.2 | 0.94 |
| 14 | RvTW5% | 1.10 | −1.2 | 0.93 |
| 15 | RpT5% | 1.09 | 0.1 | 0.95 |
| 16 | RpAUC5% | 1.08 | −0.5 | 0.93 |
| 17 | RmT5% | 1.11 | −0.4 | 0.87 |
| 18 | RmAUC5% | 1.19 | −1.2 | 0.96 |
| 19 | RvH10% | 1.19 | −1.0 | 0.96 |
| 20 | RvT10% | 1.19 | −1.1 | 0.91 |
| 21 | RvAB10% | 0.96 | 0.4 | 0.95 |
| 22 | RvAW10% | 0.94 | 0.5 | 0.95 |
| 23 | RvTW10% | 1.17 | −1.4 | 0.93 |
| 24 | RpAUC10% | 1.13 | −0.6 | 0.96 |
| 25 | RmH10% | 0.81 | 1.3 | 0.87 |
| 26 | RmT10% | 0.88 | 0.3 | 0.87 |
| 27 | RvH20% | 1.11 | −0.7 | 0.96 |
| 28 | RvT20% | 1.13 | −0.8 | 0.91 |
| 29 | RvAB20% | 0.92 | 0.5 | 0.95 |
| 30 | RvAW20% | 0.91 | 0.5 | 0.95 |
| 31 | RvTB20% | 1.12 | −1.2 | 0.92 |
| 32 | RvTW20% | 1.05 | −1.1 | 0.93 |
| 33 | RpB20% | 0.95 | −0.3 | 0.80 |
| 34 | RpAUC20% | 0.84 | 0.6 | 0.93 |
| 35 | RmH20% | 0.83 | 0.7 | 0.92 |
| 36 | RvH30% | 1.07 | −0.5 | 0.96 |
| 37 | RvT30% | 1.06 | −0.5 | 0.92 |
| 38 | RvAB30% | 0.90 | 0.6 | 0.95 |
| 39 | RvAW30% | 0.89 | 0.7 | 0.94 |
| 40 | RvTB30% | 1.02 | −0.8 | 0.93 |
| 41 | RvTW30 | 0.99 | −0.5 | 0.94 |
| 42 | RpB30% | 0.96 | −0.4 | 0.83 |
| 43 | RpAUC30% | 0.84 | 0.6 | 0.92 |
| 44 | RvH40% | 1.09 | −0.6 | 0.96 |
| 45 | RvT40% | 1.05 | −0.4 | 0.92 |
| 46 | RvAB40% | 0.90 | 0.6 | 0.94 |
| 47 | RvAW40% | 0.90 | 0.7 | 0.94 |
| 48 | RvTB40% | 1.09 | −1.0 | 0.93 |
| 49 | RvAW40% | 1.09 | −0.8 | 0.95 |
| 50 | RpAUC40% | 0.87 | 0.4 | 0.91 |
| 51 | RvH50% | 1.07 | −0.4 | 0.96 |
| 52 | RvT50% | 0.98 | −0.1 | 0.92 |

TABLE 5-continued

| Regression equation of calculated value based on parameter ratio Pb/Pa from uncorrected curve to measured value | | | | |
|---|---|---|---|---|
| No. | Parameter | Tilt | Intercept | Correlation coefficient |
| 53 | RvTe50% | 1.14 | −1.0 | 0.92 |
| 54 | RvTr50% | 1.17 | −1.4 | 0.88 |
| 55 | RvB50% | 1.17 | −1.4 | 0.88 |
| 56 | RvAB50% | 0.89 | 0.7 | 0.94 |
| 57 | RvAW50% | 0.91 | 0.5 | 0.95 |
| 58 | RvTB50% | 1.02 | −0.8 | 0.94 |
| 59 | RpB50% | 0.99 | −1.4 | 0.81 |
| 60 | RpAUC50% | 0.85 | 0.9 | 0.89 |
| 61 | RvH60% | 1.06 | −0.5 | 0.96 |
| 62 | RvT60% | 0.94 | 0.2 | 0.92 |
| 63 | RvTe60% | 1.07 | −0.7 | 0.92 |
| 64 | RvTr60% | 1.11 | −1.1 | 0.89 |
| 65 | RvB60% | 1.11 | −1.1 | 0.89 |
| 66 | RvB60%-RvW60% | 0.86 | 0.1 | 0.81 |
| 67 | RvAB60% | 0.88 | 0.7 | 0.94 |
| 68 | RvAW60% | 0.99 | 0.4 | 0.94 |
| 69 | RvTB60% | 0.99 | −0.8 | 0.94 |
| 70 | RvH70% | 1.07 | −0.5 | 0.96 |
| 71 | RvT70% | 0.87 | 0.6 | 0.91 |
| 72 | RvTe70% | 0.98 | −0.2 | 0.93 |
| 73 | RvTr70% | 1.06 | −0.8 | 0.91 |
| 74 | RvB70% | 1.06 | −0.8 | 0.91 |
| 75 | RvAB70% | 0.88 | 0.7 | 0.94 |
| 76 | RvAW70% | 1.09 | −0.2 | 0.96 |
| 77 | RvTB70% | 1.04 | −0.8 | 0.95 |
| 78 | RvAW70% | 0.85 | 0.9 | 0.82 |
| 79 | RvH80% | 1.03 | −0.3 | 0.96 |
| 80 | RvT80% | 0.87 | 0.7 | 0.88 |
| 81 | RvTe80% | 0.82 | 0.7 | 0.93 |
| 82 | RvTr80% | 0.83 | 0.3 | 0.95 |
| 83 | RvAW80% | 0.87 | 1.7 | 0.92 |
| 84 | RpAUC80% | 0.83 | 0.8 | 0.92 |
| 85 | RvH90% | 0.99 | −0.1 | 0.96 |

TABLE 6

| | | Calculation target area x (% to Vmax) | | | | | | | | | | | | | |
|---|---|---|---|---|---|---|---|---|---|---|---|---|---|---|---|
| Curve | Parameter | 0 | 0.5 | 1 | 5 | 10 | 20 | 30 | 40 | 50 | 60 | 70 | 80 | 90 | 100 |
| Parameters in which regression equation based on Pb/Pa has tilt: within 1 ± 0.2, intercept: within ±3, and correlation coefficient: 0.8 or more | | | | | | | | | | | | | | | |
| Zero-order curve | APTT | B | | | | | | | | | | | | | |
| Primary curve | vH | | | | A | A | A | A | A | A | A | A | A | A | A |
| | vT | | | | A | A | A | A | A | A | A | A | A | | |
| | vTe | | | | | | | | | A | A | A | A | | |
| | vTr | | | | | | | | | A | A | A | A | | |
| | vB | | | | | | | | | A | A | A | | | |
| | vB-vW | | | | | | | | | B | A | | | | |
| | vAB (vH/vB) | | | | A | A | A | A | A | A | A | A | | | |
| | vAW (vH/vW) | | | | A | A | A | A | A | A | A | A | A | | |
| | vTB (vT/vB) | | | | A | | A | A | A | A | A | A | | | |
| | vTW (vT/vW) | | C | | A | A | A | A | A | | | | | | |
| Secondary curve (plus peak) | pT | | | A | A | | | | | | | | | | |
| | pB | | | | | | A | C | | A | | | | | |
| | pAW (pH/pW) | | | | | | | | | | | A | | | |
| | pAUC | | A | A | A | A | C | C | A | C | | | C | | |
| Secondary curve (minus peak) | mH | | | | | C | A | | | | | | | | |
| | mT | | | | A | A | | | | | | | | | |
| | mAUC | | A | A | A | B | | | | | | | | | |
| Parameters in which regression equation based on Pb/Pa has tilt: within 1 ± 0.1, intercept: within ±3, and correlation coefficient: 0.9 or more | | | | | | | | | | | | | | | |
| Primary curve | vH | | | | B | B | B | A | A | A | A | A | A | C | A |
| | vT | | | | | | | A | A | A | A | | | | |
| | vTe | | | | | | | | | | A | A | | | |
| | vTr | | | | | | | | | | | A | | | |
| | vB | | | | | | | | | | | A | | | |
| | vAB (vH/vB) | | | | A | A | C | | C | | | | | | |
| | vAW (vH/vW) | | | C | C | A | C | | C | C | A | A | | | |
| | vTB (vT/vB) | | | | | | | A | C | A | A | A | | | |
| | vTW (vT/vW) | | | | C | | A | A | A | | | | | | |
| Secondary curve | pT | | | | A | | | | | | | | | | |
| | pAUC | | B | A | A | B | | | | | | | | | |
| | mAUC | | A | A | B | | | | | | | | | | |

A: Both of those with correction treatment and without correction treatment

B: With correction treatment

C: Without correction treatment

TABLE 7

| Regression equation of calculated value based on parameter difference Pb − Pa to measured value | | | | | | | | | |
|---|---|---|---|---|---|---|---|---|---|
| No. | Parameter (curve with correction treatment) | Tilt | Intercept | Correlation coefficient | No. | Parameter (curve without correction treatment) | Tilt | Intercept | Correlation coefficient |
| 1 | T5 | 1.00 | 0.2 | 0.96 | 1 | RT5 | 1.00 | 0.2 | 0.96 |
| 2 | AmaxT (pT100%) | 0.97 | 0.5 | 0.95 | 2 | RAmaxT (RpT100%) | 0.97 | 0.5 | 0.95 |
| 3 | vTs5% | 0.81 | 1.4 | 0.87 | 3 | RvTs5% | 0.81 | 1.4 | 0.87 |
| 4 | vTB5% | 0.84 | −0.2 | 0.93 | 4 | RvTB5% | 0.84 | −0.2 | 0.93 |
| 5 | mW5% | 1.10 | −0.9 | 0.93 | 5 | RmW5% | 1.11 | −0.9 | 0.93 |
| 6 | vTs10% | 0.84 | 1.2 | 0.90 | 6 | RvTs10% | 0.84 | 1.2 | 0.90 |
| 7 | vTB10% | 1.03 | −0.7 | 0.91 | 7 | RvTB10% | 1.03 | −0.7 | 0.91 |
| 8 | vTW10% | 0.90 | 0.0 | 0.90 | 8 | RvTW10% | 0.90 | 0.0 | 0.90 |
| 9 | pT10% | 0.87 | 1.0 | 0.91 | 9 | RpT10% | 0.87 | 1.0 | 0.91 |
| 10 | vTs20% | 0.91 | 0.9 | 0.93 | 10 | RvTs20% | 0.91 | 0.9 | 0.93 |
| 11 | vTB20% | 0.85 | 0.0 | 0.91 | 11 | RvTB20% | 0.85 | 0.0 | 0.91 |
| 12 | pT20% | 0.92 | 0.8 | 0.93 | 12 | RpT20% | 0.92 | 0.8 | 0.93 |
| 13 | vTs30% | 0.91 | 0.8 | 0.93 | 13 | RvTs30% | 0.91 | 0.8 | 0.93 |
| 14 | pT30% | 0.96 | 0.6 | 0.95 | 14 | RpT30% | 0.96 | 0.6 | 0.95 |
| 15 | vTs40% | 0.91 | 0.8 | 0.93 | 15 | RvTs40% | 0.91 | 0.8 | 0.93 |
| 16 | vTB40% | 0.82 | 0.1 | 0.90 | 16 | RvTB40% | 0.82 | 0.1 | 0.90 |
| 17 | pT40% | 0.94 | 0.6 | 0.94 | 17 | RpT40% | 0.94 | 0.6 | 0.94 |
| 18 | pB40%-pW40% | 0.83 | 1.3 | 0.93 | 18 | RpB40%-RpW40% | 0.83 | 1.3 | 0.93 |
| 19 | vTs50% | 0.90 | 0.8 | 0.93 | 19 | RmAUC40% | 1.03 | 1.5 | 0.83 |
| 20 | vTW50% | 0.95 | 0.5 | 0.87 | 20 | RvTs50% | 0.90 | 0.8 | 0.93 |
| 21 | pT50% | 0.95 | 0.6 | 0.94 | 21 | RvTW50% | 0.95 | 0.5 | 0.87 |
| 22 | vTs60% | 0.91 | 0.8 | 0.93 | 22 | RpT50% | 0.95 | 0.6 | 0.94 |
| 23 | pT60% | 0.95 | 0.6 | 0.95 | 23 | RvTs60% | 0.91 | 0.8 | 0.93 |
| 24 | vTs70% | 0.87 | 0.9 | 0.91 | 24 | RpT60% | 0.95 | 0.6 | 0.95 |
| 25 | pT70% | 0.95 | 0.6 | 0.95 | 25 | RvTs70% | 0.87 | 0.9 | 0.91 |
| 26 | pT80% | 0.95 | 0.6 | 0.95 | 26 | RpT70% | 0.95 | 0.6 | 0.95 |
| 27 | pT90% | 0.96 | 0.6 | 0.95 | 27 | RpT80% | 0.95 | 0.6 | 0.95 |
| | | | | | 28. | RpT90% | 0.96 | 0.6 | 0.95 |

TABLE 8

| Curve | Parameter | Calculation target area x (% to Vmax) | | | | | | | | | | | | | |
|---|---|---|---|---|---|---|---|---|---|---|---|---|---|---|---|
| | | 0 | 0.5 | 1 | 5 | 10 | 20 | 30 | 40 | 50 | 60 | 70 | 80 | 90 | 100 |
| Parameters in which regression equation based on Pb − Pa has tilt: within 1 ± 0.2, intercept: within ±3, and correlation coefficient: 0.8 or more | | | | | | | | | | | | | | | |
| Zero-order curve | T5 | | | | | | | | | | | | | | A |
| Primary curve | vTs | | | | A | A | A | A | A | A | A | A | | | |
| | vTB (vT/vB) | | | | A | A | A | | A | | | | | | |
| | vTW (vT/vW) | | | | | A | | | | A | | | | | |
| Secondary curve | pT | | | | | A | A | A | A | A | A | A | A | A | A |
| | pB-pW | | | | | | | | A | | | | | | |
| | mW | | | | A | | | | | | | | | | |
| | mAUC | | | | | | | | C | | | | | | |
| Parameters in which regression equation based on Pb − Pa has tilt: within 1 ± 0.1, intercept: within ±3, and correlation coefficient: 0.9 or more | | | | | | | | | | | | | | | |
| Zero-order curve | T5 | | | | | | | | | | | | | | A |
| Primary curve | vTs | | | | | | A | A | A | | A | | | | |
| | vTB (vT/vB) | | | | | A | | | | | | | | | |
| Secondary curve | pT | | | | | | A | A | A | A | A | A | A | A | A |

A: Both of those with correction treatment and without correction treatment

B: With correction treatment

C: Without correction treatment

Tables 9 to 10 show the tilt, intercept, and correlation coefficient of a regression equation of the calculated titer (y) to the measured titer (x) based on the calibration curve created by using the ratios Pb/Pa of various parameters other than those in Tables 4 to 5. Table 9 shows the parameters from the corrected primary curve, and Table 10 shows the parameters from the uncorrected primary curve. Further, among them, the parameters showing high correlation are shown in Table 11.

TABLE 9

Regression equation of calculated value based on parameter ratio Pb/Pa from the corrected primary curve to measured value

| No. | Parameter | Tilt | Intercept | Correlation coefficient |
|---|---|---|---|---|
| 1 | vHa5% | 0.98 | −0.2 | 0.96 |
| 2 | vAWa70% | 1.00 | 0.4 | 0.96 |
| 3 | vHa10% | 1.03 | −0.4 | 0.96 |
| 4 | vHa90% | 0.89 | 0.4 | 0.96 |
| 5 | vHa80% | 0.93 | 0.1 | 0.95 |
| 6 | vHa30% | 0.95 | 0.0 | 0.95 |
| 7 | vHa2 0% | 0.98 | −0.1 | 0.95 |
| 8 | vHa40% | 0.97 | −0.1 | 0.95 |
| 9 | vHa50% | 0.95 | 0.0 | 0.95 |
| 10 | vHa7 0% | 0.95 | 0.0 | 0.95 |
| 11 | vHa60% | 0.95 | 0.0 | 0.95 |
| 12 | vABa10% | 0.92 | 0.6 | 0.95 |
| 13 | vABa5% | 0.90 | 0.6 | 0.95 |
| 14 | vAWa50% | 0.87 | 0.8 | 0.94 |
| 15 | vAWa1% | 0.91 | 1.6 | 0.94 |
| 16 | vAWa60% | 0.94 | 0.7 | 0.94 |
| 17 | vAWa10% | 0.89 | 0.7 | 0.94 |
| 18 | vABa20% | 0.88 | 0.7 | 0.94 |
| 19 | vAWa5% | 0.89 | 0.7 | 0.94 |
| 20 | vABa30% | 0.86 | 0.8 | 0.94 |
| 21 | vAWa20% | 0.87 | 0.7 | 0.94 |
| 22 | vABa40% | 0.87 | 0.8 | 0.94 |
| 23 | vAWa40% | 0.87 | 0.9 | 0.93 |
| 24 | vAWa30% | 0.86 | 0.9 | 0.93 |
| 25 | vABa50% | 0.85 | 0.9 | 0.93 |
| 26 | vABa60% | 0.84 | 0.9 | 0.93 |
| 27 | vAWa80% | 0.84 | 1.9 | 0.93 |
| 28 | vABa70% | 0.85 | 1.0 | 0.93 |
| 29 | vTa50% | 1.02 | −0.2 | 0.92 |
| 30 | vTm50% | 1.02 | −0.2 | 0.92 |
| 31 | vTm60% | 0.96 | 0.1 | 0.92 |
| 32 | vTa60% | 0.96 | 0.1 | 0.92 |
| 33 | vTa30% | 1.11 | −0.8 | 0.92 |
| 34 | vTm30% | 1.11 | −0.8 | 0.92 |
| 35 | vTa40% | 1.10 | −0.7 | 0.92 |
| 36 | vTm40% | 1.10 | −0.7 | 0.92 |
| 37 | vTm70% | 0.89 | 0.5 | 0.92 |
| 38 | vTa70% | 0.89 | 0.5 | 0.92 |
| 39 | vTa80% | 0.91 | 0.5 | 0.89 |
| 40 | vHa1% | 0.99 | 1.7 | 0.84 |

TABLE 10

Regression equation of calculated value based on parameter ratio Pb/Pa from uncorrected primary curve to measured value

| No. | Parameter | Tilt | Intercept | Correlation coefficient |
|---|---|---|---|---|
| 1 | RvHa8 0% | 1.02 | −0.2 | 0.96 |
| 2 | RvHa30% | 1.06 | −0.4 | 0.96 |
| 3 | RvHa10% | 1.15 | −0.8 | 0.96 |
| 4 | RvHa90% | 0.98 | 0.0 | 0.96 |
| 5 | RvAWa70% | 1.08 | −0.1 | 0.96 |
| 6 | RvHa20% | 1.09 | −0.5 | 0.96 |
| 7 | RvHa40% | 1.07 | −0.5 | 0.96 |
| 8 | RvHa60% | 1.05 | −0.4 | 0.96 |
| 9 | RvHa50% | 1.05 | −0.4 | 0.96 |
| 10 | RvHa70% | 1.06 | −0.4 | 0.96 |
| 11 | RvHa5% | 1.08 | −0.5 | 0.95 |
| 12 | RvABa10% | 0.95 | 0.4 | 0.95 |
| 13 | RvAWa50% | 0.91 | 0.5 | 0.95 |
| 14 | RvABa5% | 0.93 | 0.4 | 0.95 |
| 15 | RvAWa10% | 0.93 | 0.6 | 0.95 |
| 16 | RvABa20% | 0.91 | 0.6 | 0.95 |
| 17 | RvABa30% | 0.89 | 0.6 | 0.94 |
| 18 | RvAWa60% | 0.99 | 0.4 | 0.94 |
| 19 | RvAWa5% | 0.91 | 0.5 | 0.94 |
| 20 | RvAWa20% | 0.90 | 0.6 | 0.94 |
| 21 | RvABa40% | 0.90 | 0.6 | 0.94 |
| 22 | RvAWa40% | 0.90 | 0.8 | 0.94 |
| 23 | RvABa50% | 0.88 | 0.7 | 0.94 |
| 24 | RvAWa30% | 0.88 | 0.7 | 0.94 |
| 25 | RvABa60% | 0.87 | 0.7 | 0.94 |
| 26 | RvABa70% | 0.88 | 0.8 | 0.93 |
| 27 | RvAWa80% | 0.84 | 2.2 | 0.90 |

TABLE 11

| Curve | Parameter | Calculation target area x (% to Vmax) | | | | | | | | | | | |
|---|---|---|---|---|---|---|---|---|---|---|---|---|---|
| | | 0.5 | 1 | 5 | 10 | 20 | 30 | 40 | 50 | 60 | 70 | 80 | 90 |
| Parameters in which regression equation based on Pb/Pa has tilt: within 1 ± 0.2, intercept: within ±3, and correlation coefficient: 0.8 or more | | | | | | | | | | | | | |
| Primary curve | vHa | | B | A | A | A | A | A | A | A | A | A | A |
| | vTa | | | | | | A | A | A | A | A | A | |
| | vABa (vHa/vB) | | | A | A | A | A | A | A | A | A | | |
| | vAWa (vHa/vW) | | B | A | A | A | A | A | A | A | A | A | |
| | vTm | | | | | | A | A | A | A | A | | |
| Parameters in which regression equation based on Pb/Pa has tilt: within 1 ± 0.1, intercept: within ±3, and correlation coefficient: 0.9 or more | | | | | | | | | | | | | |
| Primary curve | vHa | | | A | B | A | A | A | A | A | A | A | C |
| | vTa | | | | | | | | A | A | | | |
| | vABa (vHa/vB) | | | C | A | C | | | | | | | |
| | vAWa (vHa/vW) | | B | C | C | C | | | C | A | A | | |
| | vTm | | | | | | | | A | A | | | |

A: Both of those with correction treatment and without correction treatment

B: With correction treatment

C: Without correction treatment

Example 5: Calculation of Inhibitor Titer by Specimen Dilution of High-Inhibitor Titer Specimen For a high-inhibitor titer specimen of which the inhibitor titer is higher than the titer range of a calibration curve obtained in Example 3, a titer was calculated on the basis of the calibration curve using the parameters similar to the above parameters by using the diluted specimen, and by multiplying the resultant titer by the dilution ratio, the calculated titer was obtained.

Figure 28:
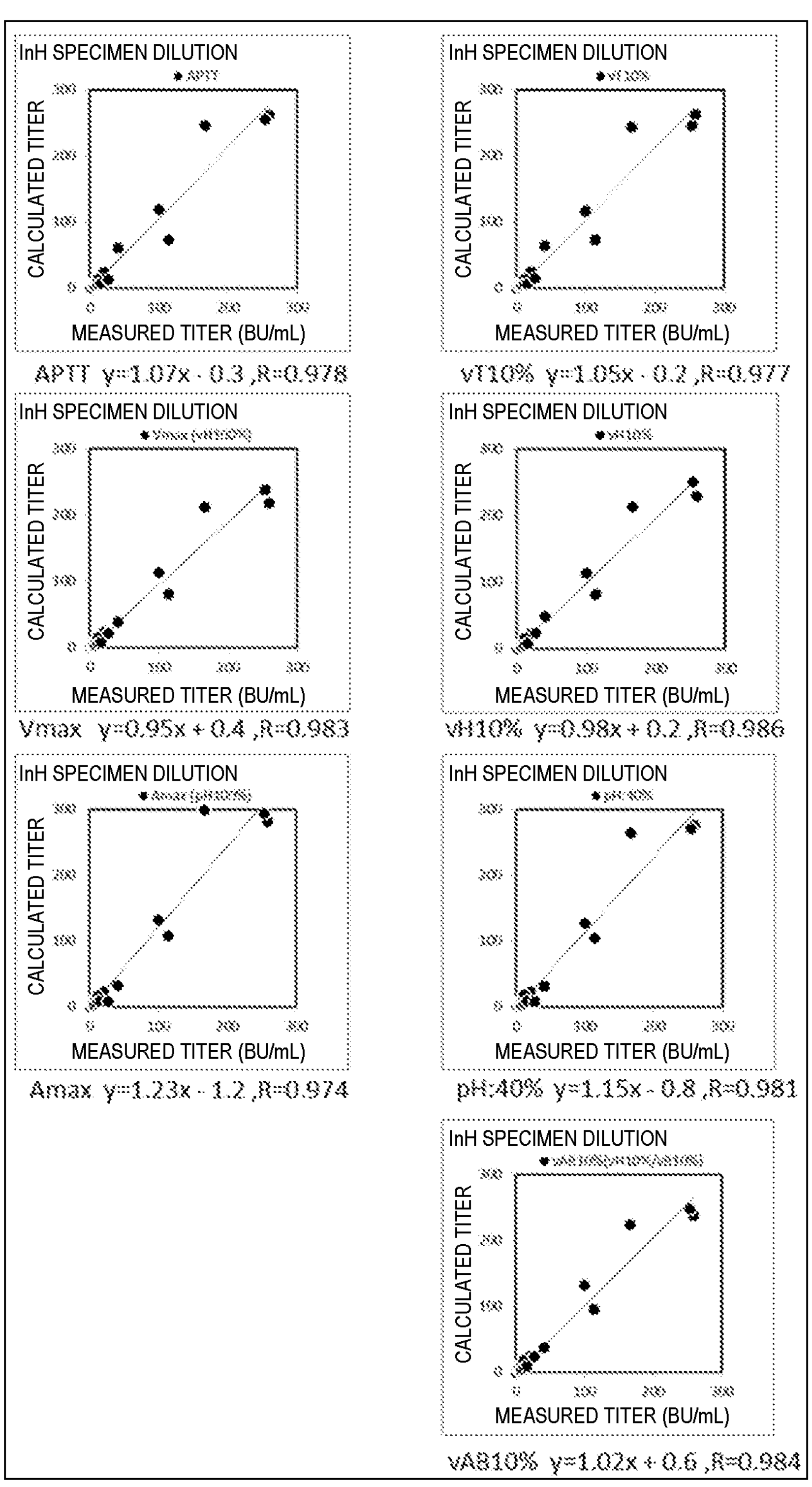
FIG. 28 shows diagrams of plots of the calculated titers obtained from diluted specimens with high inhibitor titers to the measured titers.

Specifically, as the subject specimen, five specimens of InH having inhibitor titers of 99, 113, 166, 253, and 259 (BU/mL), respectively were used. Each of the subject specimens was diluted 10 times with a normal plasma, and the resultant 10-time diluted specimen and a normal plasma were mixed at a volume ratio of 1:1 to prepare a mixed specimen. Pa, Pb, and Pb/Pa of the mixed specimen were determined by a similar procedure as in Reference Example 1, the titer of the diluted specimen was calculated on the basis of the calibration curve used in Example 3, and by multiplying the resultant titer by the dilution ratio, the calculated titer was obtained. The results were combined with the results for 47 specimens of InL and InM. FIG. 28 shows plots of the calculated titers for 47 specimens of InL and InM and calculated titers of five specimens of InH obtained in the above to the measured titers. Below each diagram of the plots, the regression equation and correlation coefficient between the calculated titers and the measured titers are shown. Favorable correlation was obtained for all of the parameters, and it was confirmed that the high-titer specimens can be measured by specimen dilution treatment.

The invention claimed is:

1. A method for electronically measuring a titer of a coagulation factor inhibitor in a subject blood specimen using a processor, comprising:

obtaining, from a subject, the subject blood specimen;

preparing a mixed specimen containing the subject blood specimen and a reference blood specimen;

heating, with a heater, the mixed specimen and acquiring, with a first clotting time test, a first coagulation reaction curve for the heated mixed specimen;

preparing a second mixed specimen containing the subject blood specimen and the reference blood specimen;

acquiring, with a second clotting time test, a second coagulation reaction curve for the second mixed specimen, the second mixed specimen having not been subjected to the heating;

calculating, using the processor, a first parameter related to the second coagulation reaction curve of the second mixed specimen that has not been subjected to the heating;

calculating, using the processor, a second parameter related to the first coagulation reaction curve of the heated mixed specimen; and determining a measurement of the titer of the coagulation factor inhibitor in the subject blood specimen on a basis of a ratio or a difference between the first parameter and the second parameter, wherein the first parameter related to the second coagulation reaction curve is at least one parameter selected from the group consisting of: a parameter related to a primary differential curve of the second coagulation reaction curve, and a parameter related to a secondary differential curve of the second coagulation reaction curve, the second parameter related to the first coagulation reaction curve is at least one parameter selected from the group consisting of: a parameter related to a primary differential curve of the first coagulation reaction curve, and a parameter related to a secondary differential curve of the first coagulation reaction curve, the first parameter and the second parameter are each a parameter related to a weighted average point in a predetermined area of the primary differential curve or the secondary differential curve, and wherein the weighted average point is a weighted average point of the primary differential curve represented by coordinates (vT, vH) defined by a weighted average time vT and a weighted average height vH, wherein when the primary differential curve is defined as F(t) (t represents time) and a time when F(t) is a predetermined value X is defined as t1, t2 (t1<t2), the vT and the vH are represented by the following formulas, respectively:

$$vT = \frac{M}{\sum_{i=t1}^{t2} F(i)} \tag{3}$$

$$vH = \frac{M}{\sum_{i=t1}^{t2} i} \tag{4}$$

wherein $$M = \sum_{i=t1}^{t2} (i \times F(i)), \tag{2}$$

the parameter related to the weighted average point includes one or more parameters selected from the group consisting of the vT, the vH, a peak width vB, a weighted average peak width vW, a flattening vAB, a time rate vTB, a flattening vAW, a time rate vTW, an average time vTa, an average height vHa, vTm, vABa, and vAWa, wherein the peak width vB is a length of time satisfying F(t)≥X from the t1 to t2, the weighted average peak width vW is a length of time satisfying F(t)≥vH from the t1 to t2, the vAB represents a ratio between the vH and the vB, the vTB represents a ratio between the vT and the vB, the vAW represents a ratio between the vH and the vW, the vTW represents a ratio between the vT and the vW, when F(t), t1 and t2 have the same definitions as described above, and a number of data points from F(t1) to F(t2) is defined as n, the vTa, the vHa, and the vTm are represented by the following formulas, respectively:

$$vTa = \frac{\sum_{i=t1}^{t2} i}{n} \tag{5}$$

$$vHa = \frac{\sum_{i=t1}^{t2} F(i)}{n} \tag{6}$$

$$vTm = \frac{t1 + t2}{2} \tag{7}$$

the vABa represents a ratio between the vHa and the vB, and the vAWa represents a ratio between the vHa and the vW, or the weighted average point is a weighted average point of a plus peak of the secondary differential curve represented by coordinates (pT, pH) defined by a weighted average time pT and a weighted average height pH, wherein when the secondary differential curve is defined as F'(t) (t represents time) and a time when F'(t) is a predetermined value X is defined as t1, t2 (t1<t2), the pT and the pH are represented by the following formulas, respectively:

$$pT = \frac{M}{\sum_{i=t1}^{t2} F'(i)} \tag{3'}$$

$$pH = \frac{M}{\sum_{i=t1}^{t2} i} \tag{4'}$$

wherein $$M = \sum_{i=t1}^{t2} (i \times F'(i)), \tag{2'}$$

the parameter related to the weighted average point includes one or more parameters selected from the group consisting of the pT, the pH, a peak width pB, a weighted average peak width pW, a flattening pAB, a time rate pTB, a flattening pAW, and a time rate pTW, wherein the peak width pB is a length of time satisfying F'(t)≥X from the t1 to t2, the weighted average peak width pW is a length of time satisfying F'(t)≥pH from the t1 to t2, the pAB represents a ratio between the pH and the pB, the pTB represents a ratio between the pT and the pB, the pAW represents a ratio between the pH and the pW, and the pTW represents a ratio between the pT and the pW, or the weighted average point is a weighted average point of a minus peak of the secondary differential curve represented by coordinates (mT, mH) defined by a weighted average time mT and a weighted average height mH, wherein when the secondary differential curve is defined as F'(t) (t represents time) and a time when F'(t) is a predetermined value X is defined as t1, t2 (t1<t2), the mT and the mH are represented by the following formulas, respectively:

$$mT = \frac{M}{\sum_{i=t1}^{t2} F'(i)} \tag{3''}$$

-continued $$mH = \frac{M}{\sum_{i=t1}^{t2} i} \tag{4''}$$

wherein $$M = \sum_{i=t1}^{t2} (i \times F'(i)), \tag{2'}$$

the parameter related to the weighted average point includes one or more parameters selected from the group consisting of the mT, the mH, a peak width mB, a weighted average peak width mW, a flattening mAB, a time rate mTB, a flattening mAW, and a time rate mTW, wherein the peak width mB is a length of time satisfying F'(t)≤X from the t1 to t2, the weighted average peak width mW is a length of time satisfying F'(t)≤mH from the t1 to t2, the mAB represents a ratio between the mH and the mB, the mTB represents a ratio between the mT and the mB, the mAW represents a ratio between the mH and the mW, and the mTW represents a ratio between the mT and the mW.

2. The method according to claim 1, wherein the titer of the coagulation factor inhibitor in the subject blood specimen is calculated on a basis of a calibration curve from the ratio or the difference between the first parameter and the second parameter.

3. The method according to claim 1, wherein the coagulation factor inhibitor is a blood coagulation factor VIII inhibitor.

4. The method according to claim 1, wherein the mixed specimen contains the subject blood specimen and the reference blood specimen at a volume ratio of 1:9 to 9:1.

5. The method according to claim 4, further comprising diluting the subject blood specimen before mixing with the reference blood specimen, or diluting the mixed specimen prepared.

6. The method according to claim 1, wherein the heating of the mixed specimen is performed at 30° C. or more and 40° C. or less for 2 to 30 minutes.

7. The method according to claim 1, wherein the subject blood specimen is a blood specimen showing prolongation of APTT due to a presence of the coagulation factor inhibitor.

8. The method according to claim 1, wherein the titer of the coagulation factor inhibitor is calculated in Bethesda units.

* * * * *